United States Patent
Udupa et al.

(10) Patent No.: US 11,443,433 B2
(45) Date of Patent: Sep. 13, 2022

(54) QUANTIFICATION AND STAGING OF BODY-WIDE TISSUE COMPOSITION AND OF ABNORMAL STATES ON MEDICAL IMAGES VIA AUTOMATIC ANATOMY RECOGNITION

(71) Applicant: The Trustees of the University of Pennsylvania, Philadelphia, PA (US)

(72) Inventors: Jayaram K. Udupa, Philadelphia, PA (US); Tiange Liu, Qinhuangdao (CN); Drew A. Torigian, Philadelphia, PA (US); Dewey Odhner, Horsham, PA (US); Yubing Tong, Norwood, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 16/271,949

(22) Filed: Feb. 11, 2019

(65) Prior Publication Data
US 2019/0259159 A1   Aug. 22, 2019

Related U.S. Application Data

(60) Provisional application No. 62/628,943, filed on Feb. 10, 2018.

(51) Int. Cl.
*G06K 9/00* (2022.01)
*G06T 7/11* (2017.01)
(Continued)

(52) U.S. Cl.
CPC ............... *G06T 7/11* (2017.01); *A61B 5/055* (2013.01); *A61B 5/4519* (2013.01);
(Continued)

(58) Field of Classification Search
CPC ..... A61B 34/10; A61B 5/7267; A61B 5/7275; A61B 5/4869; A61B 5/4872;
(Continued)

(56) References Cited

U.S. PATENT DOCUMENTS 6,023,637 A * 2/2000 Liu ................... A61B 5/015
                                                  128/922
6,358,208 B1 * 3/2002 Lang ................. A61B 5/412
                                                  600/438
(Continued)

OTHER PUBLICATIONS

Narasimhan R, Fornango JP. Some further experiments in the parallel processing of pictures, IEEE Transaction on Electronic Computers, EC-13:748-750, 1963.
(Continued)

*Primary Examiner* — Alex Kok S Liew
(74) *Attorney, Agent, or Firm* — BakerHostetler

(57) ABSTRACT

Quantification of body composition plays an important role in many clinical and research applications. Radiologic imaging techniques such as Dual-energy X-ray absorptiometry, magnetic resonance imaging (MRI), and computed tomography (CT) imaging make accurate quantification of the body composition possible. This disclosure presents an automated, efficient, accurate, and practical body composition quantification method for low dose CT images; method for quantification of disease from images; and methods for implementing virtual landmarks.

20 Claims, 29 Drawing Sheets

(51) Int. Cl.
| | |
|---|---|
| *A61B 5/055* | (2006.01) |
| *A61B 5/00* | (2006.01) |
| *A61B 6/03* | (2006.01) |
| *A61B 6/00* | (2006.01) |
| *G06T 7/00* | (2017.01) |
| *G06T 7/187* | (2017.01) |
| *G06F 16/51* | (2019.01) |
| *G16H 30/40* | (2018.01) |
| *A61B 34/10* | (2016.01) |
| *G06V 10/25* | (2022.01) |

(52) U.S. Cl.
CPC .......... *A61B 5/4842* (2013.01); *A61B 5/4872* (2013.01); *A61B 5/7267* (2013.01); *A61B 5/7275* (2013.01); *A61B 6/032* (2013.01); *A61B 6/037* (2013.01); *A61B 6/505* (2013.01); *A61B 6/5217* (2013.01); *A61B 34/10* (2016.02); *G06F 16/51* (2019.01); *G06T 7/0012* (2013.01); *G06T 7/187* (2017.01); *G06V 10/25* (2022.01); *G16H 30/40* (2018.01); *G06T 2207/30004* (2013.01); *G06V 2201/031* (2022.01)

(58) Field of Classification Search
CPC ..... A61B 5/0013; A61B 5/1128; A61B 6/547; A61B 1/00009; A61B 2034/105; A61B 2090/373; A61B 5/0064; A61B 5/6843; A61B 8/4245; G06K 2209/051; G06K 9/3233; G06K 9/6282; G06K 9/4604; G06K 9/627; G06K 9/3241; G06K 9/4638; G06K 9/6224; G06K 9/469; G06K 2209/05; G06K 9/00; G06K 9/0014; G06K 9/00288; G06K 9/62; G06K 9/6231; G06K 9/6253; G06T 7/11; G06T 7/187; G06T 2207/30004; G06T 2207/10081; G06T 2207/20156; G06T 2207/20016; G06T 7/70; G06T 19/00; G06T 7/74; G06T 7/0014; G06T 7/0012; G06T 7/12; G06T 2207/30101; G06T 7/149; G06T 7/155; G06T 5/002; G06T 2200/04; G06T 2207/10088; G06T 2207/30096; G06T 5/30; G06T 7/136; G06T 11/008; G06T 15/08; G06T 17/10; G06T 2207/20161; G06T 2207/30048; G06T 2207/30064; G06T 5/005; G06T 7/62; G06T 2207/30016; G06T 2207/10072; G06T 2207/20081; G06T 2207/30068; G06T 7/162; G06T 2207/1076; G06T 2207/10132; G06T 2207/20076; G06T 2207/20192; G06T 2207/30061; G06T 7/174; G06T 17/00; G16H 30/40; G16H 50/20; G16H 50/50; A61N 5/1039; A61N 2005/1061; A61N 5/0616; G01R 33/5608; A61L 27/18; A61L 27/3804; A61L 27/3826; G09B 23/30; G09B 23/303; G01J 3/44; G01N 21/274; G02B 21/0052; G02B 21/06
USPC ........ 382/128, 129, 130, 131, 132; 600/424, 600/474, 412, 473, 549
See application file for complete search history.

(56) References Cited

U.S. PATENT DOCUMENTS

| | | | | |
|---|---|---|---|---|
| 8,270,687 B2* | 9/2012 | Nakashima | ........... | G06T 7/0012 128/922 |
| 2003/0078498 A1* | 4/2003 | Lang | ................... | A61B 5/6843 600/437 |
| 2003/0088320 A1* | 5/2003 | Sale | ....................... | G05B 17/02 700/30 |
| 2005/0171428 A1* | 8/2005 | Fichtinger | ............ | A61N 5/1014 600/426 |
| 2007/0058865 A1* | 3/2007 | Li | ........................ | G06K 9/6224 382/173 |
| 2009/0221999 A1* | 9/2009 | Shahidi | .............. | A61B 18/1815 606/33 |
| 2009/0259167 A1* | 10/2009 | Sakamoto | ............... | A61P 35/00 604/21 |
| 2010/0069742 A1* | 3/2010 | Partain | ................. | G06K 9/3241 600/424 |
| 2010/0131075 A1* | 5/2010 | Ludlow | ............... | A61L 27/3882 623/23.66 |
| 2010/0217161 A1* | 8/2010 | Shalgi | ................. | A61B 8/4245 601/2 |
| 2011/0129817 A1* | 6/2011 | Banchereau | ........ | C12Q 1/6883 435/6.15 |
| 2012/0157842 A1* | 6/2012 | Davis | ...................... | A61N 7/02 600/439 |
| 2013/0089186 A1* | 4/2013 | Payne | .................... | A61B 6/583 378/207 |
| 2014/0023993 A1* | 1/2014 | Zeng | .................... | G01J 3/0218 433/215 |
| 2014/0275969 A1* | 9/2014 | Lau | ....................... | A61B 5/055 600/412 |
| 2015/0036910 A1* | 2/2015 | Kelly | .................... | G06T 7/0012 382/131 |
| 2015/0285789 A1* | 10/2015 | Montano | ........... | G01N 33/5061 514/291 |
| 2015/0348259 A1* | 12/2015 | Souza | .................... | G06T 7/187 382/131 |
| 2016/0106512 A1* | 4/2016 | Biffi | ...................... | A61B 34/10 382/128 |
| 2017/0091574 A1* | 3/2017 | Udupa | ................. | A61N 5/1039 |
| 2018/0165808 A1* | 6/2018 | Bagci | .................... | A61B 6/032 |
| 2020/0167921 A1* | 5/2020 | Kelly | .................... | G06T 7/0012 |

OTHER PUBLICATIONS

NEMA, I.B.P.S. International Standard: Radionuclide Imaging Devices Characteristics and Test Conditions Part 1: Positron Emission Tomographs. Technical Report. International Electro-technical Commission (IEC), 1998. https://wiki.cancerimagingarchive.net/display/Public/RIDER+Phantom+PET-CT.

Nguyen T, Lau D C W. The Obesity Epidemic and Its Impact on Hypertension. Can J Cardiol. 2012; 28(3): 326-333.

Okada T, Linguraru MG, Hori M, Summers RM, Tomiyama M, Sato Y. Abdominal multi-organ segmentation from CT images using conditional shape—location and unsupervised intensity priors, Medical Image Analysis, 26: 1-18, 2015.

Oliveira et al., "Visceral and Subcutaneous Adipose Tissue FDG Uptake by PET/CT in Metabolically Healthy Obese Subjects", Obesity, 2015, 23(2), 286-289.

Organization W H. Obesity: Preventing and Managing the Global Epidemic. World Health Organization Technical Report. 1998; 894(1): 1-253.

Pak et al., "Comparison of Visceral Fat Measures with Cardiometabolic Risk Factors in Healthy Adults", Plos One, 2016, 11(4), 1-10.

Philips software for disease measurement: http://www.usa.philips.com/healthcare/solutions/advanced-molecular-imaging/pet-ct.

Pizer SM, Fletcher PT, Joshi S, Thall A, Chen JZ, Fridman Y, Fritsch DS, Gash AG, Glotzer JM, Jiroutek MR, Lu CL, Muller KE, Tracton G, Yushkevich P, Chaney EL. Deformable M-reps for 3D medical image segmentation. International Journal of Computer Vision 55, 85-106, 2003.

Pope D, Parker D, Gustafson D, Clayton P. Dynamic Search Algorithm in Left Ventricular Border Recognition and Analysis of Coronary Arteries, IEEE Proceedings of Computers in Cardiology, 9:71-75, 1984.

Precision Medicine Initiative Cohort Program, National Institute of Health, https://www.nih.gov/precision-medicine-initiative-cohort-program, 2016, 3 pages.

(56) References Cited

OTHER PUBLICATIONS

Quantitative imaging Biomarkers AllianceTM (QIBATM). http://www.rsna.org/qiba/.
Robbins KT, Clayman G, Levine PA, et al. Neck dissection classification update: revisions proposed by the American Head and Neck Society and the American Academy of Otolaryngology—Head and Neck Surgery. Arch Otolaryngol Head Neck Surg, 128(7): 751-758, 2002.
Robbins KT, Shaha AR, Medina JE, et al. Consensus statement on the classification and terminology of neck dissection. Arch Otolaryngol Head Neck Surg, 134(5): 536-538, 2008.
Rousson M, Paragios N. Prior knowledge, level set representations & visual grouping. International Journal of Computer Vision 76, 231-243, 2008.
Rueda S. 2D and 3D Digital Shape Modeling Strategies, PhD Thesis, University of Nottingham Jun. 2010.
Rusch VW, Asamura H, Watanabe H, Giroux DJ, Rami-Porta R, Goldstraw P. The IASLC lung cancer staging project: a proposal for a new international lymph node map in the forthcoming seventh edition of the TNM classification for lung cancer. Journal of Thoracic Oncology, 4(5): 568-577, 2009.
Saha, P.K., Udupa, J.K., 2001. Relative fuzzy connectedness among multiple objects: Theory, algorithms, and applications in image segmentation. Computer Vision and Image Understanding 82, 42-56.
Salles G, de Jong D, Xie W, Rosenwald A, Chhanabhai M, Gaulard P, Klapper W, Calaminici M, Sander B, Thorns C, Campo E, Molina T, Lee A, Pfreundschuh M, Horning S, Lister A, Sehn LH, Raemaekers J, Hagenbeek A, Gascoyne RD, Weller E. Prognostic significance of immunohistochemical biomarkers in diffuse large B-cell lymphoma: a study from the Lunenburg Lymphoma Biomarker Consortium. Blood. Jun. 30, 2011;117(26):7070-8. doi: 10.1182/blood-2011-04-345256. Epub May 2, 2011. PubMed PMID: 21536860.
Scott DW, Mottok A, Ennishi D, Wright GW, Farinha P, Ben-Neriah S, Kridel R, Barry GS, Hother C, Abrisqueta P, Boyle M, Meissner B, Telenius A, Savage KJ, Sehn LH, Slack GW, Steidl C, Staudt LM, Connors JM, Rimsza LM, Gascoyne RD. Prognostic Significance of Diffuse Large B-Cell Lymphoma Cell of Origin Determined by Digital Gene Expression in Formalin-Fixed Paraffin-Embedded Tissue Biopsies. J Clin Oncol. Sep. 10, 2015;33(26):2848-56. doi: 10.1200/JCO.2014.60.2383. Epub Aug. 3, 2015. PubMed PMID: 26240231; PubMed Central PMCID: PMC4554747.
Sebastiano K M D, Yang L, Zbuk K, et al. Accelerated Muscle and Adipose Tissue Loss May Predict Survival in Pancreatic Cancer Patients: the Relationship with Diabetes and Anaemia. Brit J Nutr. 2013; 109(2): 302-312.
Shattuck DW, Mirza M, Adisetiyo V, Hojatkashani C, Salamon G, Narr KL, Poldrack RA, Bilder RM, Toga AW. Construction of a 3D probabilistic atlas of human cortical structures. Neuroimage 39, 1064-1080, 2008.
Shen TA, Li HS, Huang XL. Active Volume Models for Medical Image Segmentation. IEEE Transactions on Medical Imaging 30, 774-791, 2011.
Shen W, Punyanitya M, Wang Z, et al. Total Body Skeletal Muscle and Adipose Tissue Volumes: Estimation from A Single Abdominal Cross-Sectional 639 Image. J Appl Physiol. 2004; 97(6): 2333-2338.
Shin H, Lu L, Kim L, Seff A, Yao J, Summers R. Interleaved text/image deep mining on a large-scale radiology image database, IEEE Conf. on CVPR, pp. 1-10, 2015.
Shrout, PE, Fleiss, JL. Intra-class correlations: Uses in assessing rater reliability. Psychological Bulletin 86: 420-428, 1979.
Singer J P, Peterson E R, Snyder M E, et al. Body Composition and Mortality After Adult Lung Transplantation in the United States. Am J Resp Crit Care. 2014; 190(9): 1012-1021.
Smith K, Clark K, Bennett W, Nolan T, Kirby J, Wolfsberger M, Moulton J, Vendt B, Freymann J. Data From RIDER_PHANTOM_PET-CT. (2015). http://dx.doi.org/10.7937/K9/TCIA.2015.8WG2KN4W.
Som PM, Curtin HD, Mancuso AA. An imaging-based classification for the cervical nodes designed as an adjunct to recent clinically based nodal classifications. Arch Otolaryngol Head Neck Surg, 125(4): 388-396, 1999.
Som PM, Curtin HD, Mancuso AA. Imaging-based nodal classification for evaluation of neck metastatic adenopathy. AJR Am J Roentgenol, 174(3): 837-844, 2000.
Song X, Zhou XH, Ma S. Nonparametric ROC Based Evaluation for Survival Outcomes. Statistics in Medicine, 31(23): 2660-2675, 2012. http://doi.org/10.1002/sim.5386.
Song Y, Cai W, Kim J, Feng DD. A multistage discriminative model for tumor and lymph node detection in thoracic images, IEEE Trans Med Imaging, 31: 1061-75, 2012.
Sonka et al., Image Processing, Analysis, and Machine Vision, Cengage Learning, 74-77. 4th ed., 2015. ISBN-13:978-133-59360-7.
Souza A, Udupa JK. Iterative live wire and live snake: New user-steered 3D image segmentation paradigms, Proceedings of SPIE Medical Imaging Conference, 6144: 1159-1165, 2006.
Staib LH, Duncan JS. Boundary Finding with Parametrically Deformable Models. IEEE Transactions on Pattern Analysis and Machine Intelligence 14, 1061-1075, 1992.
Stefan et al., "Localization of anatomical point landmarks in 3D medical images by lifting 3D parametric intensity models". Medical Image Analysis, 10(1), 41-58 (2006).
Stigler S M. Gauss and the Invention of Least Squares. Ann Stat. 1981; 9(3): 465-474.
Sun K, Udupa JK, Odhner D, Tong Y, Zhao L, Torigian DA. Automatic thoracic anatomy segmentation on CT images using hierarchical fuzzy models and registration, Medical Physics, 43(3):1487-1500, doi: 10.1118/1.4942486, 2016.
Sygno-via, Siemens software for disease measurement: http://usa.healthcare.siemens.com/molecular-imaging/pet-ct/syngo-via, 5 pages, 2018.
Tarjan RE. Finding Optimum Branchings, Networks 7: 25-35, 1977.
Tong et al., "Iterative PCA based virtual landmark: a novel automatic landmark identification approach", SPIE Medical Imaging (2017).
Tong T, Wolz R, Wang Z, Gao Q, Misawa K, Fujiwara M, Mori K, Hajnal JV, Rueckert D. Discriminative dictionary learning for abdominal multi-organ segmentation, Medical Image Analysis, 23: 92-104, 2015.
Tong Y, Udupa J K, Torigian D A. Optimization of Abdominal Fat Quantification on CT Imaging Through Use of Standardized Anatomic Space: A Novel Approach. Med Phys. 2014; 41(6): 063501.
Tong Y, Udupa JK, Odhner D, Sin S, Arens R. Abdominal adiposity quantification at MRI via fuzzy model-based anatomy recognition, Proceedings of SPIE Medical Imaging Conference, 8672:86721R-1-86721R-7, 2013.
Tong Y, Udupa JK, Torigian DA, Matsumoto MMS, Sin S, Arens R. Mr image analytics to characterize upper airway architecture in children with OSAS, Proceedings of SPIE Medical Imaging Conference 9417: 94172J-1-94172J-6, 2015.
Tong Yubing, Udupa Jayaram K, Sin Sanghun, Liu Zhenbing, Wileyto Paul E, Torigian Drew A, Arens Raanan. MR image analytics to characterize upper airway structure in obese children with obstructive sleep apnea syndrome, PLOS One, accepted.
Torigian DA, Lopez RF, Alapati S, Bodapati G, Hofheinz F, van den Hoff J, Saboury B, Alavi A, 2011. Feasibility and performance of novel software to quantify metabolically active volumes and 3D partial volume corrected SUV and metabolic volumetric products of spinal bone marrow metastases on 18F-FDG-PEI/CT. Hell J Nucl Med 14(1), 8-14.
Tsechpenakis, G., Chatzis, S.P., 2011. Deformable probability maps: Probabilistic shape and appearance-based object segmentation. Computer Vision and Image Understanding 115, 1157-1169.
Turaga SC, Murray JF, Jain V, Roth F, Helmstaedter M, Briggman K, Denk W, Seung HS. Convolutional networks can learn to generate affinity graphs for image segmentation. Neural Computation 22(2): 511-538, 2010.
Udupa et al., "Body-Wide Hierarchical Fuzzy Modeling, Recognition, and Delineation of Anatomy in Medical Images", Med Image Anal., 2014, 18(5), 752-771.

(56) References Cited

OTHER PUBLICATIONS

Goodpaster B H, Kelley D E, Wing R R, Thaete F L. Effects of Weight Loss on Regional Fat Distribution and Insulin Sensitivity in Obesity. Diabetes. 1999; 48(4): 839-847.
Goodpaster B H, Thaete F L, Kelley D E. Composition of Skeletal Muscle Evaluated with Computed Tomography. Ann Ny Acad Sci. 2000; 904(1): 18-24.
Grand Challenges in Biomedical Image Analysis http://grand-challenge.org/All_Challenges, 2018, 18 pages.
Gratton et al., "Approximate Gauss-Newton Methods for Nonlinear Least Squares Problems", Siam J. Optim, 2007, 18(1), 106-132.
Grevera GJ, Udupa JK, Odhner D, Zhuge Y, Souza A, Iwanaga T, Mishra S. CAVASS: A computer-assisted visualization and analysis software system, Journal of Digital Imaging, 20 (Supplement 1): 101-118. 2007.
Gupta et al., Accuracy of 3D cephalometric measurements based on an automatic knowledge-based landmark detection algorithm, Int. J. Comput. Assist. Radiol. Surg., 11(7), 1297-1309 (2016).
Hansegard J, Urheim S, Lunde K, Rabben SI. Constrained active appearance models for segmentation of triplane echocardiograms. IEEE Transactions on Medical Imaging 26, 1391-1400, 2007.
Heimann et al., Automatic generation of 3D statistical shape models with optimal landmark distributions, Methods Inf. Med., 46(3), 275-281 (2007).
Heimann T, Meinzer HP. Statistical shape models for 3D medical image segmentation: A review. Medical Image Analysis 13, 543-563, 2009.
Hoffman J, Liu J, Turkbey E, Kim L, Summers RM. Automatic identification of IASLC defined lymph node stations on CT scans using multi-atlas organ segmentation, Proceedings of SPIE Medical Imaging Conference, 9414: 94141R-1-94141R-7, 2015.
Hofheinz F, Dittrich S, Potzsch C, Hoff J, 2010. Effects of cold sphere walls in PET phantom measurements on the volume reproducing threshold. Phys Med Biol 55(4), 1099-1113.
Hofheinz F, Poetzsch C, van den Hoff J, 2007. Quantitative 3D ROI delineation in PET: algorithm and validation. J Nucl Med 48 (Supplement 2), 407P. (Abstract only).
Horsfield MA, Bakshi R, Rovaris M, Rocca MA, Dandamudi VSR, Valsasina P, Judica E, Lucchini F, Guttmann CRG, Sormani MP, Filippi M. Incorporating domain knowledge into the fuzzy connectedness framework: Application to brain lesion volume estimation in multiple sclerosis. IEEE Transactions on Medical Imaging 26, 1670-1680, 2007.
Huang L, Udupa JK, Tong Y, Odhner D, Torigian DT. Automatic anatomy recognition on CT images with pathology, Proceedings of SPIE, 9785: 97851S-1-97851S-6, 2016.
Hussein et al., "Automatic Segmentation and Quantification of White and Brown Adipose Tissues from PET/CT Scans", IEEE Trans Med. Imaging, 2017, 36, 734-744.
Jackson A S, Pollock M L, Ward A. Generalized Equations for Predicting Body Density of Women. Med Sci Sport Exer. 1980; 12(3): 175-181.
Jackson A S, Pollock M L. Generalized Equations for Predicting Body Density of Men. Brit J Nutr. 1978; 40(3): 497-504.
Johnson J, Dawson-Hughes B. Precision and Stability of Dual-Energy X-ray Absorptiometry Measurements. Calcified Tissue Int. 1991; 49(3): 174-178.
Jolliffe IT. Principal component analysis, 2nd ed., Springer, New York, 2002.
Juneja et al., "A probabilistic framework for landmark detection based on phonetic features for automatic speech recognition", J. Acoust. Soc. Am., 123(2):1154-1168 (2008).
Juszczyk J, Pietka E, Pyci'nski B. Granular computing in model based abdominal organs detection, Computerized Medical Imaging and Graphics, 46: 121-130, 2015.
Kass M, Witkin A, Terzopoulos D. Snakes: Active Contour Models, International Journal of Computer Vision, 1:321-331, 1987.
Kaufmann A. Introduction to the Theory of Fuzzy Subsets, vol. 1, Fundamental Theoretical Elements. New York, Academic Press Inc.; 1975.
Kobashi S, Udupa, J.K. Fuzzy object models for newborn brain MR image segmentation, Proceedings of SPIE Medical Imaging Conference, 8672: 86720J-1-86720J-6, 2013.
Krizhevsky A, Sutskever I, Hinton GE. Imagenet classificationwith deep convolutional neural networks, in NIPS, 2012.
Kyle U G, Bosaeus I, De Lorenzo A D, et al. Bioelectrical Impedance Analysis—Part I: Review of Principles and Methods. Clin Nutr. 2004; 23(5): 1226-1243.
Kyrou I, Randeva H S, Weickert M O. Clinical Problems Caused by Obesity. In: De Groot L J, Beck-Peccoz P, Chrousos G, et al., editors. Endotext [Internet]. South Dartmouth (MA): MDText.com, Inc. 2000; Available from: http://europepmc.org/books/NBK278973.
Li R, Zhang W, Suk HI, Wang L, Li J, Shen D, Ji S. Deep learning based imaging data completion for improved brain disease diagnosis, MICCAI, Part III, LNCS 8675: 305-312, 2014.
Linguraru MG, Pura JA, Pamulapati V, Summers RM. Statistical 4D graphs for multi-organ abdominal segmentation from multiphase CT. Medical Image Analysis, 16, 904-914, 2012.
Liu H. Two- and Three-Dimensional Boundary Detection, Computer Graphics and Image Processing, 6:123-134, 1977.
Liu J, Hua J, Chellappa V, Petrick N, Sahiner B, Farooqui M, Marti G, Wiestner A, Summers RM. Automatic detection of axillary lymphadenopathy on CT scans of untreated chronic lymphocytic leukemia patients, Proceedings of SPIE Medical Imaging Conference, 8315: 83150B1-1-83150B1-7, 2014.
Liu J, Hua J, Yao J, et al., Computer-aided abdominal lymph node detection using contrast-enhanced CT images, Proceedings of SPIE Medical Imaging Conference, 7963: 7963131-1-7963131-7, 2011.
Liu J, Zhao J, Hoffman J, et al. Mediastinal lymph node detection on thoracic CT scans using spatial prior from multi-atlas label fusion, Proceedings of SPIE Medical Imaging Conference, 9035: 90350M1-1-90350M1-7, 2014.
Liu JM, Udupa JK. Oriented Active Shape Models. IEEE Transactions on Medical Imaging 28, 571-584, 2009.
Liu Y, Udupa JK, Odhner D, Tong Y, Guo S, Attor R, Reincke D, Torigian DA. Definition and automatic anatomy recognition of lymph node zones in the pelvis on CT images, Proceedings of SPIE Medical Imaging Conference, 9788: 97881J-1-97881J-6, 2016.
Lu C, Zheng Y, Birkbeck N, Zhang J, Kohlberger T, Tietjen C, Boettger T, Duncan JS, Zhou SK. Precise segmentation of multiple organs in CT volumes using learning-based approach and information theory. Med Image Comput Comput Assist Interv 15, 462-469, 2012.
Lu K, Higgins W.E. Semi-automatic central-chest lymph-node definition from 3D MDCT images. In: Karssemeijer, N., Summers, R.M. (eds.) SPIE Medical Imaging 2010: Computer-Aided Diagnosis, vol. 7624 (2010).
Lu K, Higgins WE. Segmentation of the central-chest lymph nodes in 3D MDCT images, Computers in Biology and Medicine, 41 (9): 780-789, 2011.
Malladi R, Sethian J, Vemuri B. Shape Modeling with Front Propagation: A Level Set Approach, IEEE Transactions on Pattern Analysis and Machine Intelligence, 17:158-175, 1995.
Martin et al., Neural Network Design, 2nd Edition, eBook, (2014).
Martin L, Birdsell L, Macdonald N, et al. Cancer Cachexia in the Age of Obesity: Skeletal Muscle Depletion is A Powerful Prognostic Factor, Independent of Body Mass Index. J Clin Oncol. 2013; 31(12): 1539-1547.
Martínez-Martínez F, Kybic J, Lambert L, Mecková Z. Fully Automated Classification of Bone Marrow Infiltration in Low-Dose CT of Patients with Multiple Myeloma Based on Probabilistic Density Model and Supervised Learning. Comput Biol Med. 2016; 71(C): 57-66.
Matsumoto MMS, Beig N, Udupa JK, Archer S, Torigian DA. Automatic localization of IASLC-defined mediastinal lymph node stations on CT images using fuzzy models, Proceedings of SPIE 9035: 90350J-1-90350J-7, 2014.
Matsumoto MMS, Udupa JK. Optimal hierarchies for fuzzy object models, Proceedings of SPIE Medical Imaging Conference, 8671:86712C-1-86712C-7, 2013.

(56) References Cited

OTHER PUBLICATIONS

Matsumoto MSM, Udupa JK, Saboury B, Torigian DA. Quantitative normal thoracic anatomy at CT, Computerized Medical Imaging and Graphics, to appear.

Mattsson S, Thomas B J. Development of Methods for Body Composition Studies. Phys Med 30 Biol 2006; 51(13): 203-228.

Maurovich-Horvat P, Massaro J, Fox C S, Moselewski F, O'Donnell C J, Hoffmann U. Comparison of Anthropometric, Area- and Volume-Based Assessment of Abdominal Subcutaneous and Visceral Adipose Tissue Volumes Using Multi-Detector Computed Tomography. Int J Obesity. 2007; 31(3): 500-506.

McGraw KO, Wong, SP. 1996a. Forming inferences about some intra-class correlation coefficients. Psychological Methods 1: 30-46, 1996. Forming inferences about some intra-class correlation coefficients: Correction. Psychological Methods 1:390, 1996.

Meyer C, Peters J, Weese J. Fully automatic segmentation of complex organ systems: Example of trachea, esophagus and heart segmentation in CT images, SPIE Medical Imaging. SPIE, pp. 796216-796211-796216-796211, 2011.

Mumford D, Shah J. Optimal Approximations by Piecewise Smooth Functions and Associated Variational Problems, Communications of Pure and Applied Mathematics, 42:577-685, 1989.

A predictive model for aggressive non-Hodgkin's lymphoma. The International Non-Hodgkin's Lymphoma Prognostic Factors Project. N Engl J Med. Sep. 30, 1993;329(14):987-94. PubMed PMID: 8141877.

About BD2k, National Institute of Health, 2019, https://datascience.nih.gov/bd2k/about, 2 pages.

ADNI: Alzheimer's Disease Neuroimaging Initiative http://adni.loni.usc.edu/.

Alizadeh AA, Eisen MB, Davis RE, Ma C, Lossos IS, Rosenwald A, Boldrick JC, Sabet H, Tran T, Yu X, Powell JI, Yang L, Marti GE, Moore T, Hudson J Jr, Lu L, Lewis DB, Tibshirani R, Sherlock G, Chan WC, Greiner TC, Weisenburger DD, Armitage JO, Warnke R, Levy R, Wilson W, Grever MR, Byrd JC, Botstein D, Brown PO, Staudt LM. Distinct types of diffuse large B-cell lymphoma identified by gene expression profiling. Nature. Feb. 3, 2000;403(6769):503-11. PubMed PMID: 10676951.

Anderson P J, Chan J C, Chan Y L, et al. Visceral Fat and Cardiovascular Risk Factors in Chinese NIDDM Patients. Diabetes Care. 1997; 20(20): 1854-1858.

Antoun S. Sarcopenia Is Linked to Treatment Toxicity in Patients with Metastatic Colorectal Cancer. Nutr Cancer. 2014; 66(4): 583-589.

Armato III SG, McLennan G, et al. The Lung Image Database Consortium (LIDC) and Image Database Resource Initiative (IDRI): A completed reference database of lung nodules on CT scans, Medical Physics, 38: 915-931, 2011; doi: 10.1118/1.3528204.

Ashburner J, Friston KJ. Computing average shaped tissue probability templates. Neuroimage 45, 333-341, 2009.

Baiker M, Milles J, Dijkstra J, Henning TD, Weber AW, Que I, Kaijzel EL, Lowik CW.G.M, Reiber JHC, Lelieveldt BPF. Atlas-based whole-body segmentation of mice from low-contrast Micro-CT data. Medical Image Analysis 14, 723-737, 2010.

Baracos V E, Reiman T, Mourtzakis M, Gioulbasanis I, Antoun S. Body Composition in Patients with Non-Small Cell Lung Cancer: A Contemporary View of Cancer Cachexia with the Use of Computed Tomography Image Analysis. Am J Clin Nutr. 2010; 91(4): 1133S-1137S.

Beucher S. The Watershed Transformation Applied to Image Segmentation, 10th Pfefferkorn Conference on Signal and Image Processing in Microscopy and Microanalysis, pp. 299-314, 1992.

Bezdek J, Hall L, Clarke L. Review of MR Image Segmentation Techniques Using Pattern Recognition, Medical Physics, 20:1033-1048, 1993.

Bogovic, J.A., Prince, J.L., Bazin, P.L., 2013. A multiple object geometric deformable model for image segmentation. Computer Vision and Image Understanding 117, 145-157.

Boykov Y, Veksler O, Zabih R. Fast Approximate Energy Minimization via Graph Cuts, IEEE Transactions on Pattern Analysis and Machine Intelligence, 23:1222-1239, 2001.

Britton K A, Massaro J M, Murabito J M, Kreger B E, Hoffmann U, Fox C S. Body Fat Distribution, Incident Cardiovascular Disease, Cancer, and All—Cause Mortality. J Am Coll Cardiol. 2013; 62(10): 921-925.

Cabezas M, Oliver A, Llado X, Freixenet J, Cuadra MB. A review of atlas-based segmentation for magnetic resonance brain images. Comput Methods Programs Biomed 104, 158-177, 2011.

Cerrolaza JJ, Villanueva A, Cabeza R. Hierarchical Statistical Shape Models of Multiobject Anatomical Structures: Application to Brain MRI, IEEE Transactions on Medical Imaging, 31(3): 713-724, 2012.

Chan T. Computerized Method for Automatic Evaluation of Lean Body Mass from PET/CT: Comparison with Predictive Equations. J Nucl Med. 2012; 53(1): 130-137.

Chen XJ, Bagci U. 3D automatic anatomy segmentation based on iterative graph-cut-ASM. Medical Physics 38, 4610-4622, 2011.

Chen XJ, Udupa JK, Bagci U, Zhuge Y, Yao J. Medical image segmentation by combining graph cut and oriented active appearance models, IEEE Transactions on Image Processing 21(4), 2035-2046, 2012.

Cheng et al., "Automatic Dent-landmark detection in 3-D CBCT dental volumes", Conf. Proc. IEEE Eng. Med. Biol. Soc., 6204-6207 (2011).

Cherry KM, Wang S, Turkbey EB, Summers RM. Abdominal lymphadenopathy detection using random forest, Proceedings of SPIE Medical Imaging Conference, 9035: 90351G1-1-90351G1-6, 2014.

Cheson BD, Fisher RI, Barrington SF, Cavalli F, Schwartz LH, Zucca E, Lister AT. Recommendations for Initial Evaluation, Staging, and Response Assessment of Hodgkin and Non-Hodgkin Lymphoma: The Lugano Classification, Journal of Clinical Oncology, 32 (27): 3059-3067, 2014.

Christensen G, Rabbitt R, Miller M. 3-D Brain Mapping Using a Deformable Neuroanatomy, Physics in Medicine and Biology, 39:609-618, 1994.

Chu C, Oda M, Kitasaka T, Misawa K, Fujiwara M, Hayashi Y, Wolz R, Rueckert D, Mori K. Multi-organ segmentation from 3D abdominal CT images using patient-specific weighted-probabilistic atlas, SPIE Medical Imaging. SPIE, pp. 86693Y-86691-86693Y-86697, 2013.

Ciesielski KC, Udupa JK, 2010. Affinity functions in fuzzy connectedness based image segmentation II: Defining and recognizing truly novel affinities. Computer Vision and Image Understanding 114, 155-166.

Ciesielski KC, Udupa JK, Falcao AX, and deMiranda PAV, 2012. Fuzzy connectedness image segmentation in graph cut formulation: A linear-time algorithm and a comparative analysis. Journal of Mathematical Imaging and Vision 44, 375-398.

Ciresan DC, Giusti A, Gambardella LM, Schmidhuber J. Mitosis detection in breast cancer histology images with deep neural networks. In: Mori, K., Sakuma, I., Sato, Y., Barillot, C., Navab, N. (eds.) MICCAI 2013, Part II. LNCS 8150: 411-418, 2013.

Clark K, Vendt B, Smith K, Freymann J, Kirby J, Koppel P, Moore S, Phillips S, Maffitt D, Pringle M, Tarbox L, Prior F. The Cancer Imaging Archive (TCIA): Maintaining and Operating a Public Information Repository, Journal of Digital Imaging, 26 (6): 1045-1057. 2013.

Clark W, Siegel E M, Chen Y A, et al. Quantitative Measures of Visceral Adiposity and Body Mass Index in Predicting Rectal Cancer Outcomes After Neoadjuvant chemoradiation. J Am Coll Surgeons. 2013; 216(6): 1070-1081.

Cootes T, Taylor C, Cooper D. Active Shape Models: Their Training and Application, Computer Vision and Image Understanding, 61:38-59, 1995.

Cormen TH, Leiserson CE, Rivest RL, Stein C. Introduction to Algorithms, The MIT Press, Cambridge, 3rd ed., 2009.

Criminisi A, Robertson D, Konukoglu E, Shotton J, Pathak S, White S, Siddiqui K, Regression forests for efficient anatomy detection and localization in computed tomography scans. Med Image Anal 17, 1293-1303, 2013.

(56) References Cited

OTHER PUBLICATIONS

Criminisi et al., "Decision forests with long-range spatial context for organ localization in CT volumes", In MICCAI Workshop on Probabilistic Models for Medical Image Analysis(2009).

Czernichow S, Kengne A P, Stamatakis E, Hamer M, Batty G D. Body Mass Index, Waist Circumference and Waist-Hip Ratio: Which is The Better Discriminator of Cardiovascular Disease Mortality Risk? Evidence from an Individual-Participant Meta-Analysis of 82864 Participants from Nine Cohort Studies. Obes Rev. 2011; 12(9): 680-687.

Di S K, Mourtzakis M. A Critical Evaluation of Body Composition Modalities Used to Assess Adipose and Skeletal Muscle Tissue in Cancer. Appl Physiol Nutr Me. 2012; 37(5): 811-821.

Diaz A A, Zhou L, Young T P, et al. Chest CT Measures of Muscle and Adipose Tissue in COPD: Gender-based Differences in Content and in Relationships with Blood Biomarkers. Acad Radiol. 2014; 21(10): 1255-1261.

Dong C, Chen YW, Lin L, Hu H, Jin C, Yu H, Han XH, Tateyama T. Simultaneous segmentation of multiple organs using Random Walks, Journal of Information Processing, 24: 320-329, 2016.

Donner R, Menze BH, Bischof H, Langs G. Global localization of 3D anatomical structures by pre-filtered Hough Forests and discrete optimization, Medical Image Analysis, 17: 1304-1314, 2013.

Dornheim J, Seim H, Preim B, Hertel I, Strauß G. Segmentation of neck lymph nodes in ct datasets with sTable 3d mass-spring models. In: MICCAI (2), Lecture Notes in Computer Science, LNCS 4191, Copenhagen, Denmark, pp. 904-911, 2006.

Doyle W. Operations useful for similarity-invariant pattern recognition, Journal of the ACM, 9:259-267, 1962.

Elattar et al., "Automatic aortic root landmark detection in CTA images for preprocedural planning of transcatheter aortic valve implantation", Int. J. Cardiovasc. Imaging, 32(3), 501-511 (2016).

Erbil Y, Barbaros U, Sari S, Agcaoglu O, Salmaslioglu A, Ozarmagan S. The Effect of Retroperitoneal Fat Mass on Surgical Outcomes in Patients Performing Laparoscopic Adrenalectomy: the Effect of Fat Tissue in Adrenalectomy. Surg Innov. 2010; 17(2): 114-119.

Falcao A, Udupa JK, Miyazawa FK. An ultra-fast user-steered image segmentation paradigm: Live-wire-on-the-fly, IEEE Transactions on Medical Imaging, 19(1): 55-62, 2000.

Falcao A, Udupa JK, Samarasekera S, Sharma S, Hirsch BE, Lotufo R. User-Steered Image Segmentation Paradigms: Live Wire and Live Lane, Graphical Models and Image Processing, 60:233-260, 1998.

Feuerstein M, Glocker B, Kitasaka T, Nakamura Y, Iwano S, Mori K. Mediastinal atlas creation from 3-D chest computed tomography images: application to automated detection and station mapping of lymph nodes, Medical Image Anal, 16: 63-74, 2012.

Fouladiun M, Körner U, Bosaeus I, Daneryd P, Hyltander A, Lundholm K G. Body Composition and Time Course Changes in Regional Distribution 577 of Fat and Lean Tissue in Unselected Cancer Patients on Palliative Care—Correlations with Food Intake, Metabolism, Exercise Capacity, and Hormones. Cancer. 2005; 103(10): 2189-2198.

Fox C S, Massaro J M, Hoffmann U, et al. Abdominal Visceral and Subcutaneous Adipose Tissue Compartments: Association with Metabolic Risk Factors in the Framingham Heart Study. Circulation. 2007; 116(1): 39-48.

Gee J, Reivich M, Bajcsy R. Elastically Deforming 3D Atlas to Match Anatomical Brain Images, Journal of Computer Assisted Tomography, 17:225-236, 1993.

Gibson D J, Burden S T, Strauss B J, Todd C, Lal S. The Role of Computed Tomography in Evaluating Body Composition and the Influence of Reduced Muscle Mass on Clinical Outcome in Abdominal Malignancy: A Systematic Review. Eur J Clin Nutr. 2015; 69(10): 1079-1086.

Udupa JK, LeBlanc VR, Zhuge Y, Imielinska C, Schmidt H, Currie LM, Hirsch BE, Woodburn J. A framework for evaluating image segmentation algorithms, Computerized Medical Imaging and Graphics, 30(2):75-87, 2006.

Udupa JK, Saha PK, Lotufo RA, 2002. Relative fuzzy connectedness and object definition: Theory, algorithms, and applications in image segmentation IEEE Transactions on Pattern Analysis and Machine Intelligence 24, 1485-1500.

Udupa JK, Samarasekera S. Fuzzy Connectedness and Object Definition: Theory, Algorithms, and Applications in Image Segmentation, Graphical Models and Image Processing, 58:246-261, 1996.

Vaclav et al., "Personalized Graphical Models for Anatomical Landmark Localization in Whole-Body Medical Images", International Journal of Computer Vision, 111(1),29-49(2015).

Van der Lijn F, de Bruijne M, Klein S, den Heijer T, Hoogendam YY, van der Lugt A, Breteler MMB, Niessen WJ. Automated Brain Structure Segmentation Based on Atlas Registration and Appearance Models. IEEE Transactions on Medical Imaging 31, 276-286, 2012.

Viallon V, Latouche A. Discrimination measures for survival outcomes: connection between the AUC and the predictiveness curve. Biometrical Journal. Biometrische Zeitschrift, 53(2), 217-236, 2011. http://doi.org/10.1002/bimj.201000153.

Wang et al., "Automatic anatomy recognition in whole-body PET/CT images", Medical Physics, 2016, 43(1), 613-629.

Wang Z, Salah MB, Gu B, Islam A, Goela A, Li S. Direct estimation of cardiac biventricular volume with an adapted Bayesian formulation, IEEE Transactions on Biomedical Engineering, 61 (4):1251-1260, 2014.

Wu Z, Leahy R. An optimal graph-theoretic approach to data clustering: theory and its application to image segmentation, IEEE Transactions on Pattern Analysis and Machine Intelligence, 15(11): 1101-1113, 1993.

Yang S, Weidong C, Heng H, Xiaogang W, Yun Z, Fulham MJ. Lesion detection and characterization with context driven approximation in thoracic FDG PET-CT images of NSCLC studies, IEEE Trans Med Imaging, 33: 408-21, 2014.

Zhao L, Udupa JK, Odhner D, Tong Y, Wang H, Torigian DA. Automatic anatomy recognition of sparse objects, Proceedings of SPIE 9413: 94133N-1-94133N-8, 2015.

Zhen X, Wang Z, Islam A, Bhaduri M, Chan I, Li S. Multi-Scale deep networks and regression forests for direct bi-ventricular volume estimation, Medical Image Analysis, 30: 120-129, 2016.

Zheng et al., Automatic aorta segmentation and valve landmark detection in C-arm CT for transcatheter aortic valve implantation, IEEE Trans. Med. Imaging, 31(12), 2307-2321 (2012).

Zhou J, Rajapakse JC. Segmentation of subcortical brain structures using fuzzy templates. NeuroImage 28, 915-924, 2005.

Ziepert M, Hasenclever D, Kuhnt E, Glass B, Schmitz N, Pfreundschuh M, Loeffler M. Standard International prognostic index remains a valid predictor of outcome for patients with aggressive CD20+ B-cell lymphoma in the rituximab era. J Clin Oncol. May 10, 2010;28(14):2373-80. doi: 10.1200/JCO.2009.26.2493. Epub Apr. 12, 2010. Erratum in: J Clin Oncol. Feb. 20, 2011;29(6):779. PubMed PMID: 20385988.

\* cited by examiner

QUANTIFICATION AND STAGING OF BODY-WIDE TISSUE COMPOSITION AND OF ABNORMAL STATES ON MEDICAL IMAGES VIA AUTOMATIC ANATOMY RECOGNITION

CROSS REFERENCE TO RELATED APPLICATIONS

This application claims priority to U.S. Provisional Patent Application No. 62/628,943, filed Feb. 10, 2018, the entirety of which is incorporated by reference herein.

TECHNICAL FIELD

The disclosure relates to applications utilizing a method for analyzing areas of the anatomy that is independent of imaging modality and that uses automatic anatomy recognition to identify all organs within a particular body segment, such as the thorax, abdomen, pelvis, and neck. Applications include methods for quantifying body tissue components including subcutaneous adipose tissue (SAT), visceral adipose tissue (VAT), muscle tissue, and bone tissue. More particularly, the disclosure includes methods for recognizing, staging, and quantifying disease within body tissue components including sub-organ tissue components, organs, organ systems, body regions, and the whole body. Even more particularly, the disclosure relates to virtual landmarks, and using the same for localizing anatomical body regions.

BACKGROUND

Assessment of body composition is important for various clinical and research applications including evaluation of the effects of obesity upon comorbid disease development, prognosis, and treatment outcome and assessment of gender-based or age-based differences of body composition in health and disease. An efficient and accurate technique for quantification of body tissue components including subcutaneous adipose tissue (SAT), visceral adipose tissue (VAT), muscle tissue, and bone tissue is needed to perform such assessments practically.

There are many methods available for body composition assessment. Anthropometry is a non-invasive method which is easy to perform. Body mass index (BMI), skin fold thickness waist circumference, hip circumference, and waist-to-hip ratio are the most common anthropometric measures used to assess obesity. However, these methods are based on the assumption that SAT has a constant relationship with whole-body adipose tissue. This assumption results in inaccuracy in the assessment of VAT and measurement of adipose tissue in pathologic states. Even if the assumption is valid, it can achieve only rough estimation result. Bioelectrical impedance analysis (BIA) is an often-used method for estimating body composition, and in particular body fat. It is another non-invasive method with better accuracy than the anthropometry methods in healthy populations. However, it assumes that the human body is a cylinder with equal conductance as well as stable hydration status, which may not be the case in patients with advanced disease conditions. Consequently, BIA cannot overcome the influences of variations in different subjects that can lead to inaccurate measurement of body composition. Air displacement plethysmography (ADP) is also a non-invasive method based on the same principles as the reference standard method of hydrostatic weighing. Although ADP is a recognized and scientifically validated densitometry method to measure human body composition, it still has some drawbacks. It has a strict requirement for the subject to fully exhale, which may be difficult to achieve in children and in patients with lung disease. ADP also cannot quantify the individual VAT and SAT components, let alone the individual non-fatty tissue components.

None of the above methods permit accurate regional quantification of the body composition, and the fat quantification results may be unrelated to the amount of VAT. Radiologic imaging techniques make the visualization and spatial localization of human internal structures possible, affording the potential for improving quantification accuracy. Dual-energy X-ray absorptiometry (DXA) is a reference standard method in body composition quantification because of its high precision and high stability for measurement. However, DXA has a limited ability to distinguish between different compartments such as VAT and SAT. Moreover, DXA is unnecessary for most disease conditions and requires additional radiation exposure if applied for body composition quantification. Unlike DXA, magnetic resonance imaging (MRI) and computed tomography (CT) images are routinely acquired in many clinical situations, and thus can be utilized to quantify body composition with little added healthcare cost. MRI can measure the quantity and distribution of body composition in the whole body without exposure to ionizing radiation, which makes it an ideal method for whole-body composition analysis. Yet, as it is more expensive, slower in image acquisition time, and less widely available compared to CT, it has a more limited role in body-wide composition quantification. Moreover, it poses serious challenges to quantify bone tissues since these tissues do not yield adequate MRI signals, and it becomes difficult to distinguish them from other hard connective tissues such as ligaments and tendons. CT is widely used in body composition quantification because it is easy to perform, has a short image acquisition time, and provides accurate, high-quality information on point-wise tissue composition in the body. However, diagnostic CT is performed to scan only specific body regions depending on the clinical indication. Given its associated radiation dose, whole-body information is often not obtained and fully assessed. In any case, the methods of this application are applicable to such images as well if composition is sought only for that specific body region.

Until now, most body composition analysis methods based on CT have used single or multiple slices to estimate the whole-body volume in any given individual. Some investigators use the third lumbar vertebral region (L3) for analysis; others believe that the L4-L5 level is the best choice, and some others focus on using the slice or slices most correlated to whole-body volume. Although use of a handful of slices may have strong correlation with the whole-body volume, use of these slices alone cannot accurately quantify body composition, since the distributions of body composition in different subjects are generally different. There are also approaches to assess body composition based on a threshold method as well as via manual operation. However, the accuracy of thresholding is poor, and the manual operation method is labor-intensive, error-prone, and impractical when applied to the whole body or to a large number of imaging studies.

Positron emission tomography (PET)/computed tomography (CT), or PET/CT, provides co-registered molecular and anatomic images in a single imaging session, and is the most frequently used method for clinical molecular imaging assessment of patients with various disease conditions, most notably cancer. The low-dose CT technique in PET/CT allows for a reduced radiation exposure, which facilitates whole-body CT imaging. Therefore, considering the above drawbacks of single-slice and body-region methods and the lack of availability of body-wide images, low-dose CT is an attractive modality for performing body composition analysis in certain disease conditions. Body composition analysis works based on low-dose CT images are very few, and they are all limited in the level of automation achieved, the extent of body region covered, and the type of tissues considered. Pak manually outlines volume of interest around the abdominal muscular wall and then uses thresholds to separate VAT on CT images. Pak K, Lee S H, Lee J G, Seok J W, Kim I J. Comparison of Visceral Fat Measures with Cardiometabolic Risk Factors in Healthy Adults. *Plos One.* 2016; 11(4): 1-10. Oliveira calculates VAT and SAT volumes from L1 through L5 using semi-automated tracings. Oliveira A L, Azevedo D C, Bredella M A, Stanley T L, Torriani M. Visceral and Subcutaneous Adipose Tissue FDG Uptake by PET/CT in Metabolically Healthy Obese Subjects. *Obesity.* 2015; 23(2): 286-289. The above two methods need manual interaction on image slices of each target subject. Chan presents a method which uses thresholds to evaluate the volume of lean body mass. Chan T. Computerized Method for Automatic Evaluation of Lean Body Mass from PET/CT: Comparison with Predictive Equations. *J Nucl Med.* 2012; 53(1): 130-137. However, the method is not tested on adipose tissues yet, let alone for separately quantifying VAT and SAT.

Currently, body-wide positron emission tomography (PET) is the most commonly used modality for molecular imaging of patients with cancer, and is also utilized to assess patients with a wide variety of inflammatory disease conditions. PET imaging, whether via positron emission tomography/computed tomography (PET/CT) or positron emission tomography/magnetic resonance imaging (PET/MRI), improves the sensitivity for detection of pathology at the molecular, subcellular, or cellular level well before gross anatomic changes manifest, and simultaneously improves the specificity of diagnosis to distinguish whether macroscopic abnormalities are benign or malignant in nature. As such, it changes management in up to 40% of patients with cancer prior to implementation of treatment, often due to improved detection of regional lymph node metastases and distant metastases in the body, and improves the diagnostic performance of post-treatment assessment compared to structural imaging with CT or MRI alone. Importantly, PET provides image data that are quantifiable prior to and following treatment, allowing for individualized regional and global disease assessment of patients with cancer and other non-neoplastic disease conditions.

The primary clinical tasks for which imaging is used currently for managing cancer patients are: screening, detection/diagnosis, staging, prognosis assessment, treatment planning and guidance, treatment prediction assessment, treatment response assessment, and restaging/surveillance. Images are currently employed for most of these tasks mainly in a qualitative mode. This is mainly because of the lack of techniques to reliably localize and delineate objects and pathological regions in objects on body-wide PET/CT or PET/MR images in a highly automated manner. Several commercial vendors currently offer software for disease measurement. They all operate under the paradigm of first manually performing recognition of diseased tissue regions by manually specifying a region of interest, subsequently automatically delineating tumors within this region by making use of information from PET alone or from both PET and CT/MRI, and finally measuring disease burden in the form of tumor volume and PET standardized uptake value (SUV) statistics within the tumor region. Such manual methods of quantification are error-prone, are subject to intra- and inter-observer variations, are labor intensive, body-wide measurement is very difficult, and result in suboptimal throughput in clinical practice. The ability to routinely quantify disease body-wide in a production mode can potentially improve many of the above clinical tasks significantly. The same paradigm also holds true in patients with non-neoplastic disease conditions.

SUMMARY

Given the challenges introduced by the suboptimal quality of these images and the limitations of manual methods of segmentation including time-inefficiency, labor-intensiveness, and suboptimal accuracy and reproducibility, our goal in one aspect of this disclosure is to develop a method of body composition analysis from these images which are obtained as part of routine clinical PET/CT acquisition. Our approach adapts and extends a recently developed methodology called Automatic Anatomy Recognition (AAR), which is a framework for the localization (called recognition) and delineation of multitudes of objects body-wide on CT, PET/CT, and MR images. Although our focus in body composition analysis is not on multitudes of objects, we will exploit AAR's ability to accurately localize objects for supporting our methods for delineating the tissue components of interest.

In exemplary embodiments, we will focus on the body torso (BT), defined to be the union of the thoracic, abdominal, and pelvic body regions. (Although the data shown here currently apply to more limited body regions on PET and CT, the same concepts apply body wide as well as to MR images.) One non-limiting objective is to quantify four tissue components in BT—SAT, VAT, bone tissue, and muscle tissue—from CT images of given whole-body PET/CT acquisitions. One method, referred to as AAR-BCA (BCA for body composition analysis) may comprise three steps—modeling BT with its ensemble of key objects from a population of patient images, recognition or localization of these objects in a given patient image I, and delineation and quantification of the four tissue components in I guided by the recognized objects. In the first step, a set of objects is first identified. The objects include anatomic organs, tissue regions, and tissue interfaces. The latter are expressly formulated to facilitate the precise delineation of the four tissue components of our focus in BT. Modeling follows the principles of AAR of first precisely defining the anatomic extent of each object, generating binary delineations of the objects in the given image population following the definitions, determining the hierarchical order in which the objects should be arranged, and constructing a fuzzy anatomy model of the object ensemble following the hierarchy. The second step involves recognizing, or finding roughly the location of, each object in any given whole-body image I of a patient following the object hierarchy and guided by the built model. The third step makes use of this fuzzy localization information of the objects and the intensity distributions of the four tissue components, already learned and encoded in the model, to optimally delineate and quantify these components.

In another aspect of the disclosure, we extend the previous automatic anatomy recognition (AAR) methodology further to foster body-wide disease quantification (DQ). Such a methodology may be referred to as AAR-DQ and may comprise three steps: (1) Building a fuzzy anatomy model of the body torso along with all its major anatomic objects from existing patient PET/CT images. (2) Using the already built model to automatically recognize/locate each object in a given cancer patient's PET/CT or PET/MR image. (3) To automatically quantify abnormal states such as disease burden and other properties within each located object by making use of the disease information in the PET image without explicitly delineating either the object or the pathological region within it. Using commercially available clinically used software for manual disease measurement as reference, our studies indicate that AAR-DQ can measure total disease burden within 2% of the reference measurement on images of standard PET phantoms and within about 6% on patient PET/CT images. Please note that this methodology applies to body-wide disease quantification on PET imaging, whether acquired as part of PET/CT or PET/MR imaging, and applies to PET imaging obtained following administration of 18F-fluorodeoxyglucose (FDG) or any other radiotracer.

The AAR-DQ approach may comprise at least the following unique features: (1) It decouples dependence on explicit segmentation (delineation) of the organ and diseased tissue regions and performs DQ directly from object location information found automatically. This makes the disease quantification process robust, efficient, and practical. (2) It takes a fuzzy approach for handling uncertainties for object modeling, object recognition, disease mapping, and disease quantification, which obviates the need for explicitly correcting for phenomena such as the partial volume effect. (3) By the characteristics of the AAR approach, AAR-DQ is not tied to any specific object, and hence is applicable body-wide. Different or other features may be exhibited using AAR-DQ or other methodologies of the present disclosure.

In yet another aspect of the disclosure, virtual landmarks are proposed and may reside inside, on the boundary of, or outside the object and are tethered to the object. Our solution is straightforward, simple, and recursive in nature, proceeding from global features initially to local features in later levels to detect landmarks. Principal component analysis (PCA) is used as an engine to recursively subdivide the object region. The object itself may be represented in binary or fuzzy form or with gray values. The method is illustrated in 3D space (although it generalizes readily to spaces of any dimensionality) on four objects (liver, trachea and bronchi, and outer boundaries of left and right lungs along pleura) derived from 5 patient computed tomography (CT) image data sets of the thorax and abdomen. The virtual landmark identification approach seems to work well on different structures in different subjects and seems to detect landmarks that are homologously located in different samples of the same object. The approach guarantees that virtual landmarks are invariant to translation, scaling, and rotation of the object/image. Landmarking techniques are fundamental for many computer vision and image processing applications, and we are currently exploring the use of virtual landmarks in automatic anatomy recognition and object analytics.

In yet another aspect of the disclosure, a method first selects a (set of) reference object(s), segments it (them) roughly, and identifies virtual landmarks for the object(s). The geometric relationship between these landmarks and the boundary locations of body regions in the cranio-caudal direction is then learned through a neural network regressor, and the locations are predicted. Based on low-dose unenhanced CT images of 180 near whole-body PET/CT scans (which includes 34 whole-body PET/CT scans), the mean localization error for the boundaries of superior of thorax (TS) and inferior of thorax (TI), expressed as number of slices (slice spacing≈4 mm), and using either the skeleton or the pleural spaces as reference objects, is found to be 3, 2 (using skeleton) and 3, 5 (using pleural spaces), respectively, or in mm 13, 10 mm (using skeleton) and 10.5, 20 mm (using pleural spaces), respectively. Improvements of this performance via optimal selection of objects and virtual landmarks and other object analytics applications are currently being pursued.

The scope of the invention also includes a system including a processor that executes stored instructions for executing the steps of the method. The above and other characteristic features of the invention will be apparent from the following detailed description of the invention.

DETAILED DESCRIPTION OF ILLUSTRATIVE EMBODIMENTS

Figure 1:
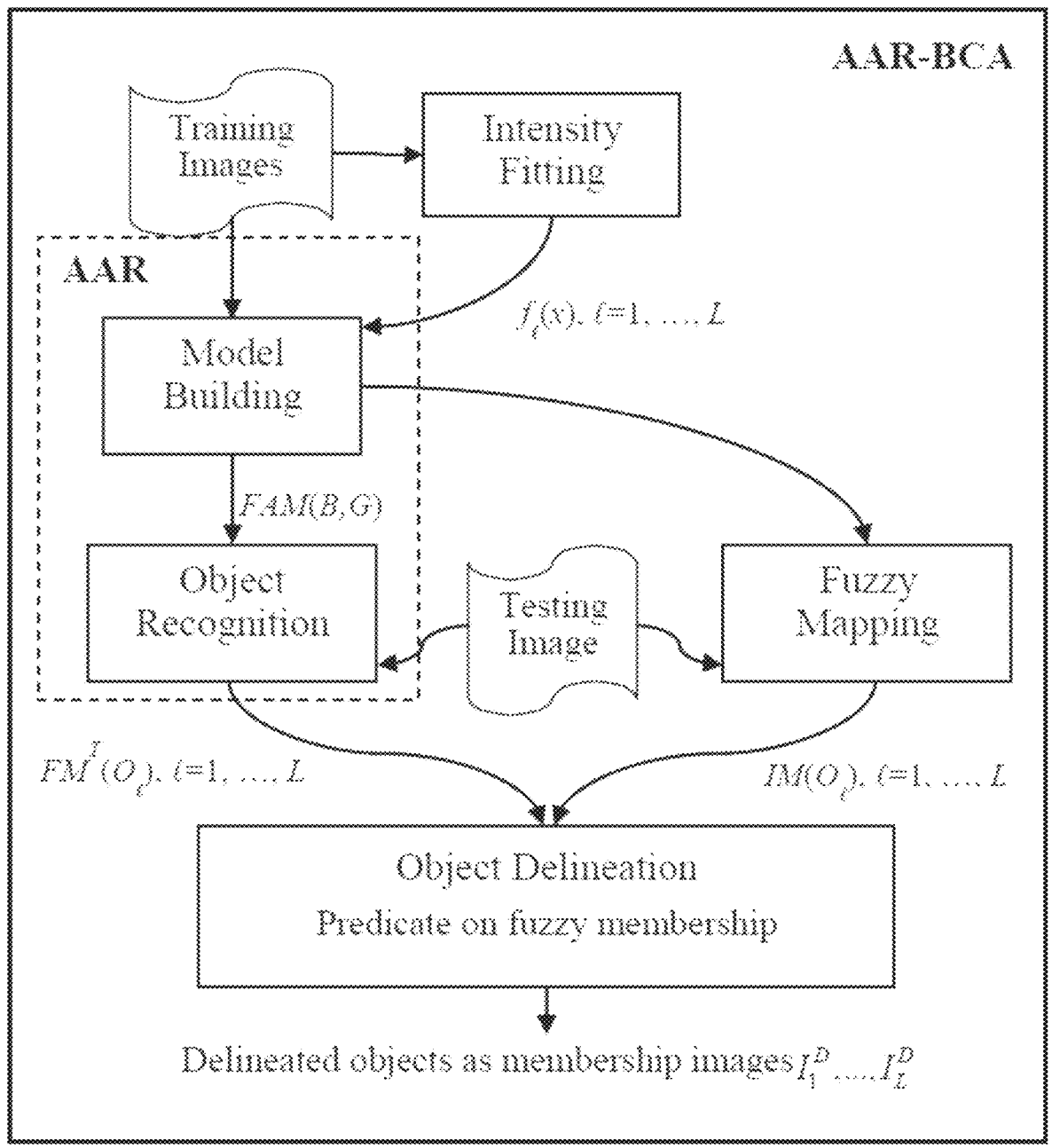
FIG. 1 illustrates schematic representation of the AAR-BCA approach.

Certain well-known details are not set forth in the following disclosure, however, to avoid unnecessarily obscuring the various embodiments of the invention. Those of ordinary skill in the relevant art will understand that they can practice other embodiments of the invention without one or more of the details described below. Also, while various methods are described with reference to steps and sequences in the following disclosure, the description is intended to provide a clear implementation of embodiments of the invention, and the steps and sequences of steps should not be taken as required to practice the invention.

In one aspect of the present disclosure, a method, referred to as automatic anatomy recognition body composition analysis (AAR-BCA), may be used to quantify at least four tissue components in body torso (BT)—subcutaneous adipose tissue (SAT), visceral adipose tissue (VAT), bone tissue, and muscle tissue—from CT images of given whole-body PET/CT acquisitions. AAR-BCA consists of three key steps—modeling BT with its ensemble of key objects from a population of patient images, recognition or localization of these objects in a given patient image I, and delineation and quantification of the four tissue components in I guided by the recognized objects. In the first step, from a given set of patient images and the associated delineated objects, a fuzzy anatomy model of the key object ensemble, including anatomic organs, tissue regions, and tissue interfaces, is built where the objects are organized in a hierarchical order. The second step involves recognizing, or finding roughly the location of, each object in any given whole-body image I of a patient following the object hierarchy and guided by the built model. The third step makes use of this fuzzy localization information of the objects and the intensity distributions of the four tissue components, already learned and encoded in the model, to optimally delineate in a fuzzy manner and quantify these components. All parameters in the AAR-BCA method are determined from training data sets.

In a non-limiting example, 25 low-dose CT images from different subjects were tested in a 5-fold cross validation strategy for evaluating AAR-BCA with a 15-10 train-test data division. For BT, over all objects, AAR-BCA achieves a false positive volume fraction (FPVF) of 3.6% and false negative volume fraction (FNVF) of 4.2%. Notably, SAT and bone tissue both achieve a FPVF under 4% and a FNVF under 3%. For muscle tissue, the FNVF of 6.4% is higher than for other objects and so also for VAT (4.4%). The level of accuracy for the four tissue components in individual body sub-regions mostly remains at the same level as for BT. The processing time required per patient image is under a minute.

Motivated by applications in cancer and other non-neoplastic systemic diseases, one non-limiting objective described in this disclosure is a practical method for body composition quantification which is automated, accurate, and efficient, and works on BT in low dose CT. The proposed AAR-BCA method towards this goal can quantify four tissue components including SAT, VAT, bone tissue, and muscle tissue in the body torso with about 5% overall error. All needed parameters can be automatically estimated from the training data sets.

Once object recognition is performed, we know roughly the region occupied by the object in the image. In the AAR approach, this information is subsequently used for the detailed and precise delineation of the object boundary. In many situations, although object recognition can be performed well, object delineation poses challenges due to image artifacts, absence of adequate boundary contrast in the image, etc.

In another aspect of the present disclosure, the above process may be stopped/transitioned after the recognition step and directly proceed to disease quantification. The recognition step provides us fuzzy information about the object's whereabouts. Relying only on this information, we then proceed to disease quantification without delineating the object.

Disease quantification may be performed within the object by computing a fuzzy disease map inside the object that indicates pixel-by-pixel the disease severity. In this manner, we bypass the need to delineate the pathological region as well in a binary manner. Note that the clinical software systems mentioned above perform disease measurement by explicitly delineating the pathological region. This approach works fine on well-defined, focal, and conspicuous lesions. However, when there are multiple lesions and/or if they are diffuse and/or spread out, even this manual method fails no matter how the region of interest is specified. Thus, AAR-DQ not only offers an automated solution for disease measurement but also makes measurement itself possible on ill-defined lesions.

all ground truth images in $I_1^b$. FAM(B, G) is the fuzzy anatomy model of the whole object assembly in B for a specified hierarchical arrangement of the objects. $FM^T(O_\lambda)$ is the fuzzy model $FM(O_\lambda)$ of $O_\lambda$ after it has been transformed to match $O_\lambda$ optimally in a given test image I. $F_\lambda(x)$ and $f_\lambda(x)$ denote, respectively, the intensity distribution (histogram) of the tissue constituting object $O_\lambda$ within population G and the fit parametric intensity function. I denotes a test image and $I_1^D$ is the output fuzzy delineation of $O_\lambda$ in I. The procedures of the AAR-BCA method are illustrated in FIG. 1 and are discussed in more detail below.

As with the previous AAR methodology, we start off by developing a precise anatomic definition of each object involved in the AAR-BCA process. Although our focus is the quantification of body composition in terms of subcutaneous adipose tissue (SAT), visceral adipose tissue (VAT), muscle (Msl), and skeleton (Sk) in BT, we will need additional objects to facilitate the proper recognition and delineation of those objects of interest. These additional objects are listed in Table A1 along with their brief definitions and also illustrated on three axial slices (at the inferior, middle, and superior level for each object) on an lCT image of a patient in FIG. 2.

TABLE A1

Definitions of body regions and objects in the body torso.

| Abbreviation | Definition |
| --- | --- |
| Thx | Thoracic region extending from 5 mm inferior to the bases of the lungs to 15 mm superior to the lung apices. |
| Abd | Abdominal region extending from the point of bifurcation of the abdominal aorta into common iliac arteries to the superior aspect of the liver. |
| Plv | Pelvic region extending from the inferior aspect of the ischial tuberosities to the point of bifurcation of the abdominal aorta into common iliac arteries. |
| BT | Body torso defined to extend from the inferior aspect of the pelvic region to the superior aspect of the thoracic region. |
| Skin | The outer boundary of the skin (arms excluded) in the body torso. The interior region constitutes the entire body torso region. |
| Msl | All of the skeletal musculature in the body torso region. |
| Sk | All skeletal structures contained in the body torso region. |
| SAT | Subcutaneous adipose tissue in the body torso region. |
| VAT | Visceral adipose tissue internal to Msl in the body torso region. |
| IAM | The inner aspect of Msl. The interior region includes all visceral organs in the body torso, such as liver, lungs, etc., as well as air, fluid, and VAT in the body torso region. |
| OBM | The outer boundary of Msl. The interior region includes Msl, Sk, and IAM. |

Body Composition Analysis
Materials and Methods

The present disclosure may reference the terminology of Udupa J K, Odhner D, Zhao L, et al. Body-Wide Hierarchical Fuzzy Modeling, Recognition, and Delineation of Anatomy in Medical Images. *Med Image Anal.* 2014; 18(5): 752-771, but add additional notations that are specific to the present disclosure.

Reference may be made to the low-dose CT images of PET/CT acquisitions as lCT images. B denotes the body region of interest, which by default is the body torso, BT (herein). However, reference may be made to the thoracic, abdominal, and pelvic body (sub) regions individually. G denotes the human population group under consideration for which the model is built and for which we are interested in performing AAR-BCA. $I=\{I_1, \ldots, I_N\}$ is a set of lCT images of B of human subjects who belong to G. $O=\{O_1, \ldots, O_L\}$ represent L objects considered in B for the AAR-BCA procedure. $I_1^b=\{I_{1,1}, \ldots, I_{N,1}\}$ is the set of binary images representing the true delineations of object $O_\lambda$ in the images in I. $FM(O_\lambda)$ represents the fuzzy model of $O_\lambda$ derived from It should be noted that, although our final goal is BT-wide body composition quantification, the proposed method can also be applied to smaller regions of BT including the thorax (Thx), abdomen (Abd), and pelvis (Plv) as defined in Table A1, and can similarly be extended to the whole body including the head, neck, and extremities.

We will first briefly summarize the AAR method, and then elaborate on our adaptations for the BCA application. The main idea behind AAR is to use the training data sets to build a fuzzy anatomy model of B. This model includes a fuzzy sub-model for every object in B and the relationships between objects in B taken pair wise. The objects are arranged in a tree structure, and the relationships between a parent and its children, which characterize the geographical layout of the objects relative to each other, are codified in the model. The intensity characteristics of each object are also estimated and included in the model. Then, using this anatomy model, in any given test image, every object in B is recognized or localized. The recognition result is a fuzzy mask for each object which determines the approximate position, shape, and size of the object.

The fuzzy anatomy model FAM(B, G) is denoted by an ordered set of 5 entities FAM(B, G)=(H, M, $\rho$, $\lambda$, $\eta$). The first entity H represents the hierarchy of objects, which is formed in a tree structure. M={FM($O_\lambda$): $\lambda$=1, . . . , L} is a collection of sub-models, one for each object. $\rho$={$\rho_k$: k=1, . . . , L} is a set of relationship measures where $\rho_k$ denotes the relationship of object $O_k$ with its unique parent. It contains information regarding the position as well as orientation relationship between $O_k$'s parent and itself. The fourth parameter $\lambda$={$\lambda_k$: k=1, . . . , L} is a set of scale ranges indicating the size range of each object $O_k$ over the subject population. $\eta$ denotes a set of measurements pertaining to the object assembly in B, which includes all of the necessary estimated measures in the AAR method such as object intensity characteristics. In particular, it includes the intensity distributions of the different objects which are needed for the optimal recognition and delineation of the objects.

The formulation of the objects to be considered, or equivalently, the choice of objects to be included in H, plays a vital role in the effective recognition and delineation of the specific tissue regions for the application at hand. Tissue regions SAT and VAT are both referred to as sparse objects, which are spatially sparse and not compact, and are usually significantly more challenging to model, recognize, and delineate compared to compact and blob-like objects. These objects, especially VAT, are highly variable over G and raise the question of their very modelability.

To overcome these issues, we identify indirect objects which do not pose these challenges, but which, once modeled and recognized, facilitate the precise delineation of the actual tissue regions of interest.

Figure 2:
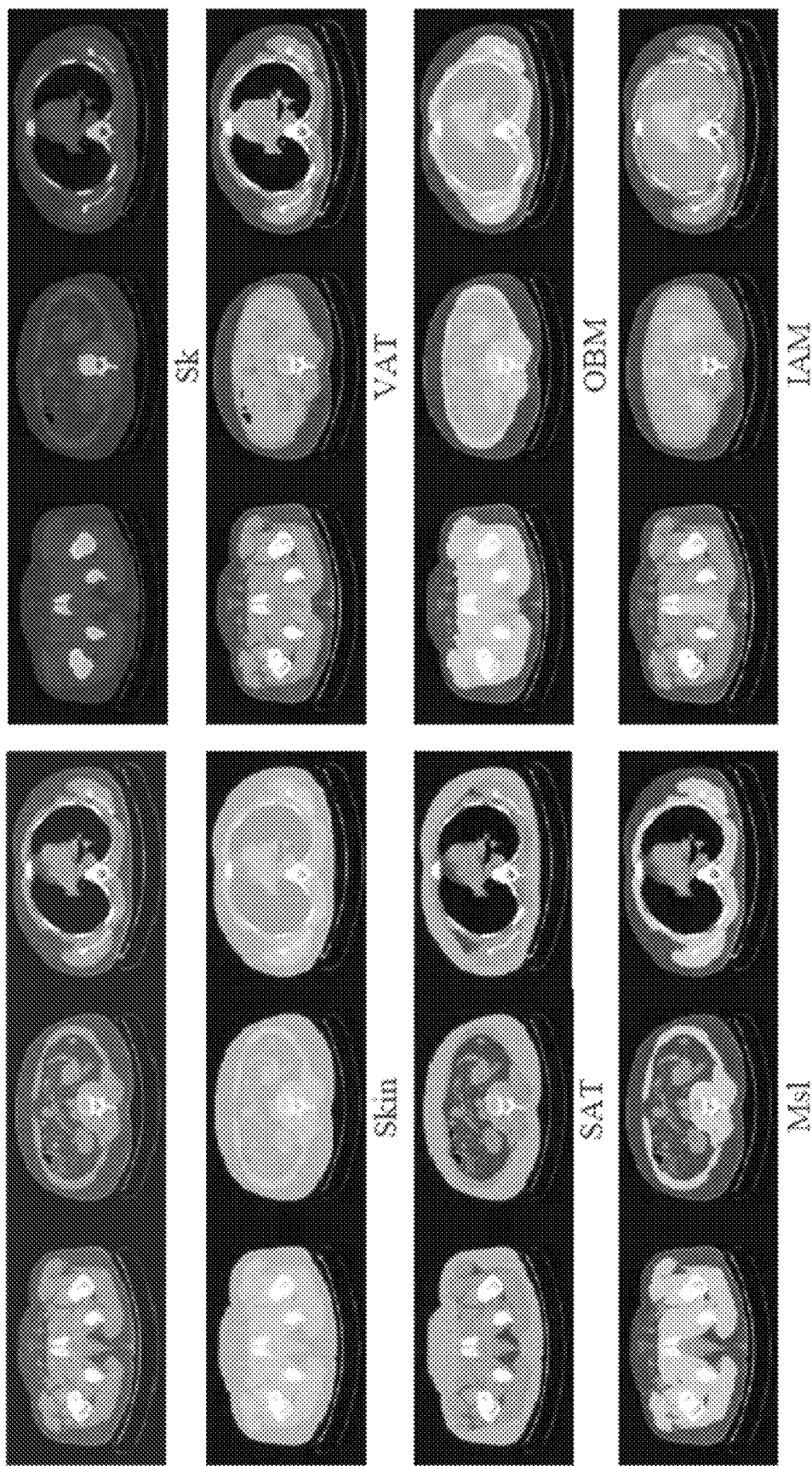
FIG. 2 illustrates representative examples of objects considered in AAR-BCA. The green masks superimposed on the low-dose CT (lCT) images are manually segmented object regions. Each row, from left to right, shows three axial slices selected from the inferior, middle, and superior aspects of the body torso in the same subject. See Table A1 for definition of the objects.

Following these ideas, in AAR-BCA we have identified two indirect objects, denoted IAM and OBM as defined in Table A1, which play a pivotal role in the delineation and separation of SAT and VAT. As seen in FIG. 2, OBM is defined as an object which is such that SAT is precisely the adipose (fat) tissue included within the object called Skin that is external to OBM (i.e., in the subcutaneous location). Similarly, IAM is formulated as an object which is such that VAT is exactly the adipose tissue that is inside of IAM (i.e., in the visceral location). In other words, if the position, shape, and size information of Skin, OBM, and IAM can be accurately obtained in a given image, then SAT and VAT can be subsequently derived based on the intensity properties of adipose tissue and these three object masks using appropriate logical predicate functions. It is important to note that IAM and OBM are not really anatomic objects, and, as is the case for many real anatomic objects, lack real tissue boundaries in several regions. For example, the posterior aspects of OBM and IAM inferiorly in the pelvis have no actual intervening tissue boundary between subcutaneous and visceral adipose tissue components as seen in FIG. 2. We should emphasize that, in the thoracic region, the definition of and the separation between SAT and VAT is complicated because their precise boundaries are somewhat ambiguous. The reasons for this are that the dome of the diaphragm intersects slices in the mid and lower thoracic region, which brings portions of the abdominal visceral region into the thoracic slices, as well as the lack of an easily identifiable SAT-VAT interface in the region of the cervicothoracic junction.

Figures 3A, 3B, 3C:
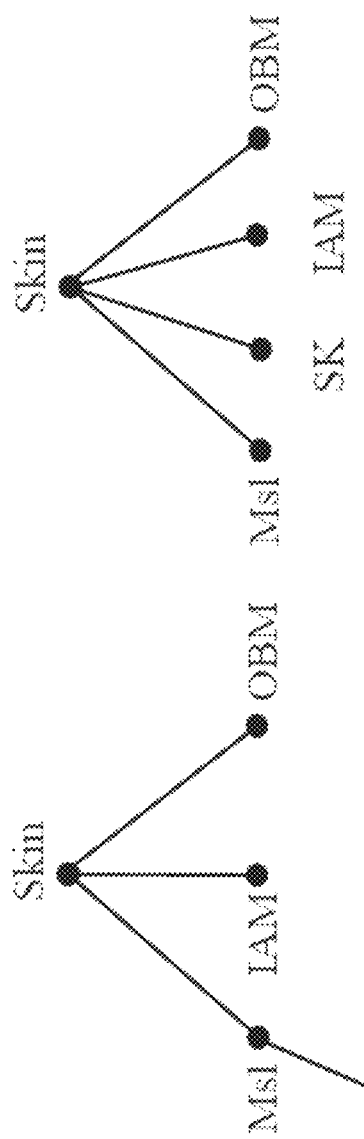
FIG. 3A illustrates a first example object hierarchy tested in AAR-BCA.
FIG. 3B illustrates a second example object hierarchy tested in AAR-BCA.
FIG. 3C illustrates a third example object hierarchy tested in AAR-BCA.

FIGS. 3A-C show examples of hierarchies utilized in the AAR-BCA method for BT. Among these and many other hierarchies that have been tested, the one shown in FIG. 3A has been found to be optimal from the perspective of object recognition, and hence, delineation. The main requirement for these hierarchies is that the root object should be easily recognizable. This is the reason that we chose the Skin object as the root. We will see later that, although several objects listed in Table A1 are not explicitly entered in the selected hierarchy H, they all come into picture in the AAR-BCA procedure eventually. One other point of notation needs to be clarified. Although all objects in the set O={$O_\lambda$: $\lambda$=1, . . . , L} as listed in Table A1 are of interest for AAR-BCA, not all objects will participate in every step. As we explained above, only the subset $O_H$={Skin, Msl, IAM, OBM, Sk} will be involved in the model building and recognition processes. Another subset of objects $O_{BC}$={SAT, VAT, Msl, Sk} will participate in the tissue quantification process. Furthermore, body regions {Thx, Abd, Plv} will enter into picture when we analyze the results of quantifying objects in $O_{BC}$ confined to these body regions. Given the set I of images, set $I_1^b$ of binary images over I for each object $O_\lambda$ considered in H, where each object is delineated as per the definitions in Table A1, and H itself, the process of constructing FAM(B, G) follows the AAR methodology described in [Udupa J K, Odhner D, Zhao L, et al. Body-Wide Hierarchical Fuzzy Modeling, Recognition, and Delineation of Anatomy in Medical Images. *Med Image Anal.* 2014; 18(5): 752-771] in forming M, $\rho$, and $\lambda$. For the formation of the $5^{th}$ entity $\eta$, however, the procedure is slightly different in the actual information gathered while building FAM(B, G). In the AAR approach[1], since delineation is performed by a model-based iterative relative fuzzy connectedness (IRFC) algorithm, the fuzzy affinity parameters needed by the IRFC algorithm for object $O_\lambda$ are estimated from $I_1^b$, other nearby co-object tissue regions, and I. In AAR-BCA, the delineation procedure is different, as explained later, and it requires just the intensity distribution within $O_\lambda$. This information is estimated as follows.

[1] Udupa J K, Odhner D, Zhao L, et al. Body-Wide Hierarchical Fuzzy Modeling, Recognition, and Delineation of Anatomy in Medical Images. *Med Image Anal.* 2014; 18(5): 752-771.

Let $F_\lambda(x)$ denote the intensity distribution of the tissue constituting object $O_\lambda$. We take $F_\lambda(x)$ to be the image intensity histogram of the interior of $O_\lambda$ over all samples of $O_\lambda$ as represented in I. To handle issues such as noise, missing intensities, artifacts due to segmentation etc., instead of using $F_\lambda(x)$ directly we fit a smooth function to $F_\lambda(x)$ and take the fit function as the intensity distribution for object $O_\lambda$. After observing $F_\lambda(x)$ for objects $O_\lambda \in O_{BC}$, we decided to approximate $F_\lambda(x)$ by the following function using a least squares method[2].

[2] Stigler S M. Gauss and the Invention of Least Squares. *Ann Stat.* 1981; 9(3): 465-474.

$$f_1(x) = a_1 e^{-\left(\frac{x-\mu_1}{\sigma_1}\right)^2} + a_2 e^{-\left(\frac{x-\mu_2}{\sigma_2}\right)^2}$$

Figure 4:
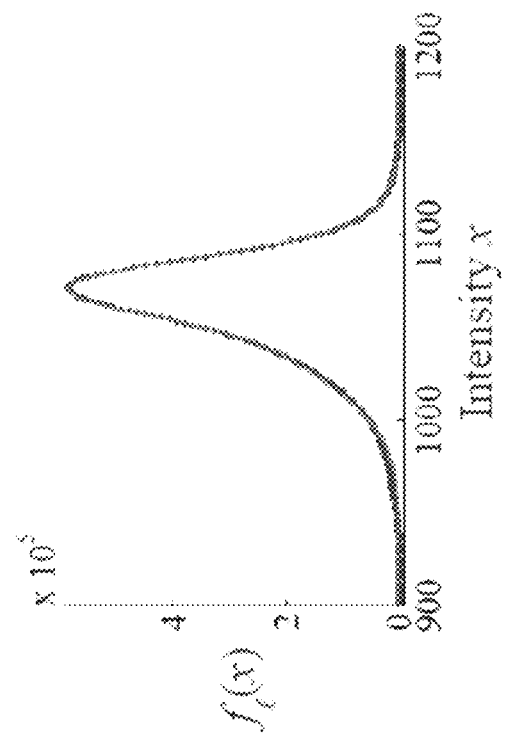
FIG. 4 illustrates left: Intensity histogram $F_i(x)$ for Msl; and right: The fit function $f_i(x)$ together with $F_i(x)$.
Figure 4:
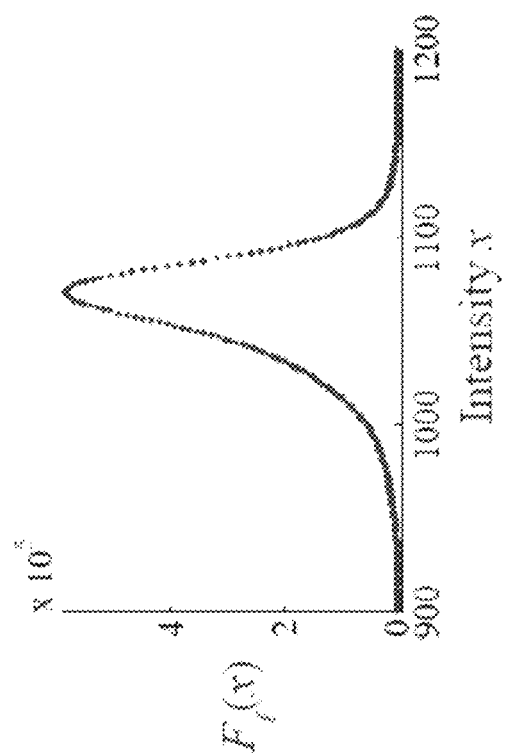

All parameters of $f_1(x)$, including $a_1$, $a_2$, $\mu_1$, $\mu_2$, $\sigma_1$, and $\sigma_2$, are estimated using the Gauss-Newton method[3] to solve the nonlinear least squares problem. FIG. 4 illustrates this fitting process for object Msl for our data set. The parameters of $f_\lambda(x)$ for each object $O_\lambda$ then become part of the entity $\eta$ in FAM(B, G). The intensity function $f_\lambda(x)$ will be utilized in delineating the objects in $O_{BC}$ as explained below Notably, since the intensity distributions for objects SAT and VAT are the same, the fit intensity function $f_\lambda(x)$ will also be the same for them. For bone tissue, a slightly modified version, namely $f_1'(x)$, of $f_1(x)$ is used as the final membership function, where $f_1'(x)$ is identical to $f_1(x)$ on the left shoulder of $f_1(x)$ up to the value of x where $f_1(x)$ reaches its maximum, and then $f_1'(x)$ will remain at maximum value for all values of x. This is necessary to make sure that we capture soft and cortical bone tissue in the modified membership function $f_1'(x)$.

[3] Gratton S, Lawless A S, Nichols N K. Approximate Gauss-Newton Methods for Nonlinear Least Squares Problems. *Siam J Optimiz.* 2007; 18(1): 106-132.

Object Recognition

The purpose of recognition is to determine the pose, including position, rotation, and scale, of a target object $O_\lambda$ in a given test image I by using the model FAM(B, G). The output $FM^T(O_\lambda)$ of recognition is a transformed version of the fuzzy model $FM(O_\lambda)$ of $O_\lambda$ which indicates the location of $O_\lambda$ in I. Voxel-by-voxel it denotes the certainty of each voxel in I being covered by $O_\lambda$ in its placement by $FM^T(O_\lambda)$. The recognition procedure follows the hierarchy H chosen while building the model of B, and follows H top-down locating objects in I one by one. First, the root object is recognized (see Udupa J K, Odhner D, Zhao L, et al. Body-Wide Hierarchical Fuzzy Modeling, Recognition, and Delineation of Anatomy in Medical Images. *Med Image Anal.* 2014; 18(5): 752-771 for details). Then, while proceeding down H, assuming that the parent of $O_\lambda$ is already recognized, the parent-offspring relationship $\rho_\lambda$ is utilized to guide placement of $O_\lambda$ relative to its parent in I. Subsequently, this pose is refined by an optimal search[4], which yields $FM^T(O_\lambda)$. Improvements over previous work in recognition procedures include: the body region BT is larger (compared to body regions neck, thorax, and abdomen dealt with separately in previous work[5]), and the objects dealt with are different.

[4] Udupa J K, Odhner D, Zhao L, et al. Body-Wide Hierarchical Fuzzy Modeling, Recognition, and Delineation of Anatomy in Medical Images. *Med Image Anal.* 2014; 18(5): 752-771.

[5] Id.

Object Delineation

For any given image I, the recognition process yields a fuzzy mask $FM^T(O_\lambda)$ over I for each object $O_\lambda$. We first utilize the intensity function $f_\lambda(x)$ of $O_\lambda$ to transform I into an intensity membership image, denoted $IM_\lambda(I)$ which expresses at each voxel v of I the fuzzy membership of v in $O_\lambda$ based only on the intensity characteristics of $O_\lambda$. We then delineate $O_\lambda$ in I as a fuzzy membership image $I_1^D$ of $O_\lambda$ by using a fuzzy predicate operation involving $FM^T(O_\lambda)$ and $IM_\lambda(I)$. With a slight extension of the notation, we denote the fuzzy membership of $FM^T(O_\lambda)$ at voxel v of I by $[FM^T(O_\lambda)](v)$ and the intensity membership of $IM_\lambda(I)$ at v by $[IM_\lambda(I)](v)$. The latter is thus defined by $[IM_1(I)](v)=f_1(I(v))$.

The basic idea of fuzzy delineation is to take the location information from the model component $FM^T(O_\lambda)$ and the image intensity membership information from $IM_\lambda(I)$ to decide on the final delineation membership $I_1^D(v)$ of each voxel v in I. In this process, for each object $O_\lambda$, two thresholds are employed, one $Th_1^{FM}$ for the fuzzy model membership value $[FM^T(O_\lambda)](v)$ and another $Th_1^{IM}$ for the intensity membership value $[IM_\lambda(I)](v)$ (see below as to how these thresholds are estimated automatically and optimally). The predicate operation is different for the different objects in $O_{BC}$, as enumerated below:

For $O_\lambda \in \{Msl, Sk\}$, $$I_1^D(v) = \begin{cases} IM_1(v), & \text{if } [FM^T(O_1)](v) > Th_1^{FM} \ \& [IM_1(I)](v) > Th_1^{IM} \\ 0, & \text{otherwise} \end{cases}$$

-continued

For $O_\lambda = SAT$, $$I_1^D(v) = \begin{cases} IM_1(v), & \text{if } [FM^T(O_k)](v) < Th_1^{FM} \ \& [IM_1(I)](v) > Th_1^{IM} \\ 0, & \text{otherwise} \end{cases},$$

where $O_k = OBM$.

For $O_\lambda = VAT$, $$I_1^D(v) = \begin{cases} IM_1(v), & \text{if } [FM^T(O_k)](v) > Th_1^{FM} \ \& [IM_1(I)](v) > Th_1^{IM} \\ 0, & \text{otherwise} \end{cases},$$

where $O_k = IAM$.

Note how objects IAM and OBM are utilized. The delineation of Msl and Sk is not influenced by IAM and OBM. The output membership at v is taken to be intensity membership $[IM_\lambda(I)](v)$ if the model membership and the intensity membership both strongly confirm (above the respective thresholds) that v is to be considered to be in the object. Notably, the result itself is fuzzy. For SAT, the exterior (complement) of the model $FM^T(OBM)$ is taken as the model component of evidence, since SAT resides outside OBM (see FIG. 2), and hence the logic shown in its predicate function. For VAT, since it resides in the interior of object IAM (FIG. 2), the logic is similar to those of Msl and Sk, with one difference, namely that the object used as model mask is IAM and not VAT itself.

Estimating Optimal Thresholds $Th_1^{FM}$ and $Th_k^{IM}$:

We essentially perform a delineation rehearsal on the training image data set I, and knowing the associated true delineations $I_1^b$ for each object $O_\lambda \in O$, we estimate these thresholds by minimizing the delineation error. To elaborate, first the anatomy model FAM(B, G) is built using $I_1^b$, $\lambda=1, \ldots, L$, and I. Then, the objects in $O_H$ are recognized following the recognition methods, which yields, for each object $O_\lambda$ in $O_H$ and image I in I, the fuzzy model $FM^T(O_\lambda)$. Knowing the intensity function $f_\lambda(x)$ of each object $O_\lambda$ in $O_{BC}$, we generate the intensity membership image $IM_\lambda(I)$. Thus, for each image $I \in I$, we now have $FM^T(O_\lambda)$ for each $O_\lambda \in O_H$ and $IM_k(I)$ for each $O_k \in O_{BC}$. Therefore, for any given thresholds $t_1$ on $FM^T(O_\lambda)$ and $t_2$ on $IM_k(I)$, we can determine the delineations $I_k^D(v)$ for each $O_k \in O_{BC}$ and $I \in I$. Let the true delineation of $O_k$ in I be $I_{n,k}^b$ (which is of course one of the images in the set $I_k^b$) and let $Q_k(t_1, t_2)$ denote the sum of squares of the fuzzy false positive volume and fuzzy false negative volume[6] between $I_k^D(v)$ and $I_{n,k}^b$ over all images in I. That is,

[6] Udupa J K, Leblanc V R, Ying Z, et al. A Framework for Evaluating Image Segmentation Algorithms. *Comput Med Imag Grap.* 2006; 30(2): 75-87.

$$Q_k(t_1, t_2) = \Sigma_{I \in I} \Sigma_{all\ v}\ in\ I[(I_k^D(v) - I_{n,k}^b(v))^2 + (I_{n,k}^b(v) - I_k^D(v))^2].$$

Note here that $(I_k^D(v) - I_{n,k}^b(v))$ denotes the fuzzy false positive value at v. It is intended as a fuzzy logic operation (or fuzzy set difference) between the fuzzy membership image $I_k^D(v)$ and the binary image $I_{n,k}^b(v)$, meaning that the actual value $(I_k^D(v) - I_{n,k}^b(v))$ is taken only if it is positive; otherwise it is set to 0. The same principle applies to $(I_{n,k}^b(v) - I_k^D(v))$ which denotes the fuzzy false negative value at v. The optimal threshold pair $(Th_1^{FM}, Th_k^{IM})$ is estimated by minimizing $Q_k(t_1, t_2)$.

$$(Th_1^{FM}, Th_k^{IM}) \hat{\imath} \underset{(t_1, t_2)}{\arg\min} [Q_k(t_1, t_2)].$$

In our implementation, we use a multi-resolution strategy to search for optimal thresholds. From prior knowledge, we know the approximate range of values for these thresholds. The initial (coarse resolution) search is carried out based on this range and larger steps. Once an optimal pair is found, the search is refined using a smaller step size to search around and starting from the coarse optimal value. In our implementation, we set the coarse searching range of $Th_1^{FM}$ to the interval from the median value of $FM^T(O_\lambda)$ to 1, and that of $Th_k^{IM}$ to the interval from 0 to the median value of $IM_\lambda(I)$. The step sizes of each iteration is $(0.1)^m$, where m denotes iteration number. Usually convergence is achieved within 3 to 4 iterations. Note that this step of finding optimal thresholds is actually performed in the model building stage, and $(Th_1^{FM}, Th_k^{IM})$ become part of item η of FAM(B, G).

After the delineation step, any small amounts of artifacts remaining in $I_1^D$, caused by partial volume effects or residual components of the scanning table, etc., are suppressed by a 2D morphological opening operation performed in the slice plane for one iteration using a structuring element formed by the 8-neighbors of each pixel.

Experiments and Results

Image Data Sets

A retrospective study was conducted following approval from the Institutional Review Board at the Hospital of the University of Pennsylvania along with a Health Insurance Portability and Accountability Act waiver. The image data set used in our experiments is selected from our hospital patient image database by a board-certified radiologist (co-author Torigian), and is verified to be of acceptable quality. This data set includes 20 near-normal subjects and 5 lung cancer patients who previously underwent 18F-2-fluorodeoxyglucose (FDG) PET/CT imaging without administration of intravenous contrast material on a 16-detector row LYSO PET/CT scanner with time-of-flight capabilities (Gemini TF, Philips Healthcare, Bothell, Wash.). The low-dose CT images were acquired during quiet respiration using a kVp of 120, an effective mAs of 50, and a gantry rotation time of 0.5 msec, and reconstructed using a standard soft tissue kernel. For each subject, following the definition of BT (see Table A1), any extra slices falling outside the BT region were removed manually. Then, each of the 10 objects in the set O was segmented in each lCT image of the 25 PET/CT acquisitions to serve as the reference standard, adhering to the object definitions formulated in Table A1. The segmentation tools used include iterative live wire, thresholding, manual painting, and correction. The ground truth segmentations were performed by well-trained operators and verified for accuracy by the same radiologist. All data sets were from male subjects in the age range 31-71 years. The voxel sizes for CT and PET were, respectively, 1.2×1.2×4 mm³ and 4×4×4 mm³.

Evaluation Methods and Metrics

We employ a 5-fold cross validation strategy for evaluating AAR-BCA with a 15-10 train-test data division. That is, the training set consisting of 15 images is formed by choosing randomly 15 out of the 25 subjects, FAM(B, G) is built based on these images, the performance of AAR-BCA is then tested on the images of the remaining 10 subjects, and the entire process is repeated 5 times. For each of the 5 groups, normal subjects and lung cancer subjects appear in both training and testing data sets. Additionally, for any two groups, the overlapped subjects for training and testing are no more than 10. The results reported are all based on 50 AAR-BCA experiments designed in this fashion. As in the AAR approach[7], recognition accuracy is expressed by localization error and scale error. The former describes the distance of the geometric center of the actual object and the found model $FM^T(O_\lambda)$ for each $O_\lambda$ in $O_H$. The latter denotes the ratio of the estimated object size to the true size. The ideal values for the two measures are 0 and 1, respectively.

[7] Udupa J K, Odhner D, Zhao L, et al. Body-Wide Hierarchical Fuzzy Modeling, Recognition, and Delineation of Anatomy in Medical Images. *Med Image Anal.* 2014; 18(5): 752-771.

For delineation, since our output is fuzzy (and not binarized), we will use false positive volume fraction (FPVF) and false negative volume fraction (FNVF) defined for comparing fuzzy delineations with binary ground truth delineations as formulated in Udupa J K, Leblanc V R, Ying Z, et al. A Framework for Evaluating Image Segmentation Algorithms. *Comput Med Imag Grap.* 2006; 30(2): 75-87. We have included a new metric based on Hausdorff boundary distance (HD) adapted to fuzzy delineations. We compute HD between a fuzzy output $X_f$ and the corresponding binary true segmentation $X_t$ by first thresholding $X_f$ and then determining HD between the two binary volumes. HD will thus become a function of the chosen threshold. We will present the mean HD curve (as a function of the threshold on fuzzy membership) for each object in $O_H$ computed over the 50 experiments to demonstrate how the boundary distance metric for the fuzzy delineation results varies for each delineated object.

Results

Figure 5:
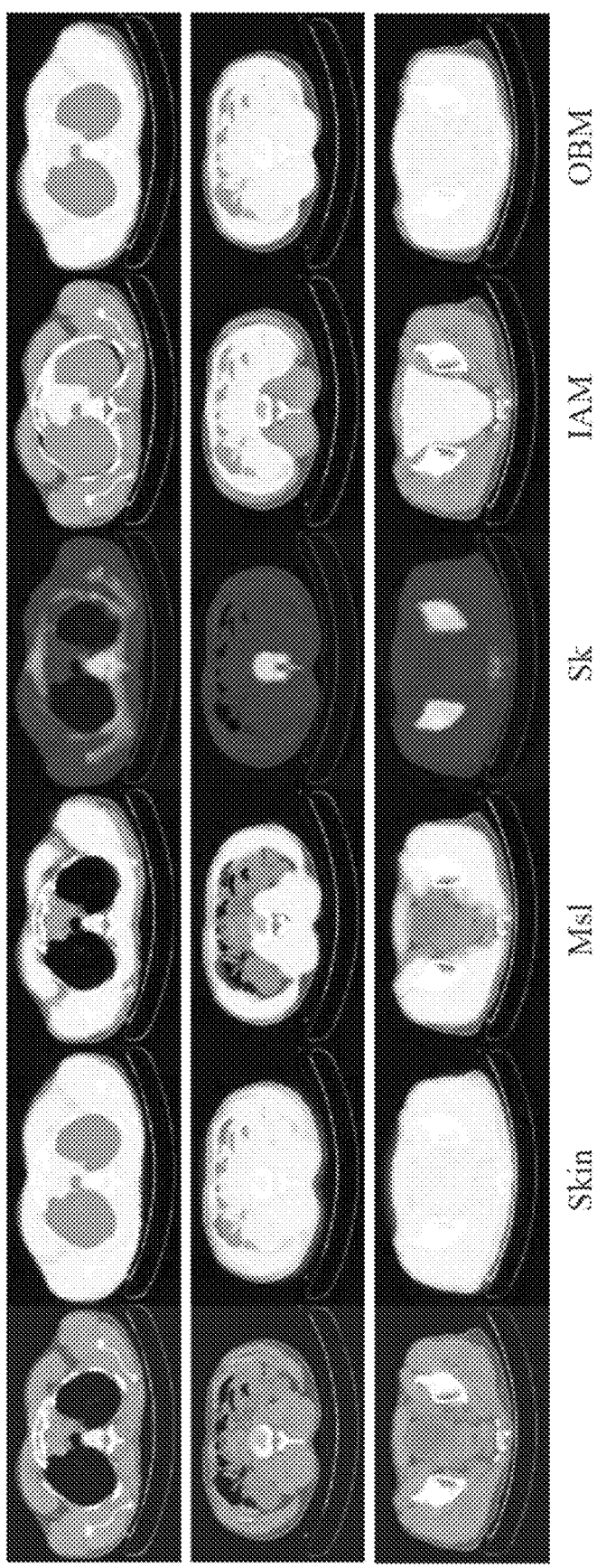
FIG. 5 illustrates sample recognition results on a test image for the different objects in the hierarchy in FIG. 3A. Top-down: Three slices selected from the superior, middle, and inferior aspect of the body torso are shown, original slices on the first column, slices of recognized objects overlaid on the original slices in other columns for different objects.

Sample recognition results for the hierarchy in FIG. 3A are displayed in FIG. 5 for one test image, where, for each object in $O_H$, a slice of the fuzzy model $FM^T(O_\lambda)$ at recognition is shown overlaid on the corresponding slice of the image. Table A2 lists the mean and standard deviation of location and size errors for the objects in $O_H$ for the three hierarchies in FIGS. 3A-C. As mentioned previously, the hierarchy in FIG. 3A yielded the best recognition results among the hierarchies we tested, so it is used subsequently for obtaining all delineation results.

TABLE A2

Location error (in mm) and size error for the hierarchies shown in FIGS. 3A-C. Mean (and standard deviation) values are listed in each cell.

|  | Loc error (mm) | Size error | Loc error (mm) | Size error | Loc error (mm) | Size error |
|---|---|---|---|---|---|---|
| Skin | 5.6 (3.5) | 1.00 (0.02) | 5.6 (3.5) | 1.00 (0.02) | 5.6 (3.5) | 1.00 (0.02) |
| Msl | 12.7 (9.0) | 1.00 (0.02) | 12.7 (9.0) | 1.00 (0.02) | 13.7 (8.8) | 1.00 (0.02) |
| Sk | 11.2 (6.2) | 0.98 (0.03) | 11.4 (6.1) | 0.99 (0.03) | 12.1 (6.5) | 0.99 (0.03) |

TABLE A2-continued

Location error (in mm) and size error for the hierarchies shown in FIGS. 3A-C.
Mean (and standard deviation) values are listed in each cell.

|  | Loc error (mm) | Size error | Loc error (mm) | Size error | Loc error (mm) | Size error |
|---|---|---|---|---|---|---|
| IAM | 16.0 (7.5) | 1.05 (0.04) | 16.0 (7.5) | 1.05 (0.04) | 16.0 (7.5) | 1.05 (0.04) |
| OBM | 7.0 (4.3) | 1.00 (0.03) | 7.0 (4.3) | 1.00 (0.03) | 7.0 (4.3) | 1.00 (0.03) |

Figure 6:
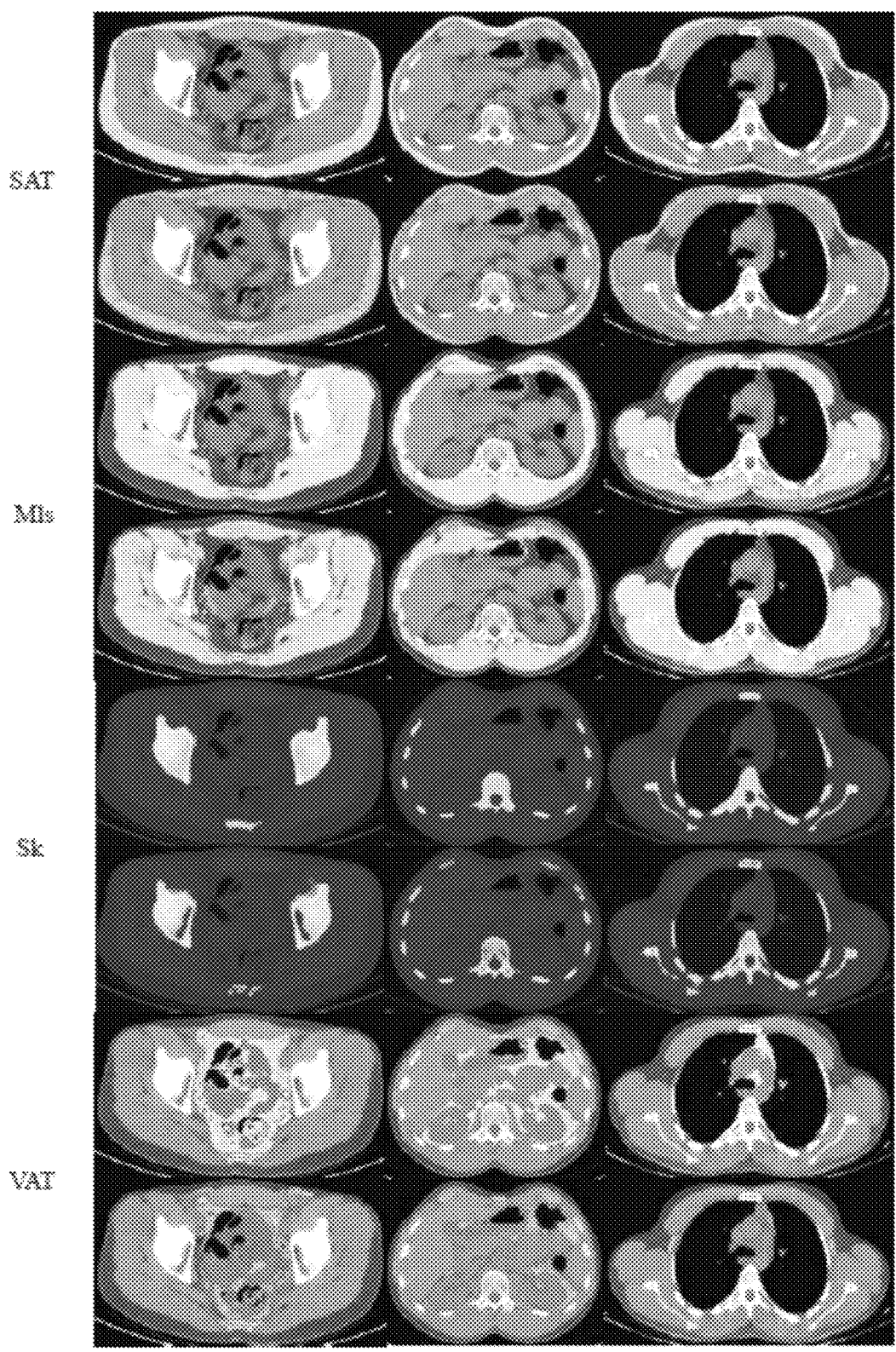
FIG. 6 illustrates sample delineation results for AAR-BCA. For each object delineated, the fuzzy delineation (lower row) and ground truth binary delineation (upper row) are shown overlaid on the original test image slices. Slices selected from inferior (left), middle (middle), and superior (right) aspect for each object are shown.

Sample delineation results are displayed in FIG. 6 for the objects in $O_{BC}$ on one test image where the fuzzy delineations are overlaid on the original image slices. The ground truth binary delineations are also shown in a similar manner for comparison. Since the AAR-BCA results are fuzzy, depending on the membership at a voxel and due to translucent overlay, some subtle regions do not show up prominently, like for VAT and SAT.

TABLE A3

The mean and standard deviation of fuzzy FPVF and FNVF of the AAR-BCA delineations for BT, Thx, Abd, and Plv body regions.

|  | BT | | Thx | | Abd | | Plv | |
|---|---|---|---|---|---|---|---|---|
|  | FPVF | FNVF | FPVF | FNVF | FPVF | FNVF | FPVF | FNVF |
| SAT | 0.036 | 0.027 | 0.027 | 0.051 | 0.044 | 0.021 | 0.035 | 0.018 |
|  | 0.022 | 0.032 | 0.019 | 0.059 | 0.033 | 0.027 | 0.018 | 0.029 |
| Msl | 0.037 | 0.064 | 0.035 | 0.053 | 0.049 | 0.085 | 0.033 | 0.062 |
|  | 0.012 | 0.048 | 0.011 | 0.050 | 0.020 | 0.073 | 0.015 | 0.078 |
| Sk | 0.033 | 0.030 | 0.036 | 0.020 | 0.028 | 0.018 | 0.036 | 0.043 |
|  | 0.013 | 0.029 | 0.012 | 0.015 | 0.013 | 0.014 | 0.018 | 0.060 |
| VAT | 0.038 | 0.044 | 0.033 | 0.029 | 0.056 | 0.036 | 0.028 | 0.059 |
|  | 0.021 | 0.045 | 0.032 | 0.039 | 0.036 | 0.046 | 0.013 | 0.062 |

Figure 7:
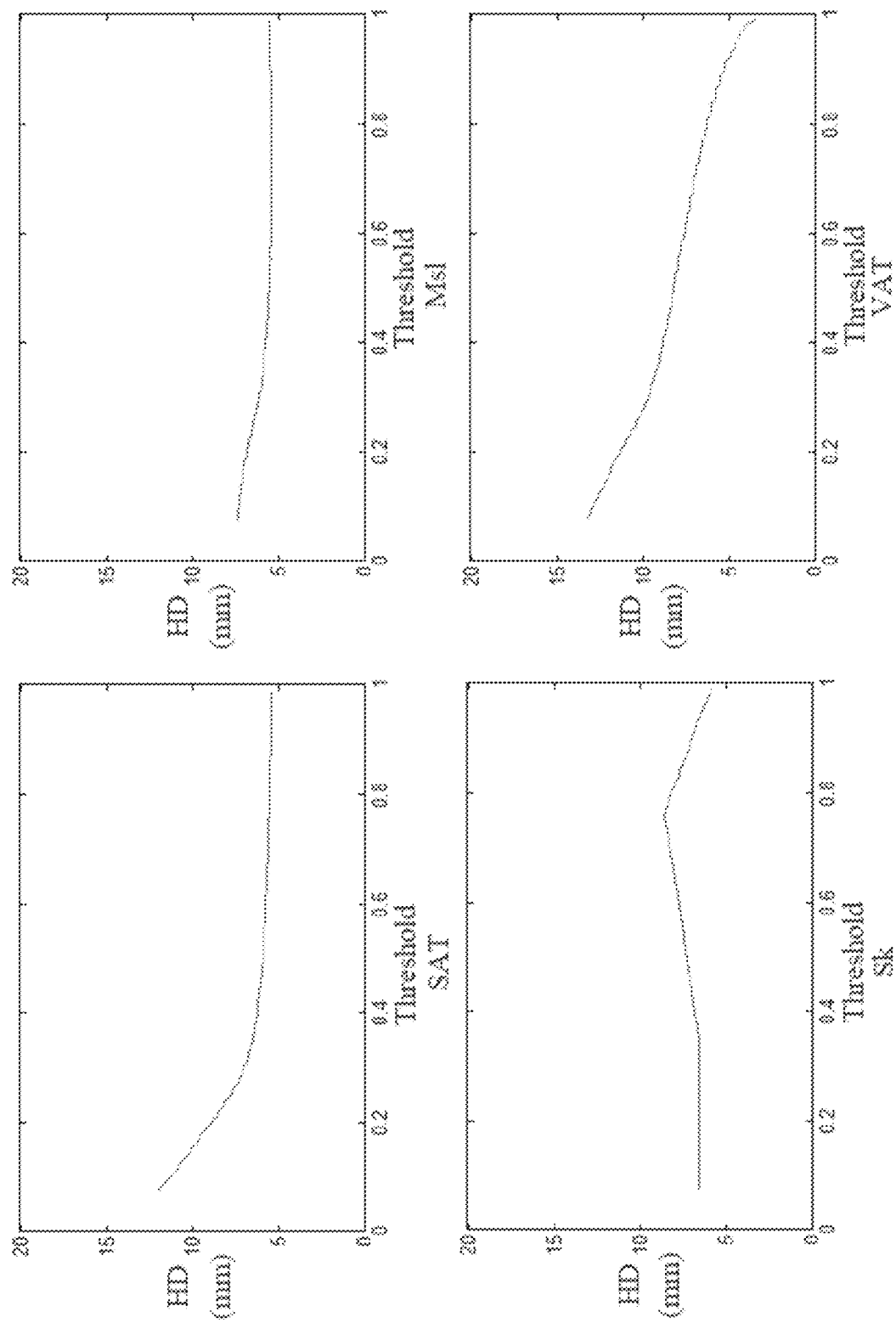
FIG. 7 illustrates delineation accuracy via fuzzy boundary distance curves. The mean Hausdorff Distance (HD) curves for the delineations of SAT, Msl, Sk, and VAT produced by AAR-BCA over all experiments are displayed.

Quantitative evaluations of AAR-BCA delineation results are summarized in Table A3 for the BT region for the four tissue types. The table also lists evaluation metrics by smaller body regions—for Thx, Abd, and Plv for the same tissues. Mean and standard deviation of FPVF and FNVF are listed for each object in $O_{BC}$. Finally, FIG. 7 portrays the boundary distance metric via mean HD curves obtained for the objects in $O_{BC}$.

Discussion

For BT, over all objects, AAR-BCA achieves a FPVF of 3.6% and FNVF of 4.2%. In segmentation literature, this level of accuracy is considered excellent. Notably, SAT and Sk both achieve a FPVF under 4% and a FNVF under 3%. For Msl, the FNVF of 6.4% is higher than for other objects and so also for VAT (4.4%). This seems to be mainly due to the challenges in matching perfectly the undulate margins of the Msl object properly and uniformly via the localized fuzzy model $FM^T(Msl)$.

VAT is particularly a challenging object to delineate since its total volume is small and it is spatially sparsely distributed within the body with very complex shape as an object. This is exemplified by the inferior slice in the pelvic region for VAT in FIG. 6. Under these considerations, our result for VAT (as well as for SAT) is quite remarkable, especially in view of the lower quality of lCT images compared to diagnostic CT images. We believe this has been facilitated by the two conceptual objects we introduced into the AAR methodology, namely, IAM and OBM, and also by the fuzzy stance taken for delineation. As we can see from Table A2, the recognition results for these objects are accurate enough to make the predicate functions perform their task of accurate delineations of SAT and VAT. This is a key central idea underlying the AAR-BCA approach for body composition analysis.

The fuzzy boundary of AAR-BCA delineations cannot be strictly compared with the hard boundaries of the ground truth delineations. The boundary distance measure HD displayed in FIG. 7 helps to some extent to illustrate how the iso-membership boundaries of AAR-BCA match the boundary of ground truth delineations. Note that, as can be expected, in closest match, the distance between the two boundaries is about 1 voxel (~4 mm). Object Sk demonstrates an interesting behavior where the match worsens at higher membership thresholds and again improves as this threshold is increased. We believe this is due to the fact that the ground truth delineations of bone actually contain two types of tissues—hard cortical bone and soft medullary bone. We believe that the accuracy for Sk would have been higher if we treated these two component tissues separately.

Note also that for Thx, Abd, and Ply, FPVFs and FNVFs mostly remain at the same level as for BT. In Thx, all objects achieve FPVFs under 4%, particularly SAT, under 3%. The FNVFs are a little higher than 5% for SAT and Msl, but under 3% for Sk and VAT. In Abd, Sk has the best results in both FPVF (2.8%) and FNVF (1.8%) among all regions. However, Msl has inferior results (FPVF of 4.9% and FNVF of 8.5%) in Abd compared to other regions. In Ply, FPVFs of all objects achieve less than 4%, but FNVF ranges from 1.8% (for VAT) to 6.2% (for Msl). The above differences among different regions are mainly caused by the influence of other organs. In Abd for Msl, for example, confounding objects like stomach, liver, etc. influence recognition as well as delineation.

The following computational times are estimated on a modern desktop Dell computer with the following specifications: 4-core Intel Xeon 3.3 GHz base to 3.7 GHz max turbo CPU with 8 GB RAM and running the GNU/Linux 3.11.10-25-desktop operating system. Building FAM(B, G) from 15 lCT images using the hierarchy of FIG. 3A takes about 2,530 seconds excluding the threshold optimization step of Equation (6) which takes about 3,600 seconds for all four objects. Thus, model building on 15 images takes about 1.7 hours in total. Object recognition costs about 18 seconds per object per lCT image, and the actual delineation step costs less than 1 second per object per image.

Thus, once the model FAM(B, G) is built, full body torso composition analysis of the four tissue components can be completed in about 1 minute per study.

Previous work in the field often needs interactive operations, and many of them perform body composition analysis based on just one slice. Many of the previous solutions just focus on the problem of quantifying SAT and VAT tissue components only. In previous AAR work, the segmentation and quantification of SAT, VAT, and muscle in the abdomen (not the whole body torso) and bone tissue in the thorax and abdomen utilizing contrast enhanced diagnostic CT images were reported. The previous approach modified an iterative relative fuzzy connectedness (IRFC) algorithm to take model information for delineation following the object recognition step. It achieved (FPVF, FNVF) as follows for these tissue components. Abdominal SAT: (5%, 12%); abdominal muscle: (13%, 9%); abdominal skeleton: (6%, 14%); thoracic skeleton: (19%, 13%). Since that approach was based on modeling explicitly each object, and recognizing and then delineating the object, it did not directly delineate the VAT component since meaningful modeling of VAT was very difficult. AAR-BCA not only extends the body domain of application but also substantially improves on these earlier results through three key strategies: (1) Instead of modeling directly SAT and VAT objects, better "modelable" indirect objects are designed, defined anatomically in a consistent manner, and employed for delineating SAT and VAT tissue regions through them. (2) The collection of objects and their hierarchy within the AAR framework that best suits our goal of delineating the four tissue components is determined. (3) The IRFC algorithm is replaced by a logical predicate function involving the fuzzy models and intensity membership functions. While the model-based IRFC engine works well when solid organs are to be delineated, the sparse and scattered objects, particularly SAT, VAT, and Msl, pose challenges in accurately and automatically identifying an adequate set of seeds needed for their fuzzy connected delineation. Since it is difficult to ascertain that seeds are planted automatically in each scattered component of the same tissue region, the proposed fuzzy predicate solution works better than the previous AAR-IRFC.

In summary, AAR-BCA seems to be more accurate and able to handle other and more challenging body regions like the thorax and pelvis for body composition analysis efficiently, even on lCT images, compared to the currently existing solutions.

Since PET/CT imaging is commonly used in the above disease conditions, we sought to perform body composition analysis on the more challenging lCT images that are acquired as part of routine PET/CT examination. Through a confluence of three key ideas—carefully identifying the needed (including indirect) objects; finding the AAR hierarchy that is best suited for our application; and using a fuzzy predicate that combines model and intensity membership information—we extended the previous AAR approach to design the AAR-BCA method for quantifying bone tissue, muscle tissue, SAT, and VAT in the body torso. One important feature of AAR-BCA is that it is parameter free. All needed variables are automatically estimated from the training data sets, and no manual setting or adjustment of any parameters is needed. AAR-BCA can quantify the four tissue components in the body torso with about 5% overall error in about 1 minute per patient image.

The present disclosure demonstrates the quantification results in body-torso-wide application, but also parcellated the results to smaller body regions to understand how accuracy varied over different body regions. AAR-BCA can also be applied to a smaller body region on diagnostic CT (dCT) or lCT. For instance, we can use abdominal dCT images for training and then quantify body composition on abdominal dCT images. We can also perform training on abdominal lCT images. In fuzzy set theory, many membership functions are available which can be used as predicate functions.

As discussed herein above, image data may also be used for disease quantification.

Disease Quantification

Now we describe another aspect of the disclosure—disease quantification. In patients with lymphoma, other cancers, and other non-neoplastic disease conditions such as inflammatory disorders, body-wide accurate disease quantification becomes crucial for disease staging, prognosis assessment, treatment prediction assessment, treatment response assessment, and restaging/surveillance. These decision-making tasks call for assessment of abnormal states such as disease burden and other properties within lymph node zones and extranodal pathological regions within organs throughout the body. The derivation of disease quantity from medical images in turn requires methods to identify and delineate certain 3D "objects" in images body-wide. In this context, the "object" may be an anatomic organ, a sub-organ, a tissue region, or a well-defined 3D lymph node station/zone. Called image segmentation, this process of locating and delineating "objects" in images has a long history in the area of image processing spanning over 5 decades. Practical production-mode image segmentation, especially body-wide, however, has remained the hardest challenge in medical image analysis and an essential roadblock to the practical implementation of routine body-wide disease measurement in the clinic.

Consequently, since object delineation is a prerequisite for disease quantification, no method is currently available for body-wide disease burden estimation that is accurate, has a high level of automation, and can quantify disease burden in the above objects individually and collectively, especially on positron emission tomography/computed tomography (PET/CT) acquisitions. Consequently, clinical disease measurement is usually done manually. Since manual assessment of body-wide disease burden in systemic diseases is extremely labor-intensive, time-consuming, and simply impractical, usually a few high 18F-fluorodeoxyglucose (FDG) uptake sites/lesions/nodes on PET images are selected for manual measurement. Additionally, most clinical software systems are effective in measuring only well-defined focal and discrete "hot" lesions, but fail on ill-defined or less avid lesions which may be widespread. This type of selective and sampled measurement may introduce bias and operator-dependent variations. This may also lead to wrong conclusions due to unknown factors of how well the selected measurements portray total and object-wise disease burden and the importance of the sites that are not considered for measurement.

Thus, there is a critical need for clinical tools enabling practical standardized body-wide disease quantification from PET/CT images in patients with lymphoma and other disease conditions so that clinical outcomes may be maximized. Such tools will be especially important to facilitate meaningful comparisons between patients and results among studies, as well as to objectively evaluate new treatments that are under development including targeted, immunomodulatory, cell-based, and other therapeutic agents. The lack of practical tools to measure disease body-wide, body-region-wise, organ-wise, and nodal zone-wise is therefore currently a serious impediment. This is a barrier to progress in cancer care and research, particularly in disease staging, outcome prognostication, and response assessment which require precise disease quantity information and localization throughout the body.

Quantitative Radiology (QR) may be defined as an emerging discipline within radiology wherein detailed quantitative information derived from images is used to improve clinical tasks pertaining to disease management such as screening, diagnosis/detection, staging, prognosis assessment, treatment prediction assessment, treatment response assessment, treatment planning and guidance, and restaging/surveillance.

It is now generally believed that QR when brought to routine clinical practice will spawn numerous new advances in medicine, particularly in the field of cancer. Image segmentation is an essential underpinning for any effort to derive quantitative information from medical images. Given that there is overwhelming evidence in the segmentation literature that prior anatomic and modality-specific image appearance information is essential for effective object segmentation, it is ironic that no effort has been undertaken to date to establish, for public use, a comprehensive databank of such prior knowledge for the entire human body covering the entire adult population. We suggest that there should be a special program initiated and funded by the National Institutes of Health (NIH) on this effort alone considering how difficult the problem is and its very broad potential impact. Considering the wide applicability such a knowledge bank can have on medical image analysis, the proposed less broad effort on developing the Virtual Aging Adult model ensemble VAA(B, S, G) and the associated methods will likely catalyze the generation of new knowledge and technical capabilities in the field of QR.

Precision Medicine (PM) is an emerging approach for disease treatment and prevention that takes into account individual variability in genes, environment, and lifestyle for each person. The president's PM initiative calls for collecting and analyzing a large collection of data from patients, including image data. Again, the methods similar to those associated with the proposed VAA ensemble will become essential for deriving object-specific and quantitative information from large collections of medical image data, as well as for standardizing reporting to optimize communication between diagnosticians, clinicians, and patients.

In an aspect of the present disclosure, an approach is described that explores how to decouple disease quantification (DQ) methods from explicit dependence on image segmentation. The idea is to express disease severity by designing disease mapping functions without performing partial volume correction and delineation of either objects or lesions. The parameters of the disease map are estimated from a set of training image data sets.

A novel disease quantification approach is described for PET/CT images without delineation of objects. In the demonstrated manual mode of recognition, whether at the object level or even at the lesion level, the method is least intrusive on the lesion itself in terms of human interaction needed and the actual quantification strategy.

Although the current methodology focuses on the cancer application, it has applicability to other major initiatives currently underway within the area of medical imaging and the applications served by those initiatives.

Image Data

Twenty phantom PET/CT scans were obtained based on a NEMA, NU-2 IQ phantom (manufactured by Data Spectrum, Durham N.C.), but with the central 5 cm diameter "lung" cylinder of the IQ phantom removed and the initial background activity level set to be equivalent to 15 mCi in a 70 kg patient, and the 271-day half-life of 68Ge after 6 months the activity of about 9.5 mCi. Body-wide 18F-2-fluoro-2-deoxy-D-glucose (FDG)-PET/CT scans are utilized in this study, as PET/CT is the most commonly used modality for molecular imaging of patients with cancer and provides image data that are quantifiable prior to and following treatment, allowing for individualized regional and global disease assessment of patients with cancer. All patient PET/CT images were selected from our health system patient image database by a board certified radiologist (Torigian) following approval from the Institutional Review Board at the Hospital of the University of Pennsylvania along with a Health Insurance Portability and Accountability Act waiver. PET/CT scans with 20 lung lesions and 20 liver lesions were used to illustrate the disease quantification approach. The leave-one-out strategy is used for evaluation.

Methods

Figure 8:
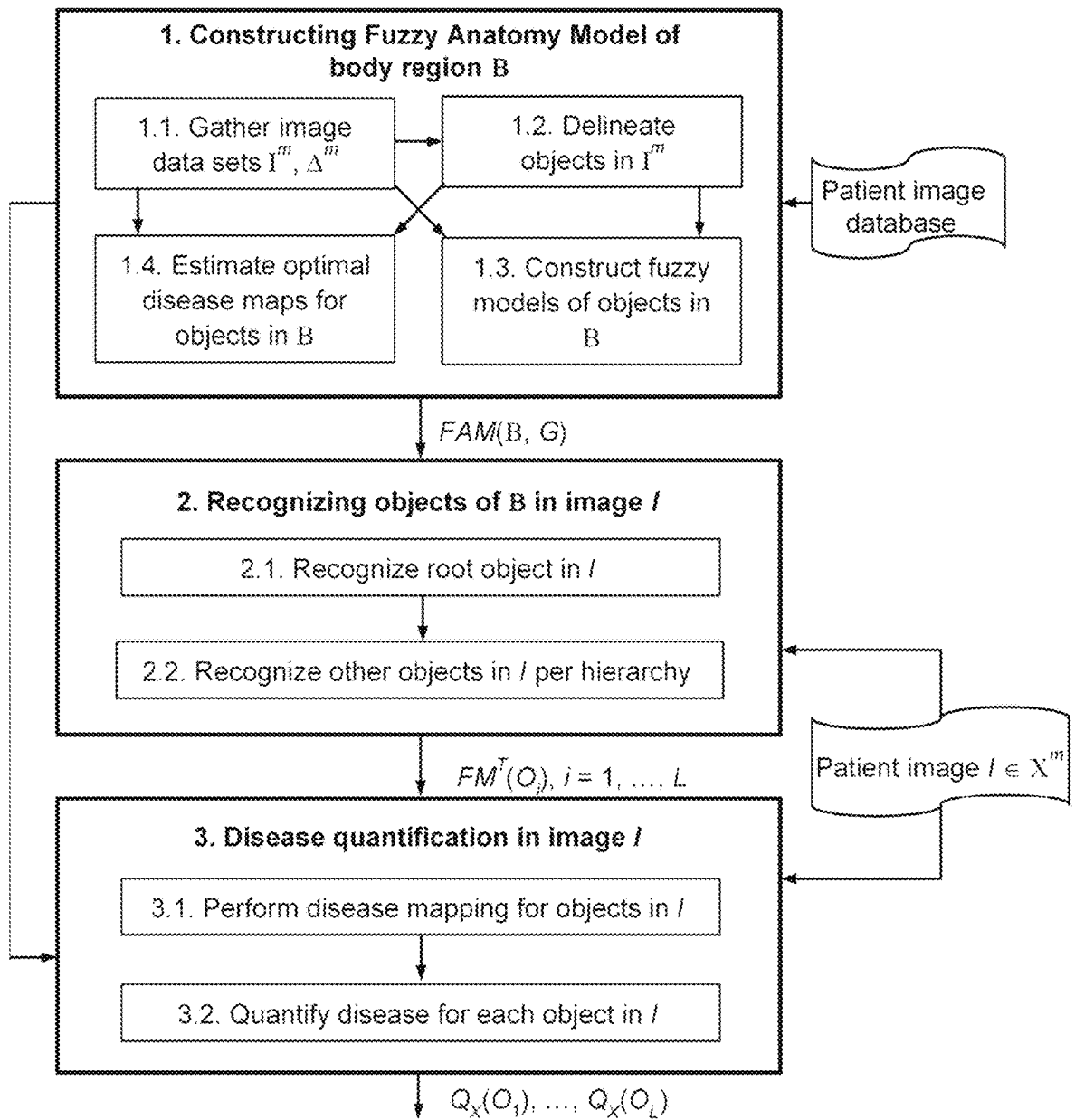
FIG. 8 is an example schematic representation of an AAR-DQ process.

In an aspect, The AAR-DQ methodology, schematically illustrated in FIG. 8, starts off with the AAR approach for modeling anatomy and automatically recognizing objects on low-dose CT images of PET/CT acquisitions. It incorporates novel aspects of model building that relate to finding an optimal disease map for each organ. The result of recognition for an object on a patient image I is the location of a fuzzy model for the object which is optimally adjusted for I. The model is used as a fuzzy mask on the PET image for estimating a fuzzy disease map for the specific patient and subsequently for quantifying disease based on this map. This process handles blur arising in PET images from partial volume effect entirely through accurate fuzzy mapping to account for heterogeneity and gradation of disease content at the voxel level without explicitly performing correction for the partial volume effect. Disease quantification is performed from the fuzzy disease map in terms of volumes and SUV statistics. We also demonstrate that the method of disease quantification is applicable even when the "object" of interest is recognized manually with a simple and quick action such as interactively specifying a 3D box ROI. Experimental evaluation studies are carried out on phantoms with known radiotracer concentrations as well as on patient PET/CT images where manual disease measurement is taken as the reference standard ground truth for comparison with results from the AAR-DQ approach.

The AAR-DQ approach has the following unique features: (1) It decouples dependence on explicit segmentation (delineation) of the organ and diseased tissue regions and performs DQ directly from object location information found automatically. This makes the disease quantification process robust, efficient, and practical. (2) It takes a fuzzy approach for handling uncertainties for object modeling, object recognition, disease mapping, and disease quantification, which obviates the need for explicitly correcting for phenomena such as the partial volume effect. (3) By the characteristics of the AAR approach, AAR-DQ is not tied to any specific object, and hence is applicable body-wide.

The present disclosure includes at least the following aspects (i) The concept of conspicuous and non-conspicuous lesion level disease quantification as well as corresponding results. (ii) A more comprehensive Introduction with a general and deeper literature review of disease quantification on PET/CT. (iii) A detailed description of the complete framework of AAR for DQ, a description of the complete family of AAR-DQ approaches including DQ-AO, DQ-MO, and DQ-ML strategies. (iv) Extensive experimental results at object level and lesion level, including conspicuous and non-conspicuous lesions. (v) A comprehensive comparison with other current methods.

Anatomy Recognition

Certain terminology may be referenced herein and is noted below:

G: The patient population group under consideration.

B: The body region of focus, in our case the upper body torso (i.e., thorax and abdomen combined).

$O_1, \ldots, O_L$: L objects or organs of B.

$I^m = \{I_1^M, \ldots, I_N^m\}$: A set of training images in modality m of body region B from N subjects in group G which are used for constructing models. In our case, $m \in \{CT, PET\}$, where CT refers to the low-dose CT image of PET/CT acquisitions. We assume that the images in $I^m$ are near normal and that the CT and PET images of the same PET/CT acquisition are in registration.

$I_b = \{I_{n,l}: 1 \leq n \leq N \ \& \ 1 \leq l \leq L\}$: The set of all binary images used for model building, $I_{n,l}$ being the binary image representing object $O_\lambda$ in image $I_n^m$. Since CT and PET images are in registration, binary image $I_{n,l}$ is applicable as a mask for object $O_\lambda$ in both $I_n^{CT}$ and $I_n^{PET}$.

FM($O_\lambda$): Fuzzy model of object $O_\lambda$ derived from the set of all binary images of $O_\lambda$.

$d_O(x)$: Disease map associated with object O. It maps SUV x at a voxel v within O to disease severity at von a [0, 1] scale.

$D^m = \{D_1^m, \ldots, D_K^m\}$: A set of training images in modality $m \in \{CT, PET\}$ of patients in group G with disease. These data will be used for estimating (training) the parameters of the disease map $d_O(x)$ for each object O.

$C^m = \{C_1^m, \ldots, C_M^m\}$: A set of test images in modality $m \in \{CT, PET\}$ of patients in group G with disease. These data will be used for testing the AAR-DQ approach.

FAM(B, G): Fuzzy anatomy model of the whole object assembly in B which includes all prior information gathered about objects such as the hierarchical arrangement of objects, their SUV properties, disease maps, object relationships, fuzzy models, etc.

$FM^T(O)$: Transformed FM(O) corresponding to a state when O is recognized in a patient image. $Q_X(O)$: A set of quantitative measures[8] describing the disease of O.

[8] Notation $Q_X$ is fashioned after notations $D_X$ and $R_X$ commonly used for diagnostics and therapeutics, and is intended to denote quantitative disease analytics.

Constructing Anatomy Model of the Body Region

Gathering images: images were selected from our health system patient image database by a board-certified radiologist (co-author DAT) following approval from the Institutional Review Board at the Hospital of the University of Pennsylvania along with a Health Insurance Portability and Accountability Act waiver. For the normal set $I^m$, the whole-body FDG-PET/CT images selected were near normal with exception of minimal incidental focal abnormalities such as cysts, small pulmonary nodules, etc. For abnormal sets $\Delta^m$ and $X^m$, the same radiologist selected whole-body FDG-PET/CT images of patients with various types of metastatic cancer involving multiple organ systems. The combined patient data set $\Delta^m \cup X^m$ included 31 patients in total with age 60.8±9.8 yrs and normal subject data sets ($I^m$) included 16 subjects in total with age 44.7±10.2. All data sets included both CT and PET images.

Delineating objects: As per AAR methodology, anatomic body regions and the organs in them are precisely defined first (see Table 1 in (Udupa et al., 2014) and Table 2 in (Wang et al., 2016)). All objects are then delineated following these definitions, strict tracing protocols, and scrutiny of delineations as described in (Udupa et al., 2014; Wang et al., 2016). This step generates the set of binary images $I_b = \{I_{n,l}: 1 \leq n \leq N \ \& \ 1 \leq l \leq L\}$ from the input set of images $I^m$. The tracings are done on the CT images of this set.

Constructing fuzzy models: We will focus on the following objects in the body torso in this paper for demonstrating the new ideas underlying disease quantification. The AAR-DQ approach is applicable to other and any number of objects if they can be recognized with adequate accuracy. BT: Upper body torso, which is made up of thoracic and abdominal body regions. BTSkn: The outer boundary of the body torso skin, the interior of which constitutes the upper body torso region. TSkn and ASkn: Similar to BTSkn but defined for the thoracic and abdominal body regions, respectively. LPS, RPS: Left and right pleural spaces including lungs, respectively. PS: Pleural spaces including T lungs=LPS+RPS. Lvr: Liver. As in previous AAR methods, all objects considered in this work include their interior 3D region and not just the boundary.

The Fuzzy Anatomy Model FAM(B, G) is defined by 5 entities:

$$FAM(B, G) = (H, M, \rho, \lambda, \eta). \quad (1B)$$

For a detailed description of these parameters, see (Udupa et al., 2014). Briefly, H is a hierarchy of objects in B, represented as a tree. This tree structure permits imposing an order among objects and allows encoding non-linear and very detailed anatomic information about the population into the model. M is a set of fuzzy models, one model for each of the L objects in B, $M = \{FM(O_k): k=1, \ldots, L\}$. $\rho$ describes the parent-to-offspring relationship in H over the population. $\lambda$ is a family of scale factor ranges. $\eta$ denotes a set of measurements pertaining to the object assembly in B including intensity properties and all learned parameters that are needed for object recognition and disease quantification.

Figure 9:
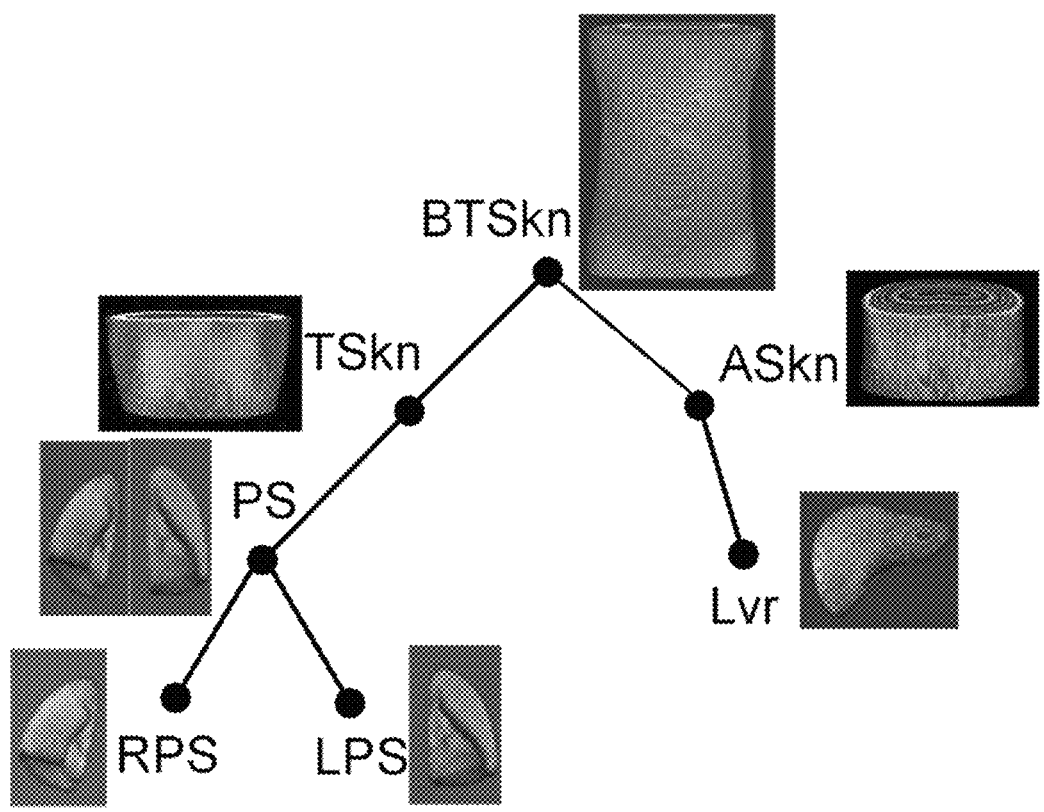
FIG. 9 illustrates an example hierarchy chosen for objects.

The object hierarchy H depicted in FIG. 9 was chosen for constructing FAM(B, G), where 3D renderings for different parts (object models) are illustrated. Fuzzy object model building will follow the hierarchy H by starting from root object of BTSkn, and then to other offspring objects. Recognition in the following section 2.2 will also follow the same hierarchy. The fuzzy model set M is built from training binary images in the set $I_b$ as described in (Udupa et al., 2014). This process consists of estimating the mean shape length and mean geometric center over all samples in $I_b$ of each object $O_\lambda$, repositioning all samples of $O_\lambda$ to this mean position, and rescaling them to mean shape length. Subsequently, a distance transform is applied to each resulting sample, and the average distance of the samples is computed and transformed to a fuzzy object membership value. From the repositioned and resized samples, the parent-to-offspring relationship $\rho_\lambda$ of $O_\lambda$ with respect to its unique parent in the hierarchy is estimated. Similarly, the size variation bounds $\lambda = \{\lambda_\lambda : 1 \leq \lambda \leq L\}$ over all samples are estimated from the same samples using the shape length of each $O_\lambda$.

The fifth element $\eta$ of FAM (B, G) stores values of parameters needed for object recognition and disease quantification. The parameters for object recognition are estimated as described in (Udupa et al., 2014; Wang et al., 2016). Briefly, apart from hierarchy H, fuzzy model set M, object relationship $\rho$, and scale variation $\lambda$, the only additional parameter needed is the optimal threshold $Th_\lambda$ for each object $O_\lambda$. These parameters are estimated from image sets $I^m$ and $I_b$ by using Algorithm OTE described in (Wang et al., 2016). $Th_\lambda$ is estimated by searching for a threshold interval that maximally separates the histogram of $O_\lambda$ from the histogram of the complement of $O_\lambda$ over all images in $I^m$. In our case, m=CT, that is, we use the CT image for object recognition.

Estimating optimal disease maps: For any PET image I, let $I_S$ denote the corresponding SUV image as defined by (Torigian et al., 2011)

$$I_S(v) = \frac{I^c(v)}{ID/BW}, \qquad (2B)$$

where ID is the injected dose of the radiotracer (expressed in MBq), BW is the body weight of the patient (expressed in g) whose acquired PET image is I, and $I^c(v)$ denotes the radioactivity concentration (expressed in MBq/cc where we assume 1 cc of tissue weighs 1 g) measured at voxel v of I which is corrected for decay from the time of injection to the time of image acquisition.

For disease quantification, we will employ a parametric function called disease map, denoted $d_O(x)$ which maps SUV value x at any voxel within object O to disease severity value on a [0, 1] scale. This map is intended to be specific to object[9] O. The parameters of $d_O(x)$ will be estimated as explained below. Let $\mu_n^o$ and $\sigma_n^o$ be the mean and standard deviation of SUV within normal object O as determined from normal image set $I^{PET}$, binary image set $I_b$, and the corresponding SUV images $I_S$.

[9] Implicit in our assumption is the fact that the map is specific to a particular disease of O, which in the current study is cancer. Multiple other disease conditions will be considered in our future work.

Disease map $d_O(x)$ is modeled as $d_O(x)=\max[0, g_d(x)-g_n(x)]$, where $g_d(x)$ and $g_n(x)$ are half and full Gaussians with parameters $(\mu_d^o, \sigma_d^o)$ and $(\mu_n^o, \sigma_n^o)$, respectively. Our intent is that $g_n(x)$ describes the SUV distribution within the normal tissues of object O, and $g_d(x)$ expresses SUV-to-degree-of-disease relationship for O.

$$g_d(x) = \begin{cases} \exp[-(x-\mu_d)^2/2\sigma_d^2], & \text{if } x < \mu_d \\ 1, & \text{if } x \geq \mu_d \end{cases}, \qquad (3B)$$

$$g_n(x) = \exp[-(x-\mu_n)^2/2\sigma_n^2].$$

The disease map $d_O(x)$ removes any contributions from normal tissue to the "degree of disease". When $g_d(x)<g_n(x)$, $d_O(x)$ is forced to be equal to zero to guarantee that the value of $d_O(x)$ is within [0, 1]. Assume for now that parameters $(\mu_d^o, \sigma_d^o)$ and $(\mu_n^o, \sigma_n^o)$ have been determined (see below for estimation method). The total disease burden within O is described in terms of total lesion glycolysis (TLG) defined as follows.

For any object O in any PET image I in $\Delta^m$, let $TLG_O(I)$ denote the (true) total lesion glycolysis of all lesions of O in I as determined by a reference method; that is, $TLG_O(I)$ is the sum over all lesions of the product of the lesion volume and its mean SUV. Our goal is to arrive through $d_O(x)$ at an estimate of the total disease burden of O that is as close as possible to $TLG_O(I)$. The disease quantity estimated by the AAR-DQ approach will be called fuzzy total lesion glycolysis of O in I, denoted $fTLG_O(I)$. The definition of $fTLG_O(I)$ requires the specification of a region within I. This region may be the whole image domain, an entire body region, or any specified ROI (binary or fuzzy), including in particular the fuzzy model $FM^T(O)$ of O localized in I by the AAR recognition step. Keeping these possibilities in mind, we denote such a general "ROI" specified in I by A and use the notation A(v) to denote the membership of voxel v of I in the ROI to allow for A to be also a fuzzy ROI such as $FM^T(O)$. Thus, when A is a binary mask, $A(v)\in\{0, 1\}$, and when A is fuzzy, $A(v)\in[0, 1]$. The traditional approach for calculating TLG is first to obtain a binary lesion mask by applying a thresholding or hard segmentation operation on every voxel where partial volume effect occurs, and then utilizing the binary mask, which usually covers a smaller region than the original region used, for TLG estimation. In this paper, we consider a fuzzy volume instead. Some voxels would be discarded in the traditional approach after segmentation such that there can be no contribution from them to TLG. Yet, those voxels may still contribute to TLG and hence should not be discarded, and so their contribution can instead be described by using fuzzy membership followed by disease map as we describe in this paper.

With this generality, for the disease under consideration, we define the fuzzy total lesion glycolysis within an ROI A, denoted $fTLG_A(I)$, in a PET image I by $$fTLG_A(I) = \upsilon \sum_{all\, v\, in\, A} d_O(I_S(v))I_S(v)A(v). \qquad (4B)$$

In words, $fTLG_A(I)$ (expressed in cc) is a weighted sum of the SUV values of voxels within mask A multiplied by the voxel volume $\upsilon$ (expressed in cc), assuming all voxels are of the same size. There are two weights for each voxel—A(v), which is the mask weight, and $d_O(x)$, which is the disease weight based on the SUV $I_S(v)$ at v. Of course, $d_O(I_S(v))$ is unknown at this point at v. Along similar lines, to accommodate a general (hard) mask A, we modify the previously defined true total lesion glycolysis $TLG_O(I)$ within object O to $TLG_A(I)$ such that the latter denotes the sum of the true total lesion glycolysis of all lesions within binary mask A.

The map $d_O(x)$ is completely determined by $\mu_d^o$ and $\sigma_d^o$. Our idea is to estimate the parameters of $d_O(x)$ optimally so that the disease weight expressed by $d_O(x)$ brings our estimate $fTLG_A(I)$ of the disease burden as close as possible to the true estimate $TLG_A(I)$. We perform this estimation by optimizing the following function.

$$(m_d^O, s_d^O) \in \genfrac{}{}{0pt}{}{\arg\min}{\mu_d^O, \sigma_d^O} \left[ \sum_{I \in \mathcal{D}^m} (TLG_A(I) - fTLG_A(I))^2 \right]. \qquad (5B)$$

The optimal parameters of $d_O(x)$ are denoted by $(m_d^O, s_d^O)$. We find the optimal parameters using Powell's NEWUOA software (Powell, 2006).

The fuzzy treatment in disease quantification allows for handling both the segmentation issue of deciding whether or not a voxel belongs to a lesion as well as the determination of the SUV measurement at each voxel without explicit partial volume correction and binary segmentation commitment.

Estimation of the disease map $d_O(x)$ requires parameters $\mu_n^o$ and $\sigma_n^o$, which in turn need data sets $I^{CT}$ and $I^{PET}$. We estimate $\mu_n^o$ and $\sigma_n^o$ directly from sets $I^{PET}$ and $I_b$. Estimating $TLG_A(I)$ requires data sets $\Delta^m$, $m\in\{CT, PET\}$, and is challenging at the lesion level, and hence at organ level, mainly because of the extreme variability of the fuzziness of the lesions. We take the approach described below to establish $TLG_A(I)$.

Figure 10:
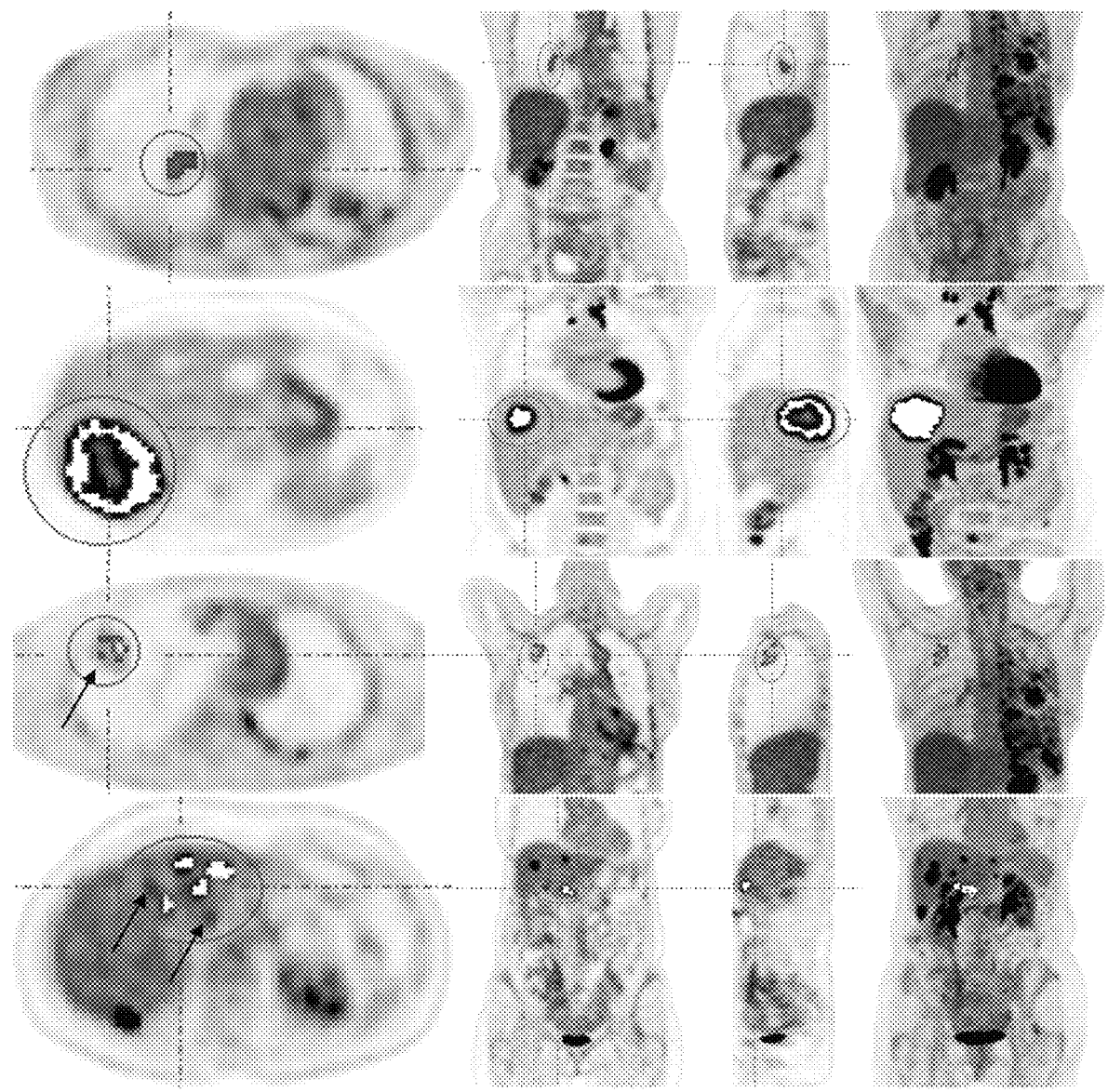
FIG. 10 illustrates examples of conspicuous and non-conspicuous lesions of the lung and liver on PET images.

Establishing true disease measurements: Commercial clinical software systems generally require a human operator to specify an ROI manually corresponding to each lesion to be quantified on the PET image. As illustrated in FIG. 10, the ROI should be specified fairly close to the lesion boundary on a slice, and the extent of the ROI in the third dimension orthogonal to the slice plane should also be indicated. The software then generally performs an iterative thresholding operation, sometimes with partial volume correction depending on the particular software system, and outputs the volume of the lesion, commonly known as metabolic lesion volume (MLV) (expressed in cc), mean and maximum SUV of the lesion, and then a product of MLV and mean SUV of the lesion called total lesion glycolysis (TLG) (expressed in cc).

We used one such software system called ROVER (Hofheinz et al., 2007a and 2010b) for generating reference true measurements. We found this software to be adequate for use in the above manner for large, well-defined, and focal lesions. We refer to such lesions which can be delineated automatically by the clinical software via an ROI without requiring parameter adjustment and whose segmentations seem visually accurate as conspicuous lesions. However, the behavior of this software was generally not stable for lesions that are not well-defined, large, or focal. Accordingly, those lesions whose delineation by the clinical software requires manual adjustment of parameters or delineations on a per-lesion basis will be referred to as non-conspicuous lesions. For conspicuous lesions, we generated true measurements by using the clinical software. For non-conspicuous lesions, we created reference measurements by individually thresholding each lesion on the PET image to produce visually optimal results under the guidance of an expert radiologist (DAT) who has over 10 years of experience in making such measurements clinically. Examples of conspicuous and non-conspicuous lesions are shown in FIG. 10. As shown in the two bottom rows, non-conspicuous lesions labeled via arrows in the ROIs (circles/ovals) may be over-segmented or under-segmented or missed when using clinical software, subsequently requiring manual adjustment.

In summary, at the end of the model building step (see FIG. 8), we have a fuzzy anatomy model FAM(B, G) of the body region B complete with anatomic information encapsulated in H, M, ρ, and λ, and disease map information included in η for the particular disease being studied for each object of B.

Recognizing Objects

We will use both manual and automatic recognition strategies. In the manual mode, we will present two methods, one at the object level and another at the lesion level, and in both, one ROI A will be specified by using rectangular boxes[10] to keep the manual recognition and specification of A simple and efficient. For further reference, we will denote these manual methods by MO and ML, respectively; in MO, the object is specified by a given mask, such as rectangular box just enclosing the object, and in ML, the box specified just encloses each lesion. The goal of the MO method is to demonstrate that, albeit manual, it can be used to efficiently and accurately quantify the total disease burden within an object via the proposed approach. This is currently not feasible by employing clinically available software systems. The current manual way of quantifying each lesion on its own is not practical when lesions and/or involved organs are numerous. The goal of the ML method is to demonstrate that even when each lesion is identified manually, the proposed approach performs quantification accurately. In both manual methods, the ROI A for disease quantification is a binary mask.

[10] The ROI mask does not need to be rectangular; in fact, it can be any given shape to localize the target object. CAVASS software (Grevera et al., 2007) supports an efficient way for generating such a mask, which involves manually drawing an ROI on a single slice and then propagating it to other slices automatically.

The real thrust of this manuscript is on the automatic mode at the object level, which we will denote by AO, wherein objects are recognized automatically by the AAR approach. We are not introducing any new concepts in this paper over those in (Udupa et al., 2014; Wang et al., 2016) for organ recognition per se. The process follows the recognition algorithms of (Udupa et al., 2014; Wang et al., 2016) and starts off by first recognizing the root object and then follows the hierarchy displayed in FIG. 9 to locate other objects. The output of the automatic recognition step is the modified fuzzy model $FM^T(O)$ for each object O optimally adjusted to the manifestation of O in the CT image of the given PET/CT pair. In other words, in this case, the ROI for object O for disease quantification is a fuzzy mask $A=FM^T(O)$.

In summary, one or more of the three methods of recognition—manual at object level (MO), manual at lesion level (ML), and automatic at object level (AO) may be used to define the mask A needed for disease quantification.

Quantification

We will denote the disease quantification procedures for the three recognition methods AO, MO, and ML by DQ-AO, DQ-MO, and DQ-ML, respectively. For recognition method MO, the procedure DQ-MO is the same as DQ-AO except that in Step 1, objects are identified manually, dilation in Step 3 is not performed, and the specified ROI is to be considered as a binary mask A. For DQ-ML, "object" is to be interpreted as a lesion and then the procedure DQ-MO is to be followed. In this case, L indicates the number of lesions quantified.

In procedure DQ-AO, each anatomic object O is first recognized or localized in the CT image automatically. The fuzzy model $FM^T(O)$ found in this process is then dilated[11]. The resulting fuzzy mask, called A, is then applied to the SUV image derived from the input PET image. The disease map $d_O(x)$ of O is retrieved from the element η of FAM(B, G) and the total disease burden $fMTV_O$ of O is computed via Equation 4B. The contribution from each voxel within the localized object is weighted by the level of disease at the voxel and the level of certainty for the voxel to belong to O. For manual methods MO and ML, the weight of belongingness to the object is binary but the weight of disease severity coming from $d_O(x)$ is fuzzy. Note that, for methods MO and ML, there may be voxels in the binary mask A that are outside the object proper which will be weighted by 1. However, if the disease map is accurate for O, such voxels will

---

Procedure DQ-AO
Input: An image pair $(I^{CT}, I^{PET})$ of B from the set $X^m$ and FAM(B, G).
Output: $Q_X(O_i)$, i = 1, . . . , L.
Begin
1. Recognize objects $O_i$, i = 1, . . . , L, in $I^{CT}$;
2. For each object $O_i$, do
3.     Perform gray-level dilation of $FM^T(O_i)$ and let the result be A;

-continued

4. Compute $SUV_{mean}$, $SUV_{max}$, and $fTLG_A(I^{PET}) = \upsilon \sum_{all\ v\ in\ A} d_O(I_S^{PET}(v))I_S^{PET}(v)A(v)$, where $\upsilon$ denotes the volume of a voxel in A;
5.    $Q_X(O_i) = [SUV_{mean}(A), SUV_{max}(A), fTLG_A(I^{PET})]$;
6.    EndFor;
7.    Output $Q_X(O_i)$, i = 1, . . . , L;
End receive negligible disease weight from $d_O(x)$. Finally, the output of the procedure for each object consists of the object's $SUV_{Mean}$ and $SUV_{Max}$ and its estimated $fTLG_A$ value with the appropriate interpretation of the meaning of these entities as explained above for the cases of DQ-AO, DQ-MO and DQ-ML.

[11] The purpose of the dilation operation is to make sure that the object is fully covered by the model fuzzy mask. We perform dilation by 10 mm which roughly corresponds to AAR's object localization error.

In summary, we have described three methods for disease quantification in a single general framework: DQ-AO, DQ-MO, and DQ-ML. DQ-AO and DQ-MO perform disease quantification at the whole object (organ) level, with DQ-AO recognizing objects automatically and DQ-MO localizing objects manually. DQ-ML performs quantification at the lesion level, after an ROI is specified manually for each lesion for its recognition. DQ-ML is not a practical method, but it is included since it is similar to current clinically used software in terms of the manual labor required. DQ-AO is an automatic production-mode strategy, whereas DQ-MO is a less automated but yet practical method.

Experiments, Results, Discussion

We conducted experiments on phantom data, where the true quantity of "disease" is known, as well as on patient data, where "true" disease is established by employing a clinically used commercial software system as described above.

Phantom Data

We have utilized the publicly available National Electrical Manufacturers Association (NEMA) PET phantom data sets for studying the behavior of our proposed DQ strategies whose specifications are as follows.

The phantom data sets contain 20 scans previously acquired on a PET/CT scanner (Discovery STE, General Electric, Waukesha, Wis.) using a NEMA NU-2 IQ phantom (Mansoor et al., 2014; Kohlmann et al., 2015) (Data Spectrum, Durham N.C.). The central 5 cm diameter "lung" cylinder had been removed, the initial background activity level had been set to be equivalent to 15 mCi in a 70 kg patient, and the background activity level was approximately 9.5 mCi after 6 months (given the 271-day half-life of $^{68}$Ge). Six hollow spherical inserts (with diameters of 37, 28, 22, 17, 13, and 10 mm to simulate lesions of different sizes) were used, all of which had an activity target-to-background ratio of 4:1. Additional details pertaining to the phantom and PET/CT image acquisition are summarized in Table B1.

TABLE B1

NEMA phantom and PET/CT image acquisition details.

| | |
|---|---|
| Phantom weight | 10.9 kg |
| Isotope | $^{68}$Ge |
| Pre-injection amount of radioactivity | 4.54 mCi |
| Activity target-to-background (T/B) ratio | 4:1 |
| Scanner | GE Discovery STE-16 PET/CT scanner |
| PET scan duration | 5 minutes |
| PET voxel size/scene size | 2.73 * 2.73 * 3.27 mm/128 * 128 * 47 |
| CT voxel size/scene size | 0.68 * 0.68 * 2.50 mm/512 * 512 * 63 |
| CT tube voltage | 120 kV |
| Field-of-view (PET and CT) | 350 mm |

Figure 11:
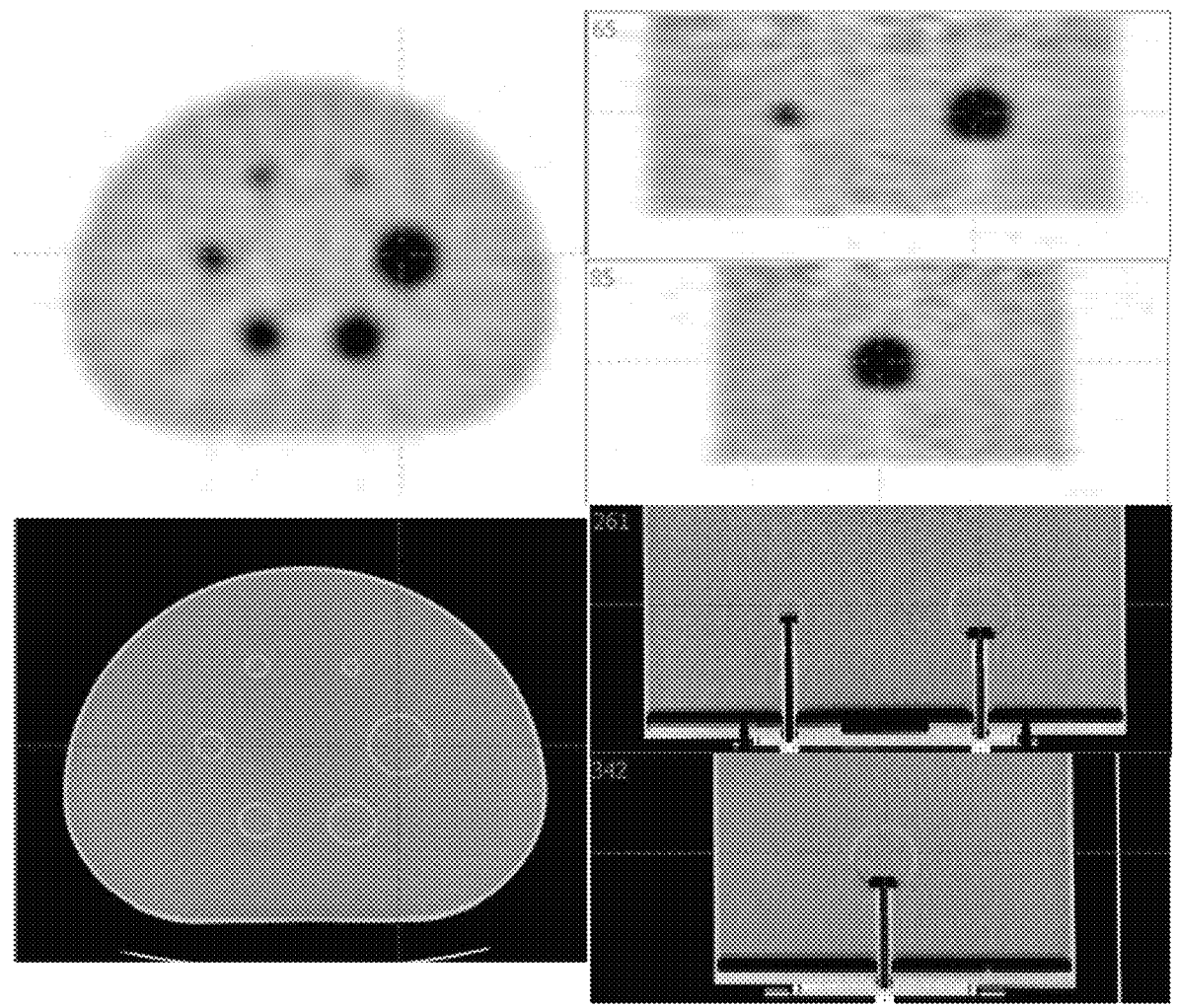
FIG. 11 illustrates example PET images (top row) and CT images (bottom row of NEMA phantom showing 6 spherical inserts displayed in axial (left column), sagittal (right column top), and coronal (right column bottom) planes.
Figure 12:
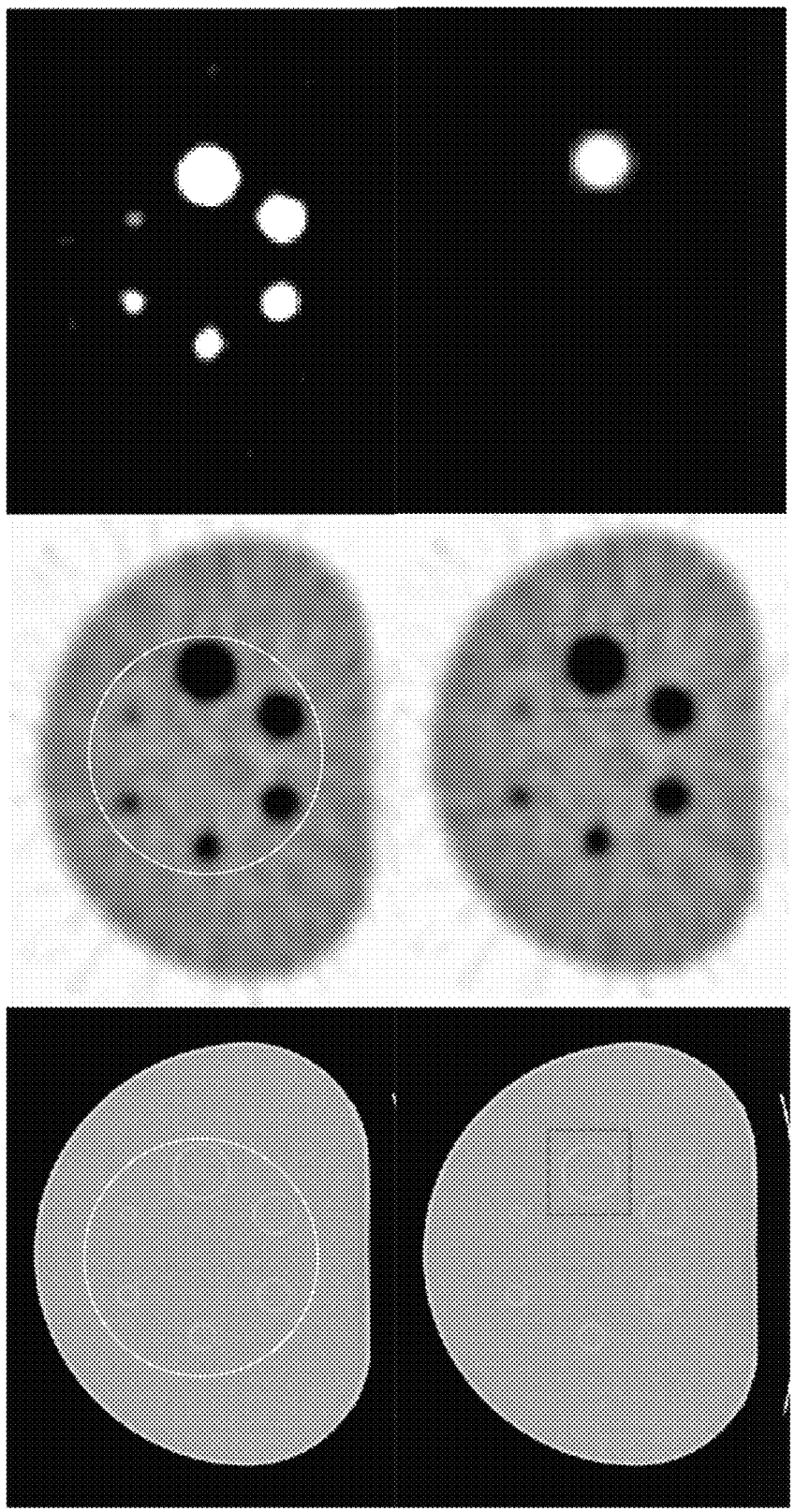
FIG. 12 illustrates examples of manual recognition and the resulting fuzzy disease maps.

Within the phantom, we consider each separate spherical insert (with its radioactive contents) as a "lesion", and different groups of spherical inserts (with their radioactive contents) including portions of the background as "objects" (i.e., "organs") for the purpose of testing lesion-level and object-level methods. Representative PET and CT images of the phantom are shown in different imaging planes in FIG. 11. Since automatic recognition by the AAR process is not relevant for phantoms, we tested methods DQ-MO and DQ-ML only. For DQ-MO, we specified one circular ROI to enclose all individual "lesions" (i.e., spherical inserts) going through all slices that encompassed the spherical inserts, the idea being that the ROI would encompass an "organ" (including background and spherical inserts) to emulate the process of quantifying all "lesions" within an organ collectively. For DQ-ML, a rectangular ROI was specified around each of the "lesions" (i.e., spherical inserts). The processes of specifying ROIs at the "organ" and "lesion" level for the phantom data set are illustrated in FIG. 12 for methods DQ-MO and DQ-ML. This figure also demonstrates the fuzzy disease maps obtained at the organ level and lesion level by these methods.

Some discussion is in order regarding how to establish true $Q_X$ values for phantom data. For these data, the actual radiotracer activity is known and so also the volume of every sphere. Thus, it is possible to calculate the theoretical absolute true TLG value for each "lesion". However, since we thought it is prudent to estimate disease maps in exactly the same way for phantoms as for patient data sets, the disease maps for phantoms were "trained" on PET images as in the case of patient studies. One consequence of training on PET images is that TLG estimated by our method will always be (much) lower than the theoretical true value since the activity level in the "lesions" will be always lower than the actual value, especially much lower for small "lesions". An alternative approach would be to "train" our method on true theoretical activity rather than on the activity observed in the PET images. This can be accomplished by making appropriate changes to Equations 3 and 5. We chose not to pursue this direction for two reasons. Firstly, it would be impossible to train on the theoretical true activity values in patient studies since these values are impossible to establish at lesion level and even at object level. Secondly, this would have made the actual process of DQ itself and its evaluation different for phantoms and patient cases. Therefore, we decided to establish "true" $Q_X$ values for phantom cases by using the activity values actually observed in the PET images but estimated by using the known true "masks" of the spheres in PET images in the spirit of avoiding the big hurdle of lesion segmentation.

TABLE B2

Mean and standard deviation of % errors in TLG estimation on phantom PET/CT scans for "lesions" and "organs" using the DQ-ML and DQ-MO methods.

| | | Method | | | | | | |
|---|---|---|---|---|---|---|---|---|
| | | DQ-ML | | | | | | DQ-MO All spherical inserts |
| Spherical insert diameter (mm) | | 37 | 28 | 22 | 17 | 13 | 10 | included |
| TLG error | Absolute (cc) mean (SD) | 4.66 (2.98) | 8.70 (3.09) | 7.99 (1.75) | 4.53 (0.81) | 1.69 (0.29) | 0.45 (0.36) | 21.99 (7.70) |
| | % mean (SD) | 1.93 (1.24) | 9.10 (2.99) | 19.18 (3.52) | 32.15 (4.68) | 34.43 (6.59) | 36.96 (7.38) | 5.82 (1.86) |
| $SUV_{Mean}$ error | Absolute mean (SD) | 0.39 (0.09) | 0.64 (0.08) | 0.75 (0.09) | 0.56 (0.08) | 0.23 (0.05) | 0.09 (0.09) | 0.21 (0.11) |
| | % mean (SD) | 3.86 (0.89) | 7.11 (0.97) | 9.37 (1.28) | 8.24 (1.19) | 3.89 (0.98) | 2.04 (2.00) | 2.22 (1.20) |
| $SUV_{Max}$ error | Absolute mean (SD) | 0.00 (0.00) | 0.00 (0.00) | 0.00 (0.00) | 0.00 (0.00) | 0.00 (0.00) | 0.00 (0.00) | 0.00 (0.00) |
| | % mean (SD) | 0.00 (0.00) | 0.00 (0.00) | 0.00 (0.00) | 0.00 (0.00) | 0.00 (0.00) | 0.00 (0.00) | 0.00 (0.00) |

We used a leave-one-out (LOO) strategy to evaluate the performance of our DQ approaches. In particular, there were 20 experiments in total where for each experiment, spherical inserts from 19 phantom PET/CT data sets were used to estimate the parameters of $d_O(x)$ and the remaining 1 data set was used to test the accuracy of quantitative parameters $Q_X$ by the proposed methods. Table B2 lists the mean and standard deviation of errors in estimating TLG, $SUV_{Mean}$, and $SUV_{Max}$ for "lesions" and "organs" within phantom data sets using DQ-ML and DQ-MO methods, where average error % is calculated as [(estimated value−ground truth value)/(ground truth value)]×100 over all tested samples for each method. For the DQ-MO method, where all "lesions" together are considered within an "organ", the average TLG error was ~6%. For the DQ-ML method, we observed that the estimates of TLG for small "lesions" had larger errors than those of larger "lesions", with average error ranging from 2% to 37%. At the lesion level, $SUV_{Mean}$ achieves error within 2%-9% and $SUV_{Max}$ achieves error close to zero for all lesions.

Lesions with small diameter have strong partial volume effect (compared to their size) and TLG error increases with decreasing sphere size. This has been previously observed by other methods tested on these phantoms (Kinahan et al., 2010; Doot et al., 2010), where the ratio defined by measured value/true value was found to be ~0.3 for small lesions. Expressed as % TLG error as we defined above, this error is ~70%. % TLG error is ~50% for lesions with diameter 13 mm, ~40% and 25% for larger lesions with diameter 17 mm and 22 mm, and ~3% for lesions with the maximum diameter 37 mm (Kinahan et al., 2010; Doot et al., 2010). Thus, although our method's performance is much poorer for small lesions than for large lesions, it still outperforms current approaches, especially on small lesions. We note that there is an issue in properly expressing error in measuring small lesions. Even small absolute errors (in cc) become exaggerated when expressed as a percent of the total lesion activity when lesions are small. A somewhat similar phenomenon occurs also for other metrics. This is the reason that we also listed absolute errors as well for all three measures in Table B2.

Patient Data

Body-wide FDG-PET/CT scans from human subjects were utilized in this study. Details about data sets $I^m$, $X^m$, and $\Delta^m$ are summarized in Table B3. We used 16 normal data sets in $I^m$ for building the AAR model. For estimating the parameters of the disease map, we again employed the LOO strategy—of the 31 patient data sets, 30 were used for training, one was set aside for testing, and the process was repeated 31 times.

TABLE B3

Summary of normal and patient PET/CT data sets used in this study.
Conspicuous lesions (40 in total) and non-conspicuous lesions (10 in total) are both included.

| Data set | Number of subjects, number & type of lesions | Scan details | Image size/voxel size |
|---|---|---|---|
| $I^m$ Normal | 16 (no lesions) | Whole-body, unenhanced, axial | PET: 144 × 144 × 338-443, 4 × 4 × 4 mm$^3$ CT: 512 × 512 × 338-443, 1.2 × 1.2 × 4 mm$^3$ |
| $\Delta^m$, $X^m$ Pathological | 7 (10 non-conspicuous lesions: 7 liver + 3 lung) | Whole-body or from skull base to proximal thighs, unenhanced, axial | PET: 200 × 200 × 326-440, 4.07 × 4.07 × 3.00 mm$^3$ CT: 512 × 512 × 326-440, 0.98 × 0.98 × 3.00 mm$^3$ |
| | 14 (20 conspicuous lung lesions) 10 (20 conspicuous liver lesions) | Whole-body or from skull base to proximal thighs, unenhanced, axial | PET: 200 × 200 × 326-440, 4.07 × 4.07 × 3.00 mm$^3$ CT: 512 × 512 × 326-440, 0.98 × 0.98 × 3.00 mm$^3$ |

All scans had previously been acquired on PET/CT scanners with time-of-flight capabilities (Gemini TF, Philips Medical Systems, Bothell, Wash.). 3D PET data had been acquired either from the skull vertex to the toes or from the skull base to the proximal thighs ~60 minutes after intravenous administration of ~555 MBq of FDG for ~3 minutes per bed position. Image reconstruction had been performed at 4 mm nominal slice thickness in the axial plane using a list-mode maximum-likelihood expectation-maximization (ML-EM) algorithm with 33 ordered subsets and 3 iterations, and the system model included time-of-flight as well as normalization, attenuation, randoms, and scatter corrections, where rescaled low-dose CT images were utilized for attenuation correction of PET images. All patient PET/CT images were selected from our health system patient image database by a board-certified radiologist (DAT) following approval for this study from the Institutional Review Board at the Hospital of the University of Pennsylvania along with a Health Insurance Portability and Accountability Act waiver. 20 conspicuous lung lesions and 20 conspicuous liver lesions were assessed to illustrate the disease quantification approach. We also assessed 10 non-conspicuous lesions (3 lung lesions and 7 liver lesions) for comparison of the disease quantification approach performance with that for conspicuous lesions. An LOO strategy was used for evaluation.

The objects (i.e., organs) considered were PS (LPS+RPS) (i.e., the lungs) and Lvr (i.e., the liver) in this initial study. Other objects shown in the hierarchy of FIG. 9 are needed for accurate recognition of the objects for which DQ is performed. Organ-level reference standard measurements were obtained by aggregating lesion-level reference standard measurements from all lesions within the organ of interest, with $SUV_{Mean}$ calculated as the mean of all lesion $SUV_{Mean}$ values, $SUV_{Max}$ as the maximum of all lesion $SUV_{Max}$ values, and $TLG_O$ as the sum of TLG values of all lesions within the organ.

Figure 13:
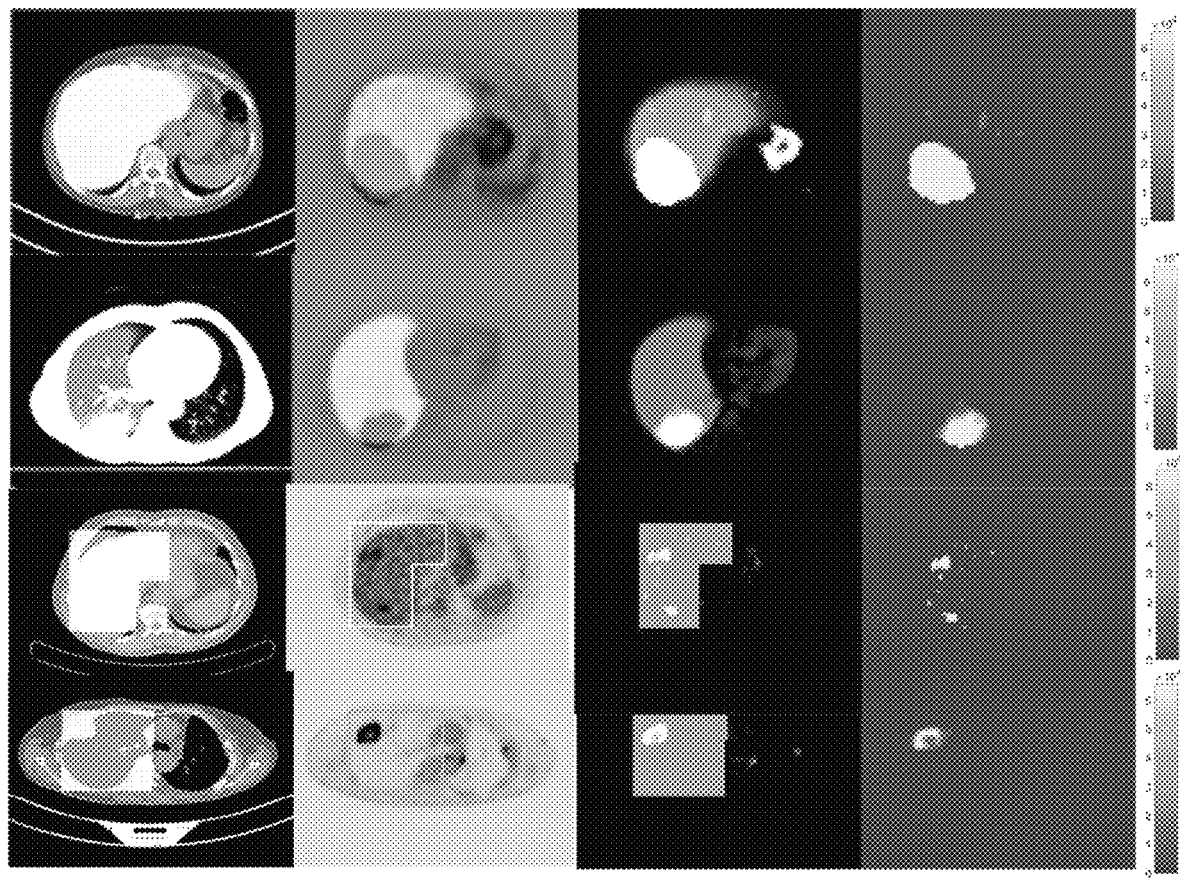
FIG. 13 illustrates examples of disease maps of metastatic cancer lesions estimated at the organ level by methods DQ-AO (top two rows) and DQ-MO (bottom two rows) for Lvr (liver) and RPS (right pleural space including right lung).
Figure 14:
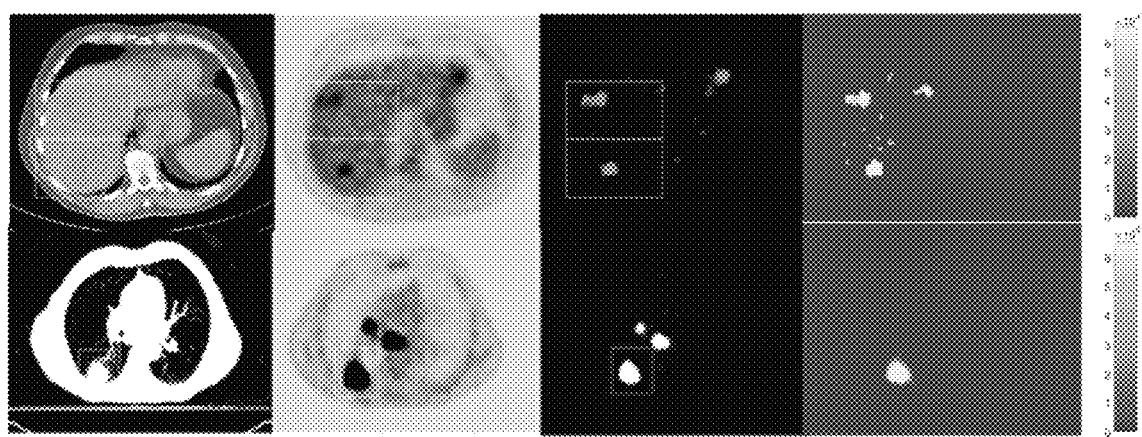
FIG. 14 illustrates examples of disease maps of metastatic cancer lesions estimated at the lesion level by method DQ-ML for liver lesions (top row) and lung lesions (bottom row).

Representative estimated disease maps of metastatic cancer lesions for liver and right lung are displayed in FIG. 13 for methods DQ-AO and DQ-MO. The recognized object fuzzy mask for DQ-AO and the specified binary object mask for DQ-MO are shown overlaid on the underlying CT and PET images in the top two rows. Similarly, FIG. 14 shows representative estimated fuzzy disease maps for method DQ-ML. As one can see from these examples, given appropriate ROI placement by AAR or by the manual approach for objects or lesions, the disease map within the ROIs can correctly capture conspicuous lesions within the ROIs.

TABLE B4

Mean and standard deviation of % errors and absolute errors in estimating
TLG, $SUV_{Mean}$, and $SUV_{Max}$ on patient PET/CT scans for all
lesions within the liver and lungs via DQ-MO and DQ-AO.

| | | Liver lesions | | Lung lesions | | All lesions | |
|---|---|---|---|---|---|---|---|
| | | | | Method | | | |
| | | DQ-MO | DQ-AO | DQ-MO | DQ-AO | DQ-MO | DQ-AO |
| TLG error | Absolute (cc) mean (SD) | 78.74 (93.92) | 105.70 (127.74) | 12.23 (22.60) | 21.65 (41.6) | 46.06 (66.67) | 67.49 (94.55) |
| | % mean (SD) | 11.30 (7.22) | 12.27 (8.85) | 9.55 (4.05) | 14.67 (9.24) | 9.81 (9.77) | 13.65 (11.75) |
| $SUV_{Mean}$ error | Absolute mean (SD) | 0.52 (0.41) | 0.42 (0.26) | 0.83 (1.01) | 0.69 (0.97) | 0.66 (0.57) | 0.62 (0.65) |
| | % mean (SD) | 12.62 (6.60) | 11.18 (6.59) | 18.59 (14.19) | 17.48 (9.57) | 16.23 (13.47) | 14.97 (13.79) |

TABLE B4-continued

Mean and standard deviation of % errors and absolute errors in estimating TLG, $SUV_{Mean}$, and $SUV_{Max}$ on patient PET/CT scans for all lesions within the liver and lungs via DQ-MO and DQ-AO.

|  |  | Liver lesions | | Lung lesions | | All lesions | |
|---|---|---|---|---|---|---|---|
|  |  | \multicolumn{6}{c}{Method} | | | | | |
|  |  | DQ-MO | DQ-AO | DQ-MO | DQ-AO | DQ-MO | DQ-AO |
| $SUV_{Max}$ error | Absolute mean (SD) | 0.50 (1.47) | 0.46 (1.37) | 0.56 (1.00) | 0.56 (1.00) | 0.47 (1.28) | 0.45 (1.22) |
|  | % mean (SD) | 0.39 (0.49) | 0.39 (0.49) | 0.07 (0.14) | 0.07 (0.14) | 0.26 (0.81) | 0.27 (0.80) |

Table B4 lists the mean and standard deviation of errors (absolute and %) in estimated disease quantities $Q_X$ (TLG, $SUV_{Mean}$, and $SUV_{Max}$) for patient lesions (including conspicuous and non-conspicuous types) within the liver and lungs using the DQ-AO and DQ-MO methods with respect to the quantities from the reference method over test data sets $X^{m12}$. Table B5 lists comparable results using the DQ-ML method on conspicuous lesions, and Table B6 shows results for the DQ-ML method separately for conspicuous and non-conspicuous lesions. As in Table B2, we list the absolute errors and % errors in Tables B4-6.

[12] The absolute errors for TLG may appear large in Table B4, but note that true TLG itself is very large at the organ level (in the 1000s) because of contribution from all lesions in the object region, and more importantly, due to multiplication of volume by SUV.

TABLE B5

Mean and standard deviation of % errors and absolute errors in TLG, $SUV_{Mean}$, and $SUV_{Max}$ estimation on patient PET/CT scans for individual conspicuous lesions within liver and lung via DQ-ML.

|  |  | Liver lesions | Lung lesions | All lesions |
|---|---|---|---|---|
| TLG error | Absolute (cc) mean (SD) | 5.06 (6.01) | 11.26 (23.07) | 8.23 (17.14) |
|  | % mean (SD) | 6.63 (3.78) | 11.83 (3.92) | 9.07 (3.86) |
| $SUV_{Mean}$ error | Absolute mean (SD) | 0.14 (0.11) | 0.58 (0.33) | 0.34 (0.33) |
|  | % mean (SD) | 3.80 (3.21) | 9.68 (7.13) | 6.71 (5.17) |
| $SUV_{Max}$ error | Absolute mean (SD) | 0.001 (0.003) | 0.00 (0.00) | 0.0001 (0.0002) |
|  | % mean (SD) | 0.04 (0.02) | 0.00 (0.00) | 0.02 (0.01) |

Referring to Tables B4-B6, one may observe the following. Disease quantification at the lesion level via the DQ-ML method generally had lower % errors than at the organ level via the DQ-MO or DQ-AO methods, and the errors were generally lower for liver lesions compared to lung lesions at the lesion level via the DQ-ML method. TLG estimation from the proposed approach achieved lower % error than for $SUV_{Mean}$ estimation. For all methods, the estimation of $SUV_{Max}$ was most accurate with less than 0.5% error.

For disease quantification at the organ level, TLG estimation via the DQ-MO method had lower % error than that via the DQ-AO method for liver lesions and higher error for lung lesions. $SUV_{Mean}$ estimation via the DQ-MO method had lower % error than via the DQ-AO method for both liver and lung lesions, whereas $SUV_{Max}$ estimation via the DQ-MO and DQ-AO methods had similar levels of error. However, none of the differences between DQ-AO and DQ-MO methods is statistically significant.

Table B6 shows that the proposed DQ-ML method has higher accuracy for conspicuous lesions than for non-conspicuous lesions, which is not surprising given the challenges in establishing ground truth measurements for non-conspicuous lesions. Yet, even for non-conspicuous lesions, the proposed approach for TLG, $SUV_{Mean}$, and $SUV_{Max}$ estimation was accurate in approximately 81%, 86%, and 100% of lesions in terms of % error.

Disease quantification at the object (organ) level without explicit object delineation on PET/CT images has not been previously reported in the literature, whereas almost all literature exists regarding PET/CT-based disease quantification at the lesion level. In our study, object level TLG estimation had a % error of 5.82%±1.86% via the DQ-MO method on PET/CT phantom data sets, and 9.81%±9.77% and 13.65%±11.75% via the DQ-MO and DQ-AO methods, respectively, on PET/CT patient data sets. At the lesion level, TLG estimation had an error ranging from 2%-37% via the DQ-ML method on PET/CT phantom data sets depending on the "lesion" size, and an error of 9.07%±3.86% on PET/CT patient data sets. These lesion level results are comparable to those from a most recent study by Taghanaki et al on PET/CT phantom data sets which utilized a multiple layer random forest tree method based on features extracted from 3D patches (very similar to deep learning approaches Taghanaki et al., 2018). This method reported an average relative absolute error of 12.17%±5.34% for lesion level TLG estimation, a relative absolute error of 13.83%±21.47% for estimating $SUV_{Mean}$ of lesions smaller than 2 mL in volume for patient data, as well as an error of 5.70±5.25% for estimating $SUV_{Mean}$ on NEMA phantom data. From our approach, $SUV_{Mean}$ error (2.22%±1.20%) and $SUV_{Max}$ error (close to zero) on the same phantom data are better than results in (Kinahan et al., 2010; Doot et al., 2010; Taghanaki et al., 2018). More general comparison between our approach and related research in the literature is summarized in Table B7.

Table B7 summarizes recent literature (Kinahan et al., 2010; Doot et al., 2010; Taghanaki et al., 2018; Ford et al., 2006; Ziegler et al., 2015) dealing with disease burden estimation on PET/CT. Some methods have been tested on the NEMA phantoms. Methods based on deep learning techniques generally require a large number of training data sets.

Among all methods listed in Table B7, the one in (Taghanaki et al., 2018) comes close in spirit to our approach. There are several advantages of our approach over that in (Taghanaki et al., 2018). (i) We demonstrate the generality of AAR-DQ at object level and lesion level, with both manual and automatic recognition steps, while the referred work seems to operate only at lesion level. It is not clear in (Taghanaki et al., 2018) how the lesion-level ROIs are generated with the only information provided stating that ROIs were drawn around lesions by an expert on PET. We must also note that AAR-DQ is set up in a general manner so it can make use of existing object models and anatomy models constructed for other applications involving object segmentation, etc. The only additional component required, namely disease map, is easily encoded into the anatomy model. (ii) AAR-DQ requires much smaller number of training samples than (Taghanaki et al., 2018). (iii) The performance of our approach was comparable to (Taghanaki et al., 2018) on patient (lesion-level) data sets but better than that reported in (Taghanaki et al., 2018) on phantom data sets. (iv) Our disease map estimation (training) step takes ~2 minutes on a desktop computer with 4 Intel i7-core CPUs, 64 GRAM, and under Ubuntu 16.04 OS. Computational timing is not reported in (Taghanaki et al., 2018) and we suspect that its training step is lot more time-consuming.

TABLE 7

Comparison of the AAR-DQ approach with recent literature for disease burden estimation on PET/CT images considering TLG error, $SUV_{Mean}$ and $SUV_{Max}$.

| Methods | | Number of Training, testing samples, cross validation | Phantom and number | Error in disease burden estimation |
|---|---|---|---|---|
| Med. Phys., (Ford et al., 2006) | Threshold based segmentation for tumors on PET | — | NEMA, 20 $^{18}$F | $SUV_{Max}$ errors within 0.0%-60% for spheres from the largest to the smallest, no TLG error reported |
| Semin CT MR, (Kinahan, et al., 2010); Doot et al. Med. Phys. (Doot, et al., 2010) | Manually draw circles with diameter 10 mm at sphere centers for all spheres | — | NEMA, 20, $^{18}$F/Ge$^{68}$ | $SUV_{Max}$, $SUV_{Mean}$ errors within 0.0%-60% for spheres from largest diameter (37 mm) to the smallest (10 mm) |
| EJNMMI Phys, (Ziegler et al., 2015) | Manually draw circles (only for 4 spheres) around lesions on PET | — | NEMA, 20 $^{18}$F | $SUV_{Mean}$ error within 19.8%-63.2%, no TLG error reported |
| CMIG, (Taghanaki et al., 2018) | Multiple random forest machine learning approach to predict disease burden | 55 patients, each patient with one (conspicuous) tumor, LOO cross validation | NEMA, 20 $^{18}$F | For phantom, 13.03% for TLG error (no SD for TLG reported); activity ($SUV_{Mean}$) error 5.7 ± 5.25%, no $SUV_{Max}$ error reported. For patient, 13.83% ± 21.47% for $SUV_{Mean}$ error and 12.17% ± 5.34% for TLG error |
| Proposed approach | Disease-map-based approach for object/lesion level DQ | 40 conspicuous lesions, 10 non-conspicuous lesions, LOO cross validation | NEMA, 20 Ge$^{68}$ | For phantom, at object level DQ, TLG error 5.82% ± 1.86% with $SUV_{Mean}$ error <3%, $SUV_{Max}$ error close to zero; For patient, lesion level DQ, TLG error 9.1% ± 3.9% with $SUV_{Mean}$ error <7%, $SUV_{Max}$ error <1% |

AAR-DQ extends the previously-developed AAR technology (Udupa et al., 2014) to disease quantification by stopping at the object recognition step and performing disease quantification directly from object location information, permitting the methodology to skip the rather challenging and somewhat ill-defined step of explicit object delineation. Our long-term goal is to adapt AAR-DQ for body-wide automatic disease quantification on PET/CT images building on the generality of AAR in body-wide object recognition/delineation. AAR-DQ adopts a fuzzy strategy throughout—for object modeling, object recognition, disease mapping, and disease quantification. This allows handling of disease gradation without the need to perform explicit partial volume correction and committed binary classification. Three methods were presented for disease quantification, two at the object (e.g., organ) level—DQ-AO and DQ-MO, and one at the lesion level—DQ-ML. Commercially available clinical software was used to generate reference disease measurements at the lesion level with the assistance of a manually guided method of quantification as needed. By using these reference quantities, evaluations were carried out using both NEMA phantoms and clinical FDG-PET/CT image data sets in patients with metastatic cancer.

As described herein above, objects in a body region may be recognized/localized. Such localization may benefit from virtual landmark techniques, as will be described below.

Virtual Landmarks

Landmark-based techniques have been widely used in the computer vision and image processing fields, especially in medical image segmentation, registration, and shape analysis. Landmarks can be identified in purely manual or automatic ways. Some anatomic locations, such as the aortic root or the inferior aspect of the mandible, can be manually labeled as landmarks. However, labeling landmarks manually is tedious, and may lead to low repeatability, especially when labeling a point/voxel in 3D space on slices or on 3D surfaces. An automatic landmark-defining program can be devised based on machine learning techniques to initially set up landmarks, followed by another operation such as non-rigid registration to refine the correspondence between landmarks. These approaches are indirect and involve higher complexity derived from non-rigid registration. Much has been published on finding landmarks on object surfaces in the context of shape modeling. While this is still an open problem, many of the challenges of past approaches can be overcome by removing the restriction that landmarks must be on the object surface. The virtual landmarks we propose may reside inside, on the boundary of, or outside the object and are tethered to the object. Our goal for virtual landmarks is simply to describe accurately positions relative to the object. Our solution is straightforward, simple, and recursive in nature, proceeding from global features initially to local features in later levels to detect landmarks. Principal component analysis (PCA) is used as an engine to recursively subdivide the object. The method is illustrated in 3D space, but it generalizes readily to any K-dimensional space and can be utilized in any landmark-related applications of computer vision and pattern recognition.

In certain aspects, a novel PCA-based automatic landmark identification approach is described in which landmarks are not constrained to lie on object surfaces. Then, the approach is demonstrated to be able to work well on different subjects and different anatomic structures and on both binary and gray object representations. Finally, empirical demonstration is made to show the theoretical property that the landmarks detected are invariant to rigid transformations.

Image Data

Thoracic and abdominal CT images from 5 near normal subjects are utilized in our experiments. As in our previous studies, all CT images were selected from our health system patient image database following approval from the Institutional Review Board at the Hospital of the University of Pennsylvania along with a Health Insurance Portability and Accountability Act waiver. In this study, 4 objects including liver, trachea & bronchi (tb), the outer boundary of the left lung along the left pleura (lps), and the outer boundary of the right lung along the right pleura (rps) from diagnostic contrast-enhanced CT (with a voxel size of 0.72×0.72×5 mm$^3$) are utilized to illustrate virtual landmark properties. The whole-body skeleton from a low-dose unenhanced CT scan (with a voxel size of 1.17×1.17×4 mm$^3$) is also used to calculate virtual landmarks and to visualize them in the whole body.

Principal Component Analysis (PCA)

PCA is a commonly-used statistical pattern recognition procedure that employs an orthogonal transformation to convert a set of observations of possibly correlated random variables into a set of linearly uncorrelated random variables called principal components. Roughly speaking, the eigenvalues resulting from applying this analysis to the points in a 3D object region indicate the variance (dispersion) of the object points in the three directions represented by the corresponding eigenvectors. The largest eigenvector indicates the direction of elongation of the object, and the other two eigenvectors indicate roughly the directions of breadth and thickness of the object.

Iterative PCA Based Virtual Landmark Identification

Figure 17:
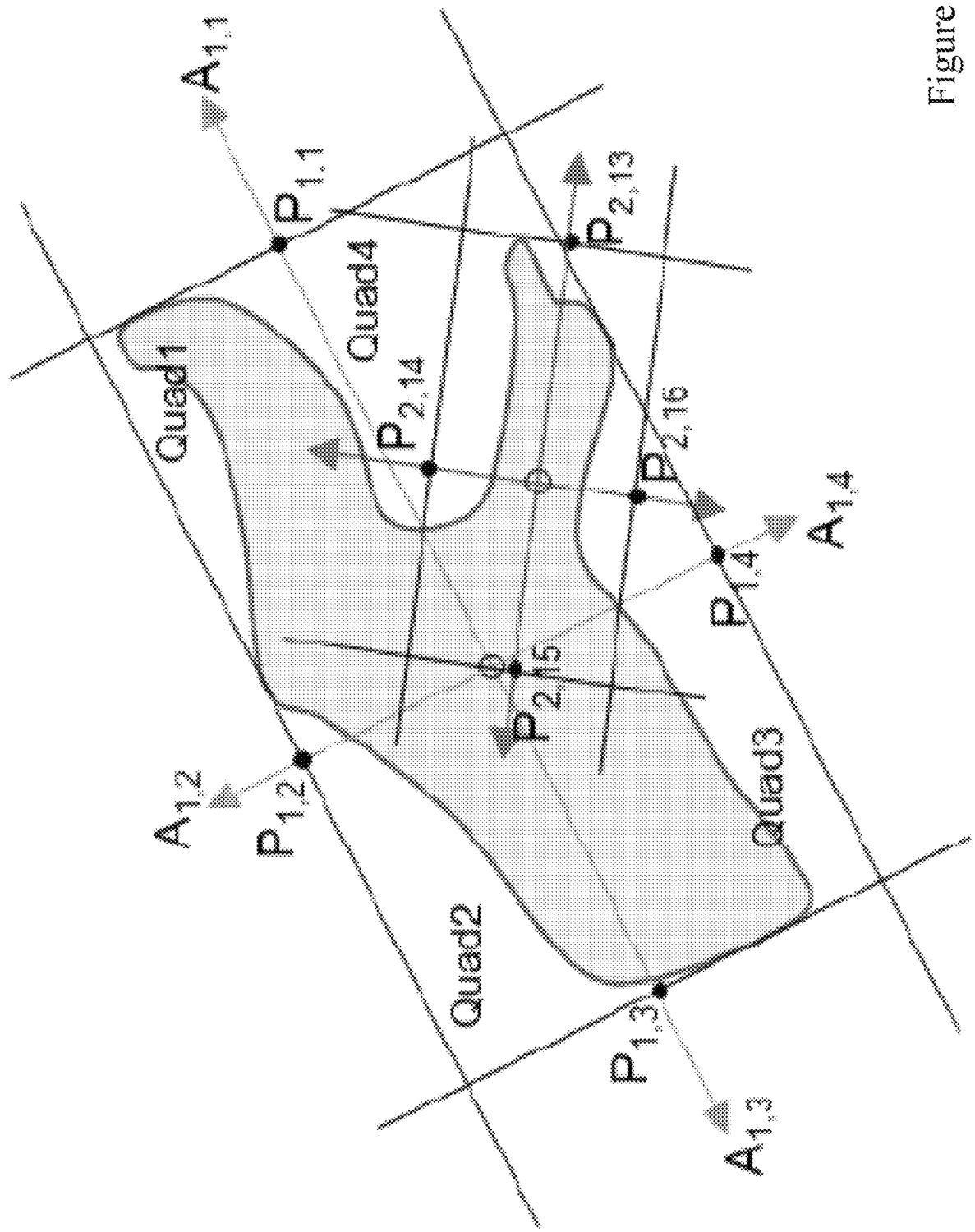
FIG. 17 illustrates virtual landmarks from iterative PCA on a 2D object.

The idea underlying the concept of virtual landmarks of an object is illustrated with a 2D example in FIG. 17. Given a binary image representing the object, PCA of the entire binary 2D object region is first carried out to find the four principal axes directions, denoted in the figure in green by $A_{1,1}, A_{1,2}, A_{1,3}, A_{1,4}$, emanating from the geometric centroid of the object. Along these axes, we find points $P_{1,1}, P_{1,2}, P_{1,3}$, and $P_{1,4}$ that indicate the extent of the object in those directions. These four points together with the geometric center form the first level landmarks (first subscript denotes level). These points and the axes subdivide the shape into four pieces in the four (not necessarily equal) quadrants. For each piece, we perform PCA again and find the 16 second level landmarks denoted $P_{2,1}, P_{2,2}, \ldots, P_{2,16}$ and the 4 geometric centers. The four points $P_{2,13}, P_{2,14}, P_{2,15}$, and $P_{2,16}$ obtained for the 4th quadrant and the corresponding geometric center are shown in the figure for illustration ($2^{nd}$ level principal axes are shown in red). The process continues up to a specified level. Note that the points are ordered and hence have unique labels. This allows us to specify the landmarks we need by their labels for representing a given shape. For our example, we may use just the 7 points $P_{1,1}$, P1,2, P1,3, P1,4, $P_{2,13}, P_{2,14}$, and P2,16 (which already denote the shape roughly). Different objects may be codified by different numbers of points. Note how the points tend to move closer to the object surface at higher levels. In the 3D case, at level n, we will have $8^{n-1}$ octants and there will be in total $7\Sigma_{x=1}^{n}8^{x-1}$ points for n levels. The total number of virtual landmarks for 1, 2, and 3 levels are 7, 63, and 511, respectively. Landmarks at early levels capture overall form whereas points at later levels provide more subtle details of form. Note that the above expression gives the maximum number of virtual landmarks for a given number of levels. In a given shape, empty octants at any given level and beyond will not contribute any landmarks.

Unlike methods of finding landmarks on boundaries, this approach generalizes to spaces of any finite dimension easily. For K-dimensional space, the maximum total number of points for n levels will be $(2K+1)\Sigma_{x=1}^{n}2^{K(x-1)}$. From the definition and the iterative PCA procedure, it is easy to demonstrate that the derived landmarks are invariant to translation, rotation, and (uniform) scaling of the binary object. The method also readily generalizes to non-binary objects—fuzzy objects and objects with gray values defined for their voxels—by considering the "weight" of the individual voxels within the object in performing PCA.

Virtual Landmarks of Different Objects

Figure 18:
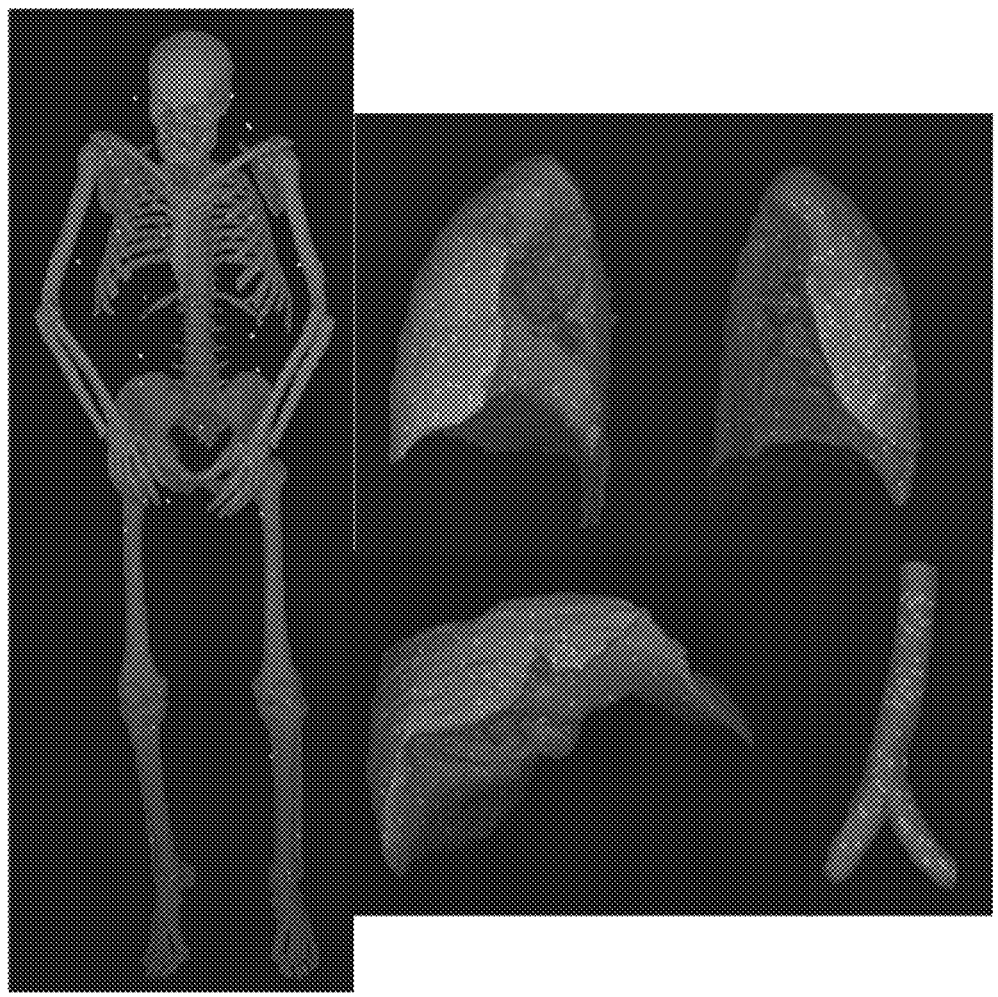
FIG. 18 illustrates virtual landmarks of skeleton, rps, lps, liver, and tb derived from image data from one subject.

FIG. 18 shows the virtual landmarks derived for different objects: whole-body skeleton, rps, lps, liver, and tb, where landmarks in 3D space are overlaid on to those objects' 3D surface renditions. In all examples shown, landmarks up to the third level and only those landmarks representing the geometric centers are demonstrated. The virtual landmarks seem to be distributed through whole objects more-or-less uniformly, meaning that they are not concentrated all in one portion of the object. Note also how the landmarks may lie anywhere in space.

Many landmarks may not be on the surface of objects, especially for the skeleton. In fact, it is rare to find a landmark precisely on the object's surface. Placement exactly on the surface can happen only when an eigenvector intersects the surface precisely at a point which is also the tangent point to a plane drawn orthogonal to the eigenvector. The landmarks, even when outside or inside the object, still have a strong connection with the target structure. That is why they are named virtual landmarks. From FIG. 18 we can see that the concept of virtual landmarks seems to apply equally well to different objects. Interestingly, some points at the junction of the bronchi are also selected by the approach as virtual landmarks.

Virtual Landmarks from Different Subjects

Figure 19:
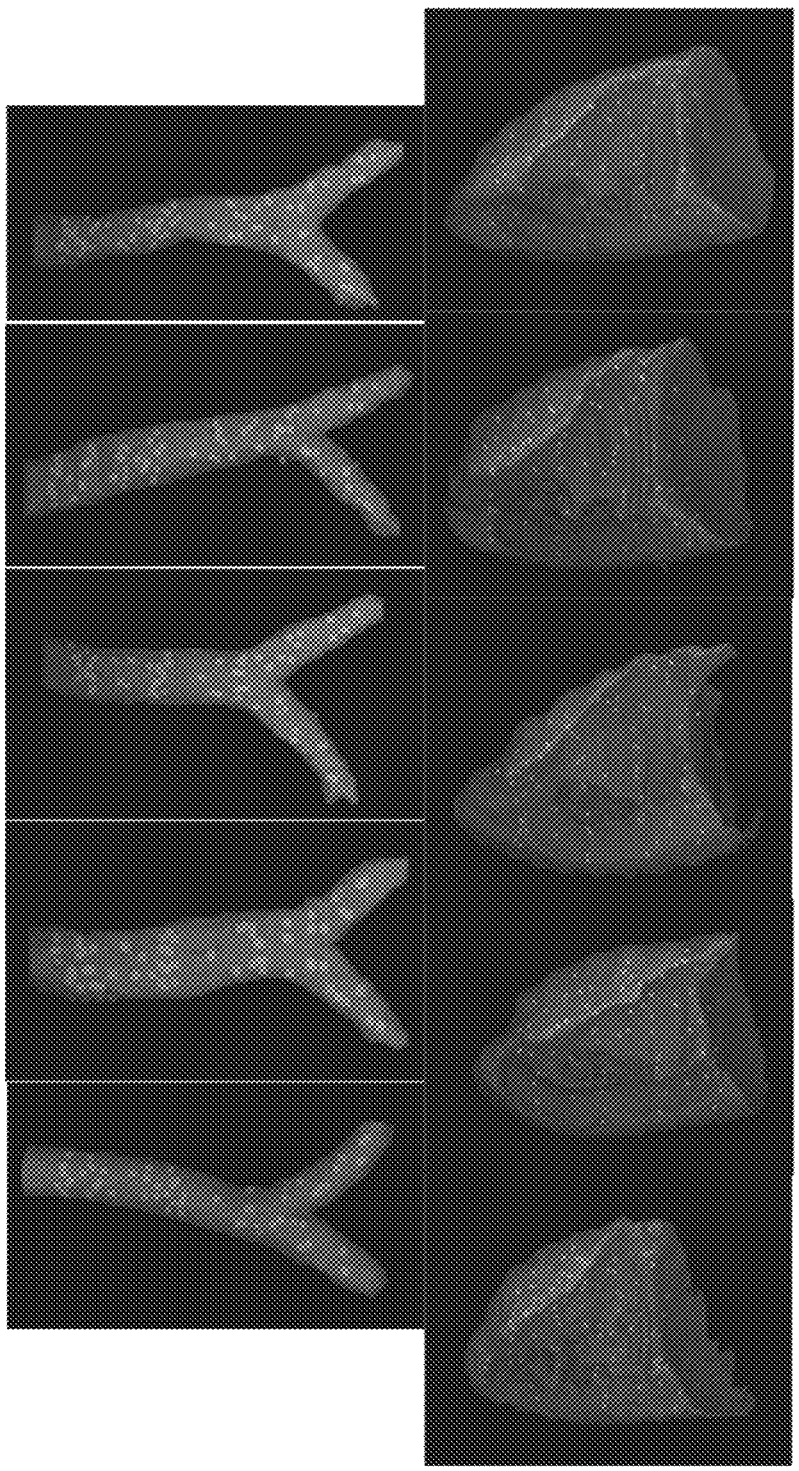
FIG. 19 illustrates virtual landmarks of tb and lps in five patients.

FIG. 19 shows the virtual landmarks of tb and lps, each set derived from 5 subjects. Observe that the virtual landmarks from these different subjects follow a similar pattern, which preliminarily demonstrates that the landmarks are detected at homologous locations in different samples of the same object from different subjects. This will form the fundamental basis for applications based on virtual landmarks, such as building object models or locating objects automatically on images, etc. In other words, virtual landmarks seem to be able to encapsulate the intrinsic shape properties of objects.

Virtual Landmarks After Translation, Scaling, and Rotation

Five thoracic CT images as well as their binary masks were translated (10 mm in x and y direction), scaled in x, y and z direction by a factor of 1.2, and rotated by 90 degrees with respect to the original image for all four objects. The virtual landmarks were computed and the Euclidian distance among virtual landmarks before and after the transformation was computed (Table C1). The average distance (error) is a fraction of the pixel size (which is 0.72 mm), stemming mostly from interpolation errors. This empirically demonstrates that the virtual landmarks are invariant to rigid transformations of the image/objects. This, we believe, is a useful theoretical property of the approach in landmark-based applications.

TABLE C1

Mean (sd) distance (in mm) between virtual landmarks from objects before and after rigid transformation.

| Translation | Scaling | Rotation |
| --- | --- | --- |
| 0.22 (0) | 0.24 (0.22) | 0.61 (0.15) |

Virtual Landmarks on Binary Versus Gray Images

As mentioned earlier, virtual landmarks can be derived from the object binary mask or from the corresponding intensity image. The landmarks derived from these two methods may differ depending on the pattern of intensity distribution within the object. Table C2 shows the Euclidian distance (the average and standard deviation) between corresponding landmarks derived from those two methods for different objects.

TABLE C2

Mean (sd) of distances (in mm) between virtual landmarks derived from binary and gray images for liver, tb, lps, and rps.

| Liver | tb | lps | rps |
| --- | --- | --- | --- |
| 0.29 (0.21) | 7.18 (3.94) | 18.61 (10.19) | 21.85 (15.28) |

Figure 20:
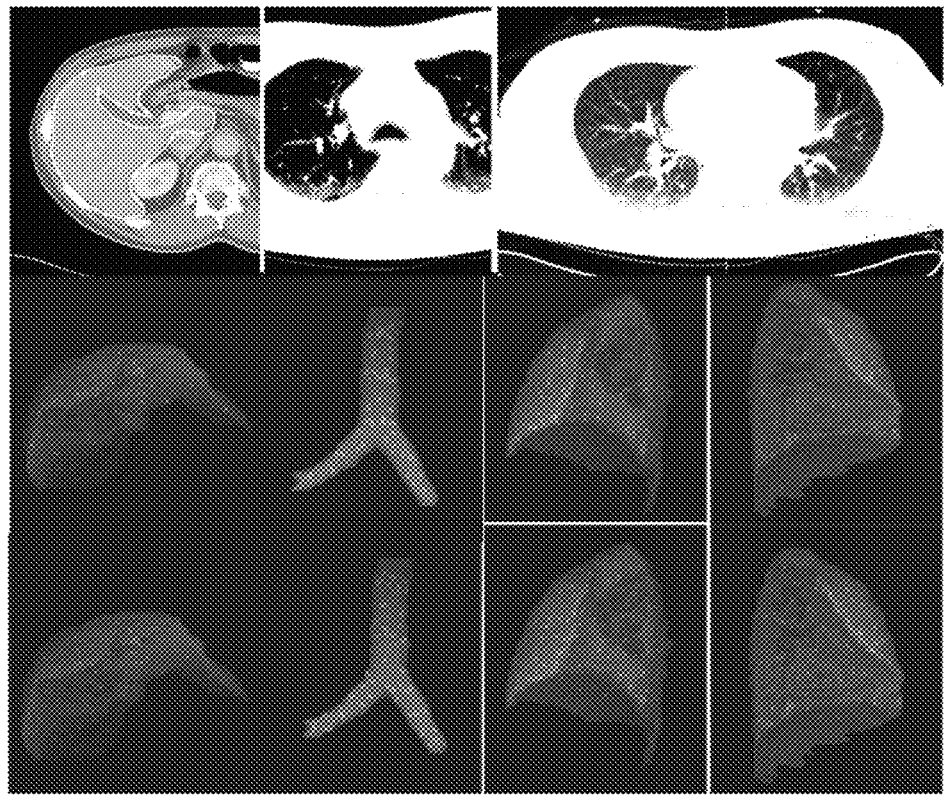
FIG. 20 illustrates binary masks (in color) for liver, tb, rps, and lps on the top row, where virtual landmarks from the binary images are at the middle row, and virtual landmarks from gray images are at the bottom row.
Figure 21:
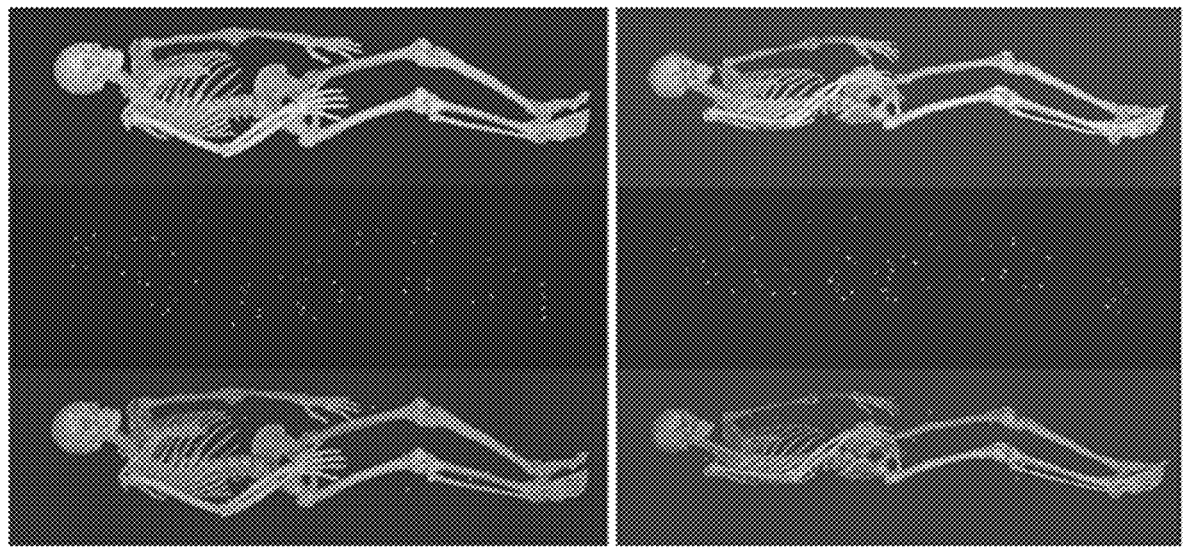
FIG. 21 illustrates 3D renditions of the skeleton representing one reference object derived from two patient data sets along with the derived virtual landmarks shown in different forms: the object by itself, only the landmarks, and the two together.
Figure 22:
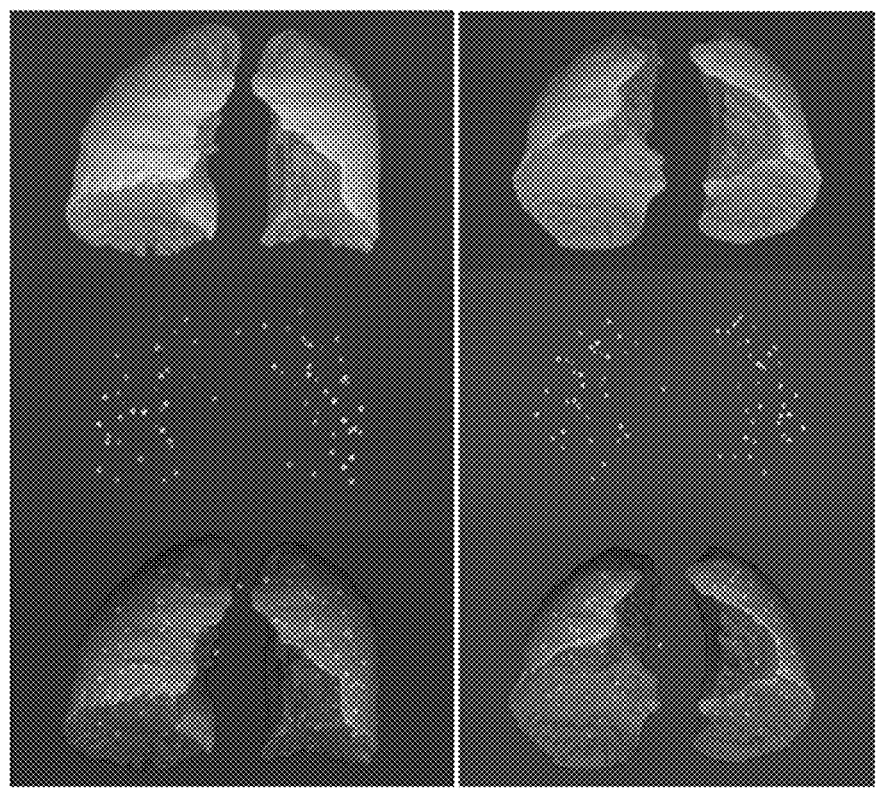
FIG. 22 illustrates 3D renditions of the pleural space representing one reference object derived from two patient data sets along with the derived virtual landmarks shown in different forms: the object by itself, only the landmarks, and the two together.

Considering the fact that slice separation is 5 mm in these data sets, the average distance for landmarks of liver and tb is around 1 voxel, implying that the virtual landmarks of liver and tb derived from binary and gray images are almost the same. However, these distances for lps and rps are larger. The reason is the larger degree of non-uniformity of image intensities inside these objects. FIG. 20 shows the binary masks of liver, tb, lps, and rps overlaid on gray image slices for one subject. The intensity inside the liver mask is more uniform than the intensities of lps and rps. Virtual landmarks for liver from binary image and gray image are much similar to each other comparing with other three objects, tb, rps, and lps. In general, virtual landmarks generated by the two methods can be quite different, especially at higher levels of subdivision.

The present disclosure introduces a novel PCA-based automatic landmark identification approach which automatically resolves the issue of establishing homology among landmarks from different object samples. Previous approaches to landmark identification consisted of two disparate steps of first detecting landmarks and then finding homology. In the virtual landmark approach, the concept of homology is built into the definition of the landmarks. The method removes the restriction of past approaches which require the landmarks to be situated on the object surface and allows them to be anywhere with respect to the object, although they remain tethered to the object by its shape and/or intensity distribution. The approach guarantees that virtual landmarks are invariant to rigid transformations. The virtual landmarks seem to be tagged at homologous locations in the same object derived from different subject image data sets.

One application of virtual landmarks is to automatically localize anatomic body regions with the idea that the geometric relationship between these landmarks of reference objects and the boundary locations of body regions can be learned through a neural network regressor, and then the locations can be predicted. More details are discussed herein below.

Automatic Thoracic Body Region Localization

Radiological imaging and image interpretation and the utilization of images for clinical decision making are mostly specific to each body region such as head, neck, thorax, abdomen, pelvis, and extremities. Although imaging is often performed body-region-wise, the acquired images do not usually conform to any standardized definition of body regions. For automating image analysis and consistency of results, standardizing definitions of body regions and the various anatomic objects, tissue regions, and zones in them becomes essential. Even when imaging is performed body-wide, like in whole-body PET/CT images, it becomes necessary to perform analysis body-region-wise in numerous applications, particularly those involving systemic diseases, for disease staging, treatment planning, response assessment, and restaging. Although methods have been reported in the literature for automatically locating regions of interest based on physical anatomic landmarks observable on images, the regions of interest considered have been mainly whole organs. The present disclosure presents a solution to the problem of automatically defining entire body regions, employing not physical landmarks but conceptual or virtual landmarks that may not correspond to any physically observable anatomic feature on the image.

Assuming that a standardized definition of body regions is available, one of the fundamental early steps needed in automated image analysis, image analytics, and object analytics is to automatically trim the given tomographic image stack of a body region into an image volume exactly satisfying the body region definition. If a whole-body tomographic image stack is given, the task is to precisely divide the stack into body regions as per the exact definition of each body region. Although many approaches to automatic identification of objects, landmarks, and specific anatomic features are available in the literature, this important and fundamental problem does not seem to have been addressed. The present disclosure presents a solution to this problem and evaluates it on whole-body or near whole-body PET/CT images. The main contributions of this work can be summarized as follows: (1) An automated whole-body region localization method. (2) The idea of a virtual landmark can take into account both object shape and intensity appearance. (3) The method can be generalized to other imaging modalities and reference objects easily.

For initial demonstration, we will focus on one body region, namely the thorax, and follow its definition formulated in Udupa J K, Odhner D, Liming Z, et al. "Body-wide hierarchical fuzzy modeling, recognition, and delineation of anatomy in medical images". Medical Image Analysis, 18(5),752-771(2014) and Wang H, Udupa J K, Odhner D, et al. "Automatic anatomy recognition in whole-body PET/CT images". Medical Physics,43(1),613-629(2016).

We define the thoracic body region as extending 5 mm superior to the lung apices to 15 mm inferior to the lung bases. In any given image, I, we will denote the location of the superior axial slice of the thorax by TS(I) and the location of the inferior axial slice of the thorax by TI(I). Locations in all images are specified with reference to some fixed coordinate system, such as the scanner coordinate system. Our problem is: Given any image I, find automatically locations TS(I) and TI(I) in I. We assume that the slices of I are organized axially and that the body region it encompasses properly includes the body regions to be identified in I. In certain aspects, we deal with whole-body or near whole-body PET/CT imagery, and so, this condition is always met. If this is not the case, the location predicted by our method will extend beyond the body region covered by I, but will be in correct relationship with that data set and the subject in the scanner coordinate system.

The proposed method for body-region localization works overall as follows. It uses one or more objects that can be easily segmented in I as reference objects and finds in them virtual landmarks. It then trains a neural network to learn the relationship between these landmarks and the known true locations for TS(I) and TI(I) which are obtained from a training set of images. Subsequently, the trained network is used to predict the body region boundary locations in any given image. These found locations are then used to subdivide the given image into body regions. These steps are further described below.

Image Data:

We selected whole-body CT image datasets from existing PET/CT scans of subjects from our health system patient image database following approval from the Institutional Review Board at the Hospital of the University of Pennsylvania along with a Health Insurance Portability and Accountability Act waiver. The subjects whose image data are selected included near-normal cases and patients with different types of disease conditions. Among these, 34 were whole-body scans (head to foot) and 180 were near whole-body (neck to foot). They all included fully the body region of interest, namely the thorax. In this study, we used only the low-dose unenhanced CT portion of the PET/CT data sets. However, our approach is applicable to just PET alone and both CT and PET used simultaneously. The voxel size in the CT data sets is roughly spread from 1 mm×1 mm×3 to 1 mm×1 mm×5 mm for CT-scans of different subjects.

Reference Objects:

We selected the left and right pleural spaces together as one reference object and the skeletal structure of the entire body as another object of reference. Segmentation of the objects was performed using the algorithms implemented in the CAVASS software system. The segmentation results are stored as binary images. The requirements for a reference object are: it should be fully contained within the data set, it should be easily segmented automatically, and it should not be clustered within some small space in the body. Thus, for the skeleton reference object, only 34 data sets were available, since the other data sets do not satisfy the first condition. However, for the pleural spaces reference object, all 180 data sets were utilized.

Extraction of Virtual Landmarks:

Virtual landmarks associated with an anatomic object are reference points which are tethered to the object. The points may lie anywhere within the body with respect to the object—inside, outside, or on its boundary, and most likely they do not lie exactly on the boundary. They can be defined on the binary image representing the object or using both object shape and gray value appearance from an underlying image at voxels that belong to the object. The landmarks are obtained through a process of recursive subdivision of the object guided by principal component analysis (PCA). At the highest level, the geometric center of the object is the only landmark produced. The eigenvectors associated with the object define a principal axis system and divide the object into 8 octants. The part of the object in each of these octants is again subjected to PCA which yields a geometric center and a principal axis system. At the second level, thus, 8 landmarks are generated. In the third level, continuing this process of subdivision, 64 landmarks are generated, and so on. The method guarantees correspondence among homologous points in different samples of the object from different subjects automatically, as is clear from the process of generating the points. It is also clear that the method allows selecting any desired virtual landmarks and any number of them since each landmark has a unique identifier associated with it in the process of subdivision. In certain aspects, we used different numbers of landmarks as described below. The total number of virtual landmarks generated in n levels for a 3D object is $\Sigma_{i=1}^{i=n} 2^{3(i-1)}$. For n=2, 3, and 4 levels, the number of virtual landmarks generated is 9, 73, and 585, respectively.

Labeling True Locations of Body Region Boundaries:

The actual locations in the cranio-caudal direction of the boundaries of the body region, or the values of TS(I) and TI(I), for all images in our data sets, are obtained by a visual examination of each data set, identifying the slices that define the boundaries of each body region, and recording the physical location of the slices in the scanner coordinate system using the CAVASS software. Note that there is potential subjective variation in this specification by readers which is due to how the body region boundary definition is interpreted by each reader on a specific image. Typically, this variation is within one slice.

Learning the Relationship Between Virtual Landmarks and True Locations of Body-Region Boundaries:

A neural network is configured as a regressor by feeding virtual landmarks and true locations as input and target output data sets, respectively, and the relationship is learned through network training, validation, and testing procedures. Here, we adopt a simple architecture of a multiple-layer perception with one hidden layer. The number of neurons in the input layer is the same as the dimension of virtual landmarks, and the number of neurons in the output layer is the same as the size of target locations vector. In addition, the numbers of neurons in the hidden layers are determined by the complexities of the nonlinear mapping function that is being approximated. The details of the neural network configuring and training will be presented in the next section. Then, the trained network is used to predict locations TS(I) and TI(I) for any test image I. Since true locations have been recorded for all data sets, we can evaluate the prediction error by comparing the predicted with the true locations.

Experiments and Results

Figure 15:
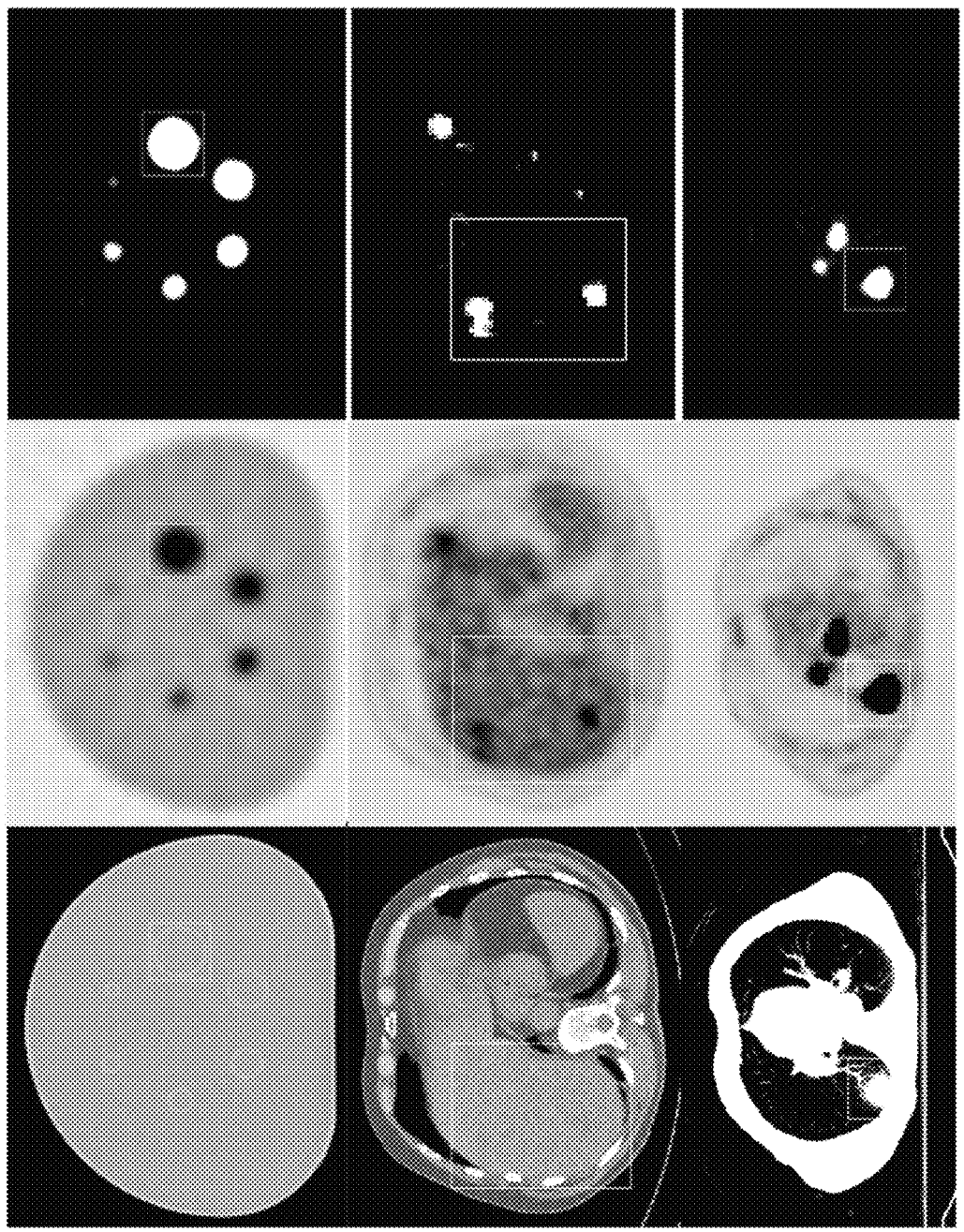
FIG. 15 illustrates Phantom ($1^{st}$ row), liver lesion ($2^{nd}$ row), and lung lesion ($3^{rd}$ row) examples. CT image slice with a box (left), PET image slice with the same box (middle), and the derived disease map (right). In this example, the liver contains two lesions and the right lung contains one lesion.
Figure 16:
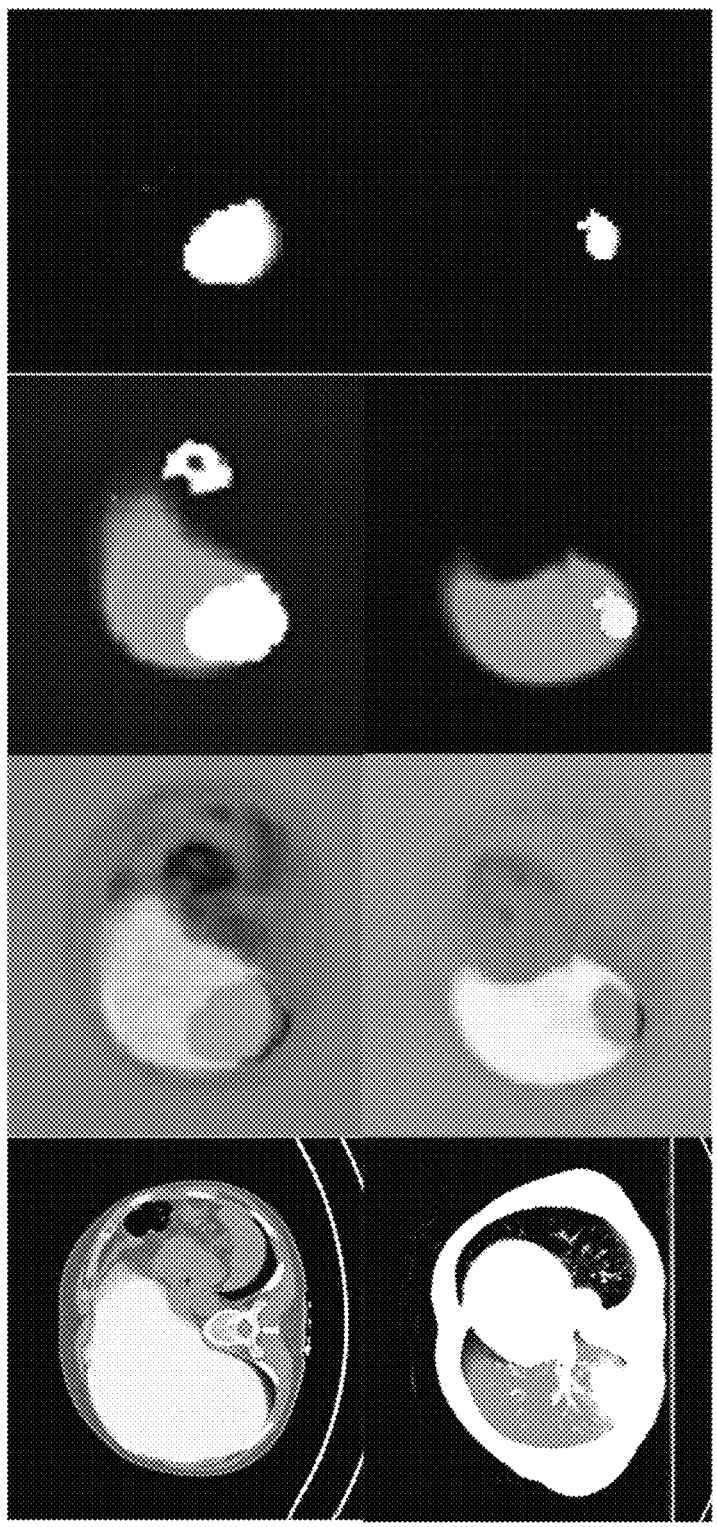
FIG. 16 illustrates AAR-DQ on liver (top row) and lung (bottom row). Left column is the recognition results (in yellow) of liver and lung on the CT images, and the second column is the recognition results from CT being propagated to PET image. Third column is the recognition results being overlaid onto the disease map of the whole image, and last column shows the final disease map.

To demonstrate the geometric relationship between the reference object and its virtual landmarks, in FIGS. 14 and 15 we display the 3D surfaces of the skeleton and the pleural space derived from whole-body PET/CT datasets of two patients along with the set of 73 virtual landmarks derived for this object from three levels (n=3). Notice that the 73 virtual landmarks spread quite uniformly in and around the object. It should be noted that some landmarks fall outside the object in the case of the skeleton reference object.

The landmark data with dimension as N×D×S are set as input data to the neural network, where N represents the number of landmarks, D represents 3D spatial coordinates (x, y, z) of the landmark points, and S represents number of subjects. Thus, if all data were to be utilized, the dimensionality of input data will be 73×3×34 for the skeleton reference object and 73×3×180 for pleural spaces reference object. The dimensionality of the target output data is L×S, where L represents the number of body-region boundary locations, in our case L=2 (it corresponds to TS and TI).

Here, we design the dimensionality of input data in terms of the coordinates of a subset of the virtual landmarks generated for a given number of levels (we chose L=3). For the skeleton reference object, due to the small number of data sets available, we used fewer landmarks instead of all possible landmarks generated for 3 levels. For example, to form a subset of 9 landmark points, we select 1 point from the first level and all 8 points from the second level. For a subset which contains 25 points, we select 1 point from the first level, all 8 points from the second level, and 16 points from the third level by choosing 16 designated octants out of the total 64 octants. In addition to varying L, we also tested a strategy, where, instead of using the (x,y,z) coordinates of points, only the z coordinate is considered for determining the input variables.

After configuring the input data and target data of the neural network regressor, three things such as the data dividing, the network architecture, and the training algorithm should be considered carefully. For both cases of using skeleton as reference object and using pleural spaces as reference object, we choose the Bayesian Regularization algorithm (BR) to implement the training process because it can prevent overfitting and provide better performance than the Levenberg-Marquardt algorithm. As the BR training algorithm is used, the validation set can be merged with the training set. So, we only need to divide the number of subjects (S) into two sets, i.e., training set and testing set. Here, we adopt the default setting of the toolbox which means that the training set makes up approximately 85% of the full data set, and the testing set makes up 15% of the full data set. That is, the ratio of the training set and the testing set are 29/5 and 153/27 for the two cases. A multilayer perception with a single hidden layer is chosen to be the neural network architecture, and different neuron numbers of hidden layers are selected in terms of empirical tests (which are listed in Table D1 for different coordinates of landmarks and dimension of input data) for the two cases. The performance index is mean square error (MSE).

Table D1 presents the localization error for TS and TI in units of Number of Slices (NoS) and millimeters (mm). The mean localization error in NoS for TS and TI is 3 and 2, respectively, when the skeleton is used as a reference object, and 3 and 5, respectively, when the pleural spaces are used as a reference object. The corresponding location errors in mm are 13 and 10, respectively, for skeleton and 10.5 and 20, respectively, for pleural spaces. Note that the total number of slices in a whole-body PET/CT scan is roughly 400 to 500 slices. A localization error of less than 3 in NoS is almost perfect keeping in mind the applications for which body region identification is automated and also considering the fact that the variation in human identification of the region boundary locations can be 1-2 slices. A location error of less than 5 NoS seems acceptable. It is noted that the localization error for thorax presented herein are more attractive when comparing to the more recent report[13] in reference with body region localization error of 47.01 mm.

[13] S. Hussein, A. Green, A. Watane, D. Reiter, X. J. Chen, G. Z. Papadakis, B. Wood, A. Cypess, M. Osman, U. Bagci, "Automatic Segmentation and Quantification of White and Brown Adipose Tissues from PET/CT Scans," IEEE Trans Med. Imaging, 36:734-744(2017).

TABLE D1

Localization error for TS and TI using skeleton and pleural spaces as reference objects.

| Reference object | Coordinates of landmarks | Dimensionality of input data | Neuron number of hidden layers | Localization error (NoS, mm) TS | TI |
|---|---|---|---|---|---|
| Skeleton | (x, y, z) | 25 × 3 × S | 3 | 3, 12 | 1, 12 |
|  |  | 9 × 3 × S | 2 | 3, 12 | 3, 12 |
|  | z | 25 × S | 1 | 4, 16 | 2, 8 |
|  |  | 9 × S | 2 | 3, 12 | 2, 8 |

TABLE D1-continued

Localization error for TS and TI using skeleton and pleural spaces as reference objects.

| Reference object | Coordinates of landmarks | Dimensionality of input data | Neuron number of hidden layers | Localization error (NoS, mm) TS | TI |
|---|---|---|---|---|---|
| Pleural spaces | (x, y, z) | 73 × 3 × S | 10 | 4, 15.3 | 9, 34.4 |
| | | 25 × 3 × S | 10 | 2, 7.6 | 5, 19.1 |
| | z | 73 × S | 3 | 3, 11.5 | 4, 15.3 |
| | | 25 × S | 8 | 2, 7.6 | 3, 11.5 |

From Table D1, we can learn several interesting aspects of the present method. Firstly, different localization accuracy can be obtained by employing different reference objects. The localizing performance by using the skeleton as a reference object is better than that by using the pleural spaces. This may be due to the higher complexity of the shape of the skeleton and its body-wide spatial extent, which may yield more powerful virtual landmarks. Second, the localization accuracy using only z coordinates seems better than that of using (x,y,z) coordinates, particularly for TI when using pleural spaces as the reference object. Third, a larger number of virtual landmarks does not necessarily imply higher accuracy in localization. Thus, finding landmarks which have higher information content may be important.

Figure 23:
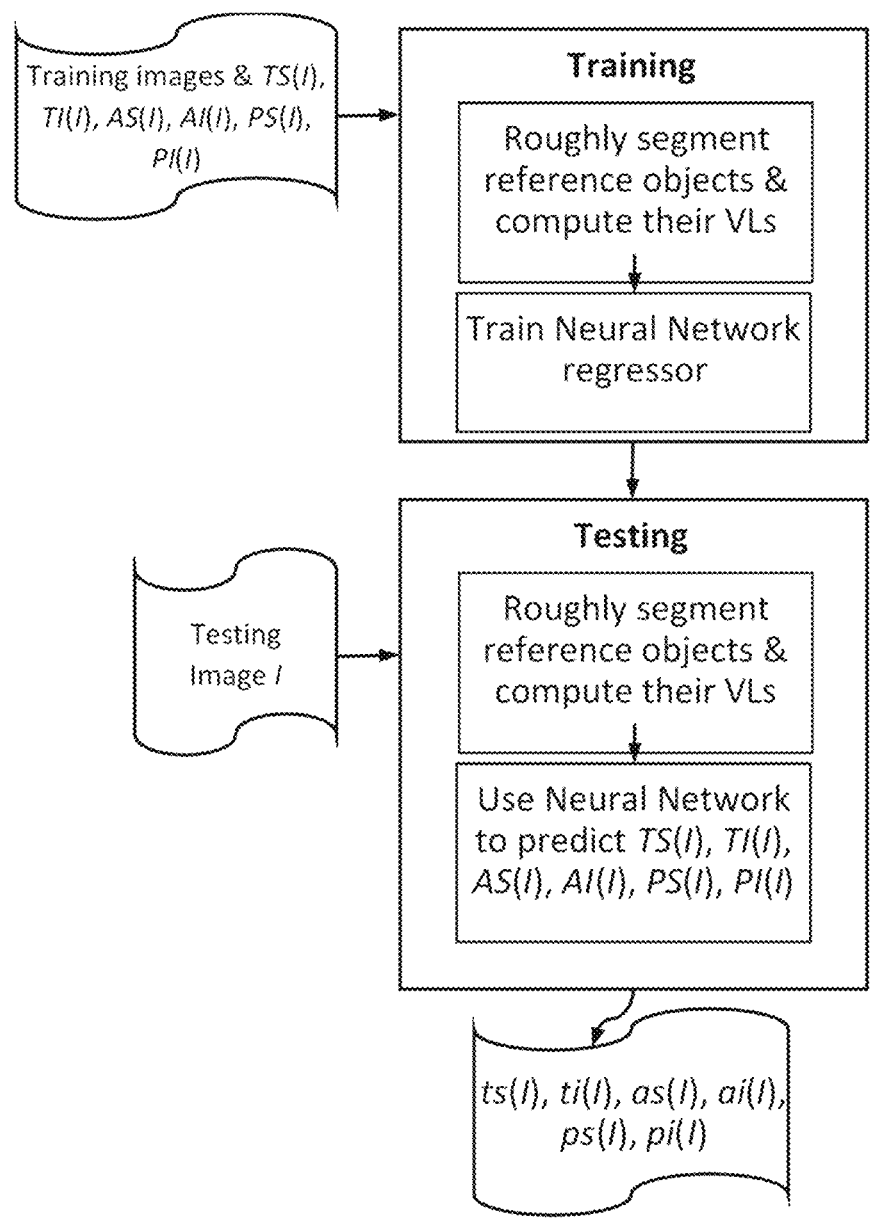
FIG. 23 illustrates an example schematic of a method for predicting boundaries.

Further detail and discussion of the above materials and methods are presented below. FIG. 23 shows a schematic of at least a portion of the process. One approach to the problem of parcellation of body into body regions on whole-body low-dose CT images of PET/CT acquisitions comprises two stages—a training stage and a testing stage—each further consisting of two steps. See FIG. 23 for a schematic illustration. We assume that a fixed definition of each body region of focus in this paper—Thorax, Abdomen, and Pelvis—is available in the form of their superior and inferior anatomic axial boundaries in the cranio-caudal direction, and denote these axial locations on an image I by TS(I), TI(I), AS(I), AI(I), PS(I), and PI(I), respectively. We then determine a set of easily (roughly) identifiable reference objects such as lung space and skeletal structures in the CT image of the CT data set. In the training stage, first a set of Virtual Landmarks (VLs) is computed for the reference objects in each training data set. Roughly speaking, VLs are points in the anatomic space that are tethered to the reference objects and may lie anywhere with respect to the objects—inside, outside, or on the boundary. Just the binary images constituting the reference objects or the binary images together with the gray values may also be used to determine the VLs. Then, a neural network is trained to regress the relationship between the VLs and the known true locations of TS(I), TI(I), AS(I), AI(I), PS(I), and PI(I) over all training images I. In the testing stage, given a PET/CT data set, first the reference objects are roughly identified on the CT image and their VLs are computed. Subsequently, the trained neural network is employed to predict the locations of the 6 body region boundaries in the CT image. We evaluate our approach utilizing 180 PET/CT data sets.

Data Sets and Notations

In one aspect, we use F-fluorodeoxyglucose (FDG)-PET/CT scans from 180 patients already existing in our health system patient image database. We obtained approval for data usage from the Institutional Review Board at the Hospital of the University of Pennsylvania along with a Health Insurance Portability and Accountability Act waiver. Subjects include near-normal cases and patients with different types of disease conditions where all scans were administered for clinical reasons only. Of these 180 scans, 34 were scans covering the entire body from head to feet (typically comprising of 465 axial slices) and the remaining 146 were near-whole-body scans extending from neck to feet (each comprising of close to 300 axial slices). At present, we use only the low-dose CT portion of these data sets (see Discussion for further comments). The voxel size in these CT data sets is roughly $1 \times 1 \times 4$ mm$^3$; the slice spacing varied from 3 to 5 mm: 139 studies with 4 mm, 37 with 3 mm, and 4 with 5 mm, their weighted average being 3.8 mm. It is important to keep in mind this clinical slice spacing (~4 mm) in understanding the accuracy of our results.

We will use the following notations throughout. I: Our collection of CT image data sets. $I_T$: The subset of I used for training our methods. $I_t$: The subset of I used for testing our approach. I: a given image data set of a patient. TS(I), TI(I), AS(I), AI(I), PS(I), PI(I): Known true superior and inferior boundary locations of the thorax, abdomen, and pelvis, respectively, in image I. ts(I), ti(I), as(I), ai(I), ps(I), and pi(I): Superior and inferior boundary locations of the thorax, abdomen, and pelvis, respectively, in image I predicted by our approach.

Definition of Body Regions

TABLE E1

Definition of body regions and their boundary locations.

| Body region | Boundaries | Description | Definition |
|---|---|---|---|
| Thorax | TS | Thoracic superior axial boundary location. | 15 mm above the apex of the lungs. |
| | TI | Thoracic inferior axial boundary location. | 5 mm below the base of the lungs. |
| Abdomen | AS | Abdominal superior axial boundary location. | Superior-most aspect of the liver. |
| | AI | Abdominal inferior axial boundary location. | Point of bifurcation of the abdominal aorta into common iliac arteries. |

TABLE E1-continued

Definition of body regions and their boundary locations.

| Body region | Boundaries | Description | Definition |
|---|---|---|---|
| Pelvis | PS | Pelvic superior axial boundary location. | Inferior boundary of the abdominal region. |
|  | PI | Pelvic inferior axial boundary location. | Inferior-most aspect of the ischial tuberosities of the pelvis. |

In medical practice, the human body is divided into several regions in the cranio-caudal direction: head, neck, upper extremities, thorax, abdomen, pelvis, and lower extremities. In one aspect, we focus on three body regions—thorax, abdomen, and pelvis. Table E1 summarizes the definitions. We define a body region by two axial slices: one denotes the superior axial limit or boundary and the other denotes the inferior axial boundary. Given a scan or image I, we denote the location of the superior axial slice of the thorax in I by TS(I) and the location of its inferior axial slice by TI(I) as defined in Table E1. Similarly, we denote the superior and inferior axial locations of the abdominal and pelvic regions by AS(I), AI(I), PS(I), and PI(I), respectively, per Table E1. Locations in all images are specified with reference to a fixed scanner coordinate system.

Figure 24:
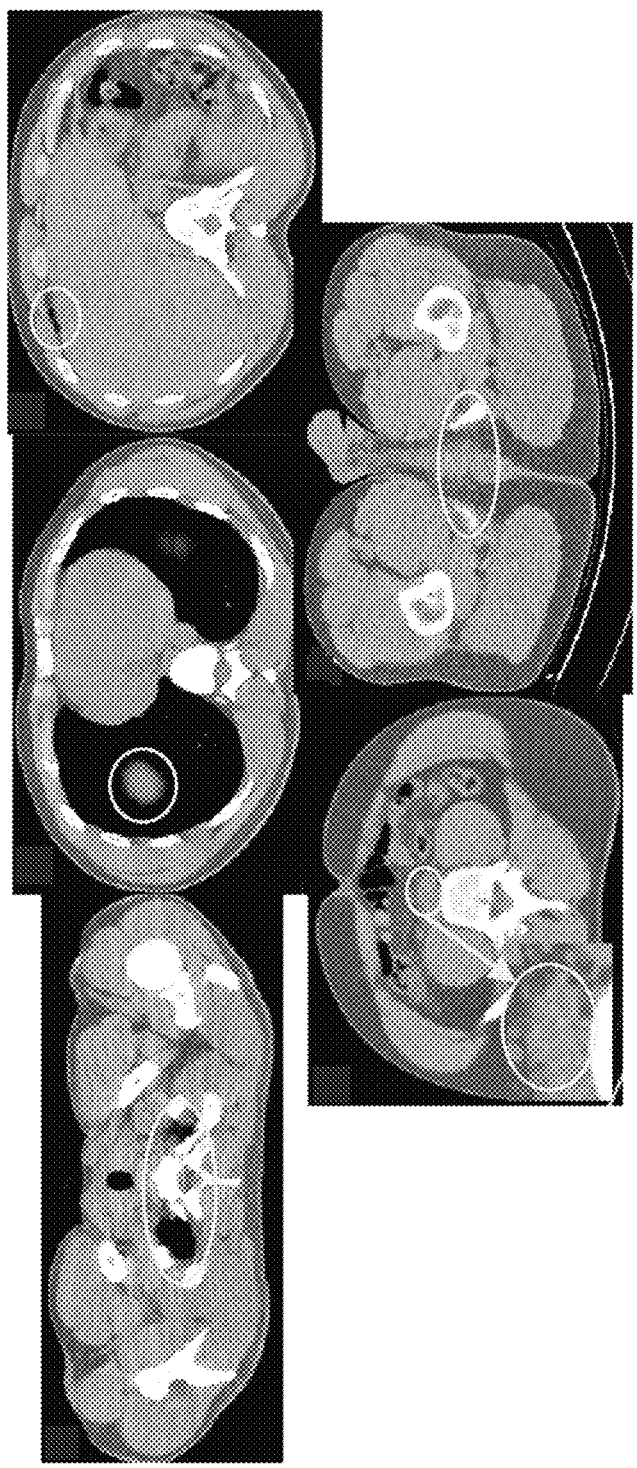
FIG. 24 illustrates an example features for determining boundaries.

Note that, per our definition, AI(I)=PS(I). Note also how the abdominal and thoracic regions overlap. This is inevitable since the boundaries are defined through axial planes, and some of the axial planes passing through the thorax contain abdominal tissue regions. In FIG. 24, we show a close-up pictorial view of the definitions by displaying slices containing the features (encircled in the figure) that are used to determine true slice boundaries. Note how the distinguishing feature for AI is very subtle. Of course, our method does not look for these features but is based only on the relationship between VLs and the true boundary slice locations.

Figure 25:
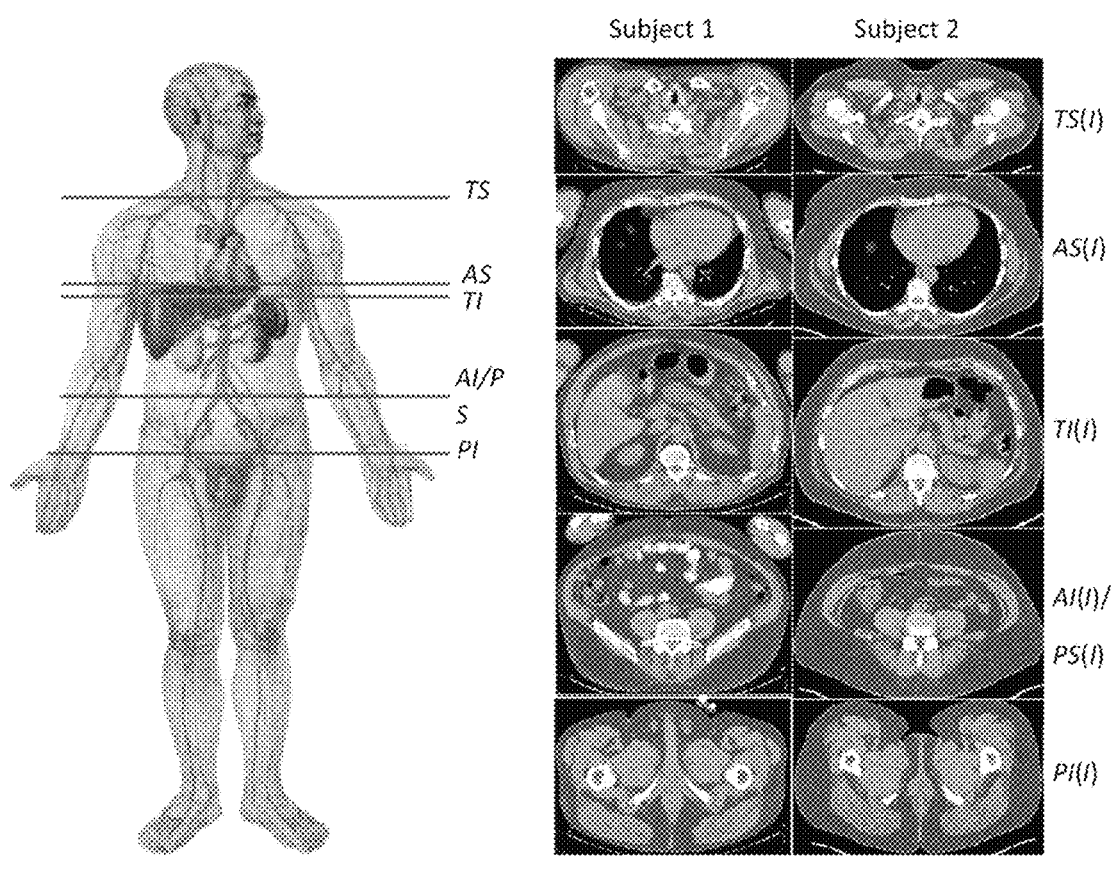
FIG. 25 illustrates example boundary locations.

In FIG. 25, we display exemplar boundary slices from two subjects. There exist substantial differences in the appearance of slices at the same boundary location among different subjects. Depending on the thickness and spacing of the axial slices, there is some "digital ambiguity" as to which precise slice is to be selected to denote a specific boundary location. For example, for AI(I), where to call the exact slice where the abdominal aorta bifurcates into common iliac arteries is ambiguous by one or two slices. Thus, even when experts identify boundary slice locations manually, there can be a variation by about two slices. The difference in appearance of boundary slices among subjects also suggests that it may be difficult to automatically locate boundary slices based only on intensity information. For all data sets in our collection I and for all body regions, we have identified the true body region boundary locations TS(I), TI(I), AS(I), AI(I)/PS(I), and PI(I) manually via slice visualization under the guidance of the radiologist in our team (Torigian). These locations will be used as true locations for training our methods and for testing the accuracy of the locations predicted by our approach.

Our problem is: Given any PET/CT image I of a whole body, to find automatically the predicted locations ts(I), ti(I), as(I), ai(I), ps(I), and pi(I) of respectively TS(I), TI(I), AS(I), AI(I), PS(I), and PI(I) that are close to these true locations. We assume that the slices of I are organized axially and the region of the body it covers properly includes the body regions to be identified in I. For whole-body PET/CT imagery, this condition is always met. If this is not the case, the location predicted by our method will extend beyond the body region covered by I and will be in correct relationship with that data set and the subject although the corresponding slice may not be found in I.

Training: Binary/Gray Valued Objects and Their Virtual Landmarks

Reference objects and their segmentation: An object selected as a reference object should satisfy three key conditions: (C1) It should be segmentable reliably fully automatically and simply. (C2) It should not be confined within some small space in the body. (C3) It is manifest with roughly the same form and shape in all subject data sets when derived by the segmentation strategy satisfying C1. In our experience, objects that satisfy these conditions are: skeleton and lungs including trachea and bronchi. These objects can be segmented by thresholding (in CT images) owing to their distinct Hounsfield Unit (HU) ranges, the values we used being: [176, 3071] and [−894, −424] in HU, respectively. We will show results for these objects and discuss their pros and cons. We emphasize that after the thresholding operation, we perform an automated operation to remove any isolated voxels. Thus, the segmentation will correspond to the main reference object bulk. Otherwise, the segmentation does not have to be perfect as long as it is similar in all patients (condition C3).

Figure 26:
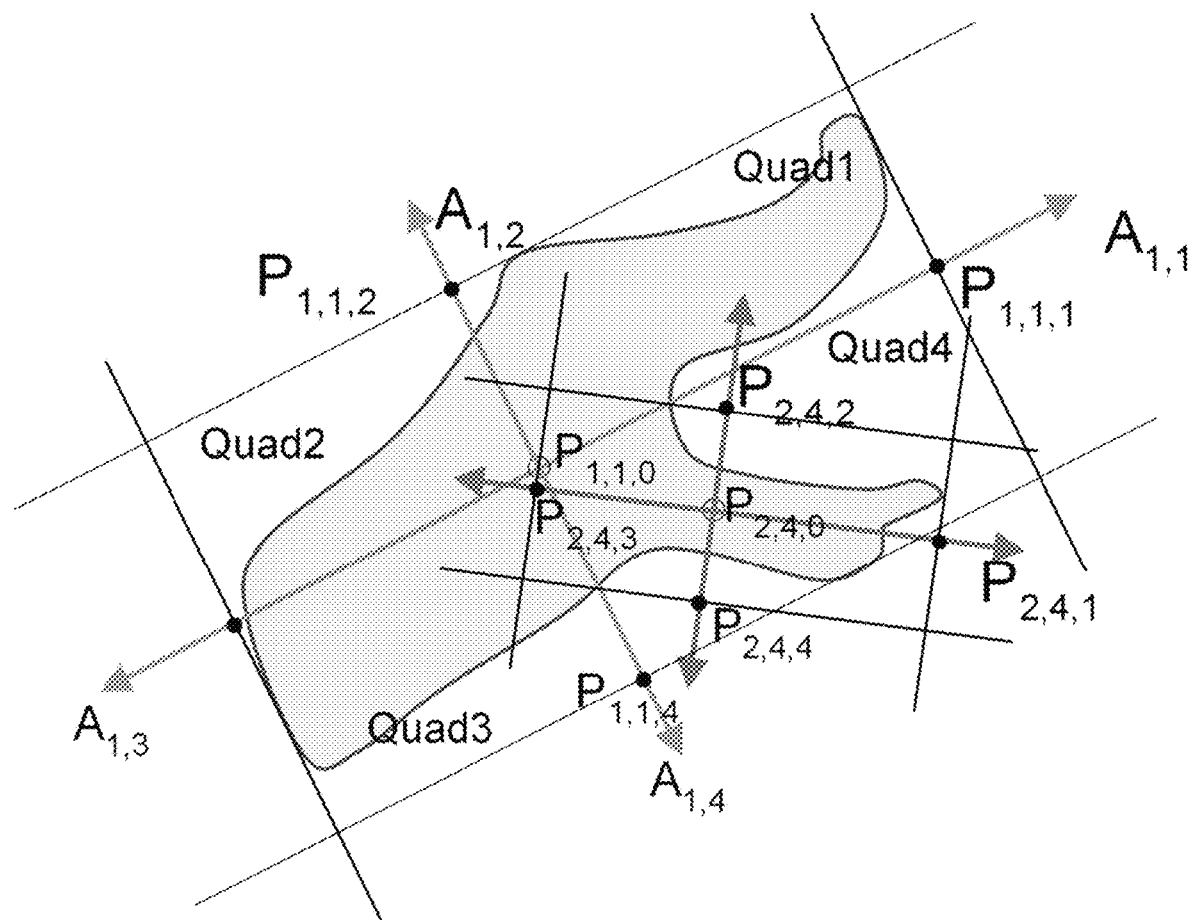
FIG. 26 illustrates an example process for defining virtual landmarks.

Virtual Landmarks: The idea of VLs is illustrated with a 2D (binary) example in FIG. 26. Given a binary image representing the object, Principal Component Analysis (PCA) of the entire binary object is first carried out to find the four principal axes directions, denoted in the figure in green by $A_{1,1}, A_{1,2}, A_{1,3}, A_{1,4}$, emanating from the geometric centroid of the object indicated by $P_{1,1,0}$ (small circle). Along these axes, we find points $P_{1,1,1}, P_{1,1,2}, P_{1,1,3},$ and $P_{1,1,4}$ that indicate the extent of the object in those directions. These five points form the first level landmarks, where the first subscript denotes level number, second denotes quadrant number, and the third indicates point number. These points and the axes subdivide the shape into four pieces in the four quadrants. For each piece, we perform PCA again and find the 20 second level landmarks denoted $P_{2,1,0}, P_{2,1,1}, \ldots, P_{2,1,4}, P_{2,2,0}, \ldots,$ P2,4,4. The five points $P_{2,4,0}, \ldots, P_{2,4,4}$ obtained for the 4th quadrant are shown in the figure for illustration ($2^{nd}$ level principal axes are shown in red). The process continues up to a specified level. Since the points are ordered, each point has a unique label. This allows us to specify the VLs we need by their label for representing a given shape. For example, we may use just the 8 points $P_{1,1,0}, P_{1,1,1}, P_{1,1,2}, P_{1,1,3}, P_{1,1,4}, P_{2,4,1}, P_{2,4,2},$ and $P_{2,4,4}$ (which already denote the shape roughly). Note how the points tend to move closer to the object surface at higher levels. Points at early levels capture overall form and add details at later levels.

The total number N(x) of VLs for a d-dimensional object derived from x levels will be $N(x)=\Sigma_{n=1}^{x}(2d+1)2^{d(n-1)}$. If we consider only the geometric centroids (points identified by 0 value for their $3^{rd}$ subscript index such as $P_{2,2,0}$), the total number of points will be $\Sigma_{n=1}^{x}2^{d(n-1)}$. The approach readily generalizes to multiple objects—either by finding VLs for each object separately and pooling the VLs together, or by first pooling the objects into one object and finding its VLs. The sets of resulting VLs in the two cases may not be the same. For objects with gray CT values, the gray pixel values in the shape are used as a weight factor in PCA computation. Now, the shape as well as the gray values of the object influence the location of the VLs relative to the object. Obviously gray-value-based VLs also generalize straightforwardly from single object to multiple objects and even to vector-valued images.

Note that the VLs may lie anywhere with respect to the object. In fact, in our experience with several anatomic objects, VLs are rarely located exactly on the object boundary. The number of VLs rises rapidly with the number of levels. For example, for a 3D object, $N(1)=7$, $N(2)=63$, and $N(3)=511$. If we consider only geometric centers, $N(1)=1$, $N(2)=9$, and $N(3)=73$. Unlike methods of finding landmarks on object boundaries, the concept of VLs generalizes to spaces of any finite dimension directly and easily. Usually, 50-100 VLs are sufficient to describe a large object. For an early report on the concept of VLs and their general properties, see Ref[19]. In this paper, we will not study these matters and focus only on the application of VLs for localizing body regions. After the reference objects are segmented, their VLs are computed automatically following the above recursive subdivision algorithm. We will test the prediction performance of our approach using different reference objects and both binary and gray-valued versions of the objects.

Training: Learning the Relationship Between VLs and Body Region Boundaries

For this stage, input is the set of VLs of the chosen reference objects in the training image set $I_T$ and the set of true boundary locations TS(I), TI(I), AS(I), AI(I), PS(I), and PI(I) for each image I in $I_T$. The outcome of this stage is a trained neural network. Input-vector-output-vector pairs (u(I), v(I)) used for network training are as follows: (u(I), v(I)), for all I in the training image data set $I_T$, where $u(I)=[P_{1,1,0}(I), P_{1,1,1}(I), P_{1,1,2}(I), \ldots, P_{L,8,0}(I), \ldots, P_{L,8,6}(I)]^t$ and $v(I)=[TS(I), TI(I), AS(I), AI(I), PS(I), PI(I)]^t$. All locations here are expressed in terms of coordinates with respect to the scanner coordinate system associated with image I. Note that each VL is described by its three coordinates and each boundary location TS(I), TI(I), ..., PI(I) is described by one coordinate, namely the coordinate in the cranio-caudal direction.

We employed a neural network regressor (Neural Network Toolbox, Version 9.0, of MATLAB, Version R2016a) to learn the relationship between VLs and boundary locations. This toolbox provides a convenient platform to design an application-oriented neural network. Relevant details pertaining to our application are as follows.

Figure 27:
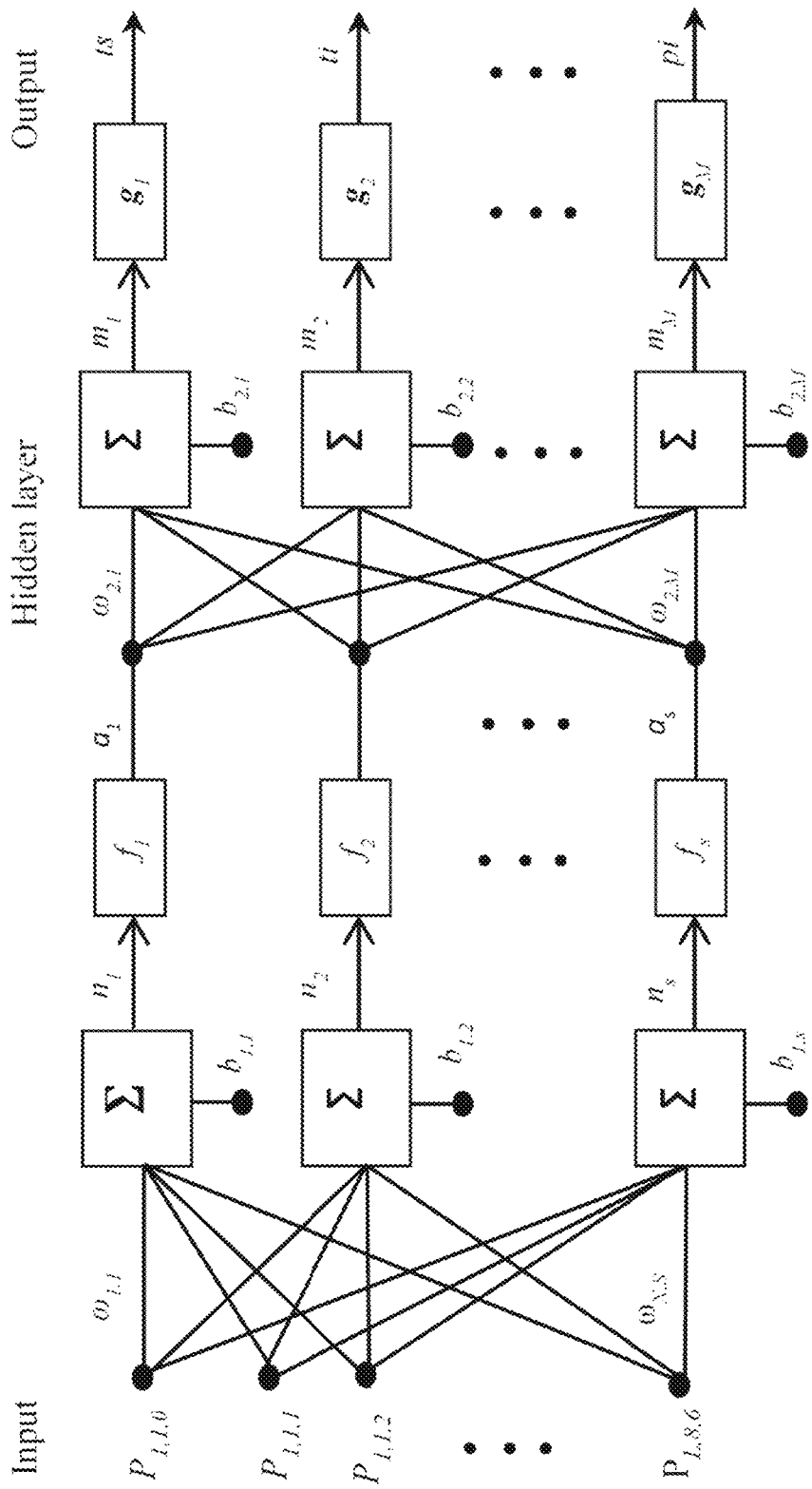
FIG. 27 illustrates an example neural network (e.g., regressor).

Choice of neural network architecture and configuration: As we want to solve a nonlinear mapping problem, a multilayer architecture with a single hidden layer would be sufficient. Here, we follow the layer designation of MATLAB's Neural Network Toolbox. As shown in FIG. 27 a layer of neurons includes the weights, multiplication, and summing operations. It is common for the number of inputs to a layer to be different from the number of neurons. In our application, the input is presented as a set of vectors $\{u(I), I \in I^T\}$. The number of elements in each input vector is $N \times 3$ where N is the number of VLs employed. The number of neurons, denoted as S in the hidden layer, is adjusted to minimize the localization errors. S is not necessarily equal to N. The number of elements in the output vector is $M=6$ (strictly speaking, 5).

Choice of training parameters: For each neuron, there are three operations—the weight function (matrix multiplication), the net input function (summation), and the transfer function. Here, we adopt the "Hyperbolic Tangent Sigmoid" transfer function in the hidden layers, and the "Linear" transfer function in the output layer (which are denoted as "tansig" and "purelin" in MATLAB's toolbox, respectively). The "Bayesian Regularization" training algorithm is employed to prevent overfitting. We employ two stopping criteria, namely, a fixed number of iterations and the gradient of the performance index to control the iterative procedure. The training performance index is selected as Mean Squared Error (which is denoted as "mse" in the toolbox).

Testing: Predicting Body Region Boundary Locations

In this stage, given an image I, first the reference objects employed in the previous stage are identified in I by using the same segmentation strategy as employed in the previous stage. Then, the same specific set of VLs of the reference objects as utilized for training the network is computed. These VLs are fed to the neural network whose output variables correspond to the six predicted boundary locations of the three body regions.

Evaluation

To evaluate the performance of this approach, we compare the predicted boundary locations to the "true" expert determined locations and express the deviation in terms of number of slices, nS, and the distance, dS (in mm), between the two locations. Our evaluations will involve several different divisions of the data set I into training and testing subsets $I_T$ and $I_t$ and multiple folds (different repetitions of this division) and use four reference objects—skeleton and lungs—in both binary and gray forms. We have also experimented with different numbers of VLs—9, 17, 25, and 73. All VLs considered here are geometric centers only and are confined to the first three levels. In our notation, these points are identified by $P_{i,j,0}$ (see FIG. 26). The set with 9 points corresponds to all VLs of this type from the first two levels (1 from $1^{st}$ level+8 from $2^{nd}$ level). The set with 73 points corresponds to all VLs of this type from the first three levels (1+8+64). Sets with 17 and 25 VLs are formed by selecting all VLs from the first two levels and different subsets from the third level. One other variable involved in our experiments is the number of coordinates considered for the VLs—all three coordinates (x, y, z) and only the third coordinate (z) in the cranio-caudal direction. The idea for a single coordinate stems from the consideration that we are interested in predicting only the z-level of the boundary slices.

Results

Figure 28A:
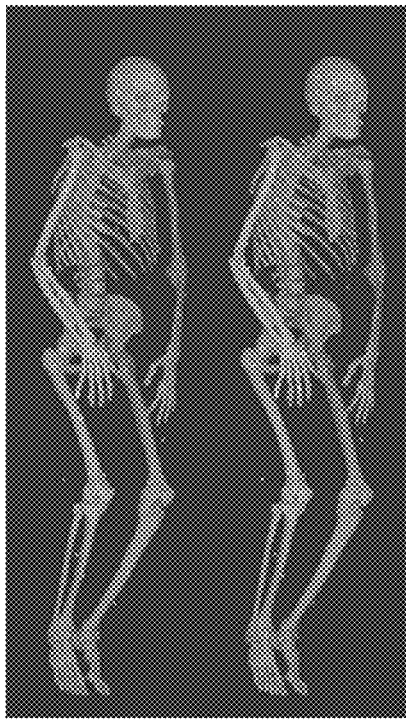
FIG. 28A illustrates an example 3D rendering of a skeleton.
Figure 28B:
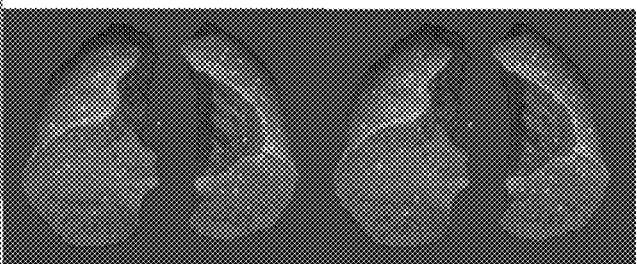
FIG. 28B illustrates an example 3D rendering of lungs along with the associated VLs derived from binary (left) and gray (right) objects.

In FIGS. 28A-B, we depict via 3D renditions the (set of 73) VLs derived from binary and gray versions of sample reference objects obtained from one subject. Notably many VLs lie outside the object. VLs that are interior to the object are not visible in the display. The animations with translucent surface displays available at the link in Ref 23 depict more vividly the spatial distribution of VLs that are interior and exterior to the objects, where the virtual landmarks from both binary image and gray images for the two reference objects are shown.

Figure 29:
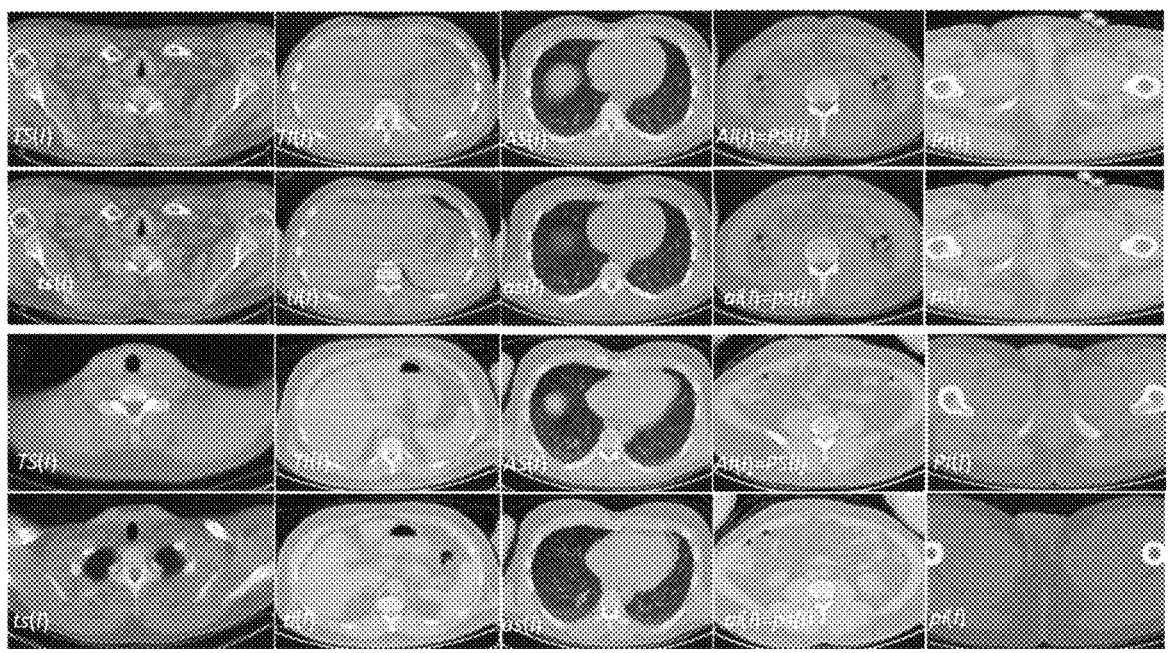
FIG. 29 illustrates an example region boundary slices.
Figure 30:
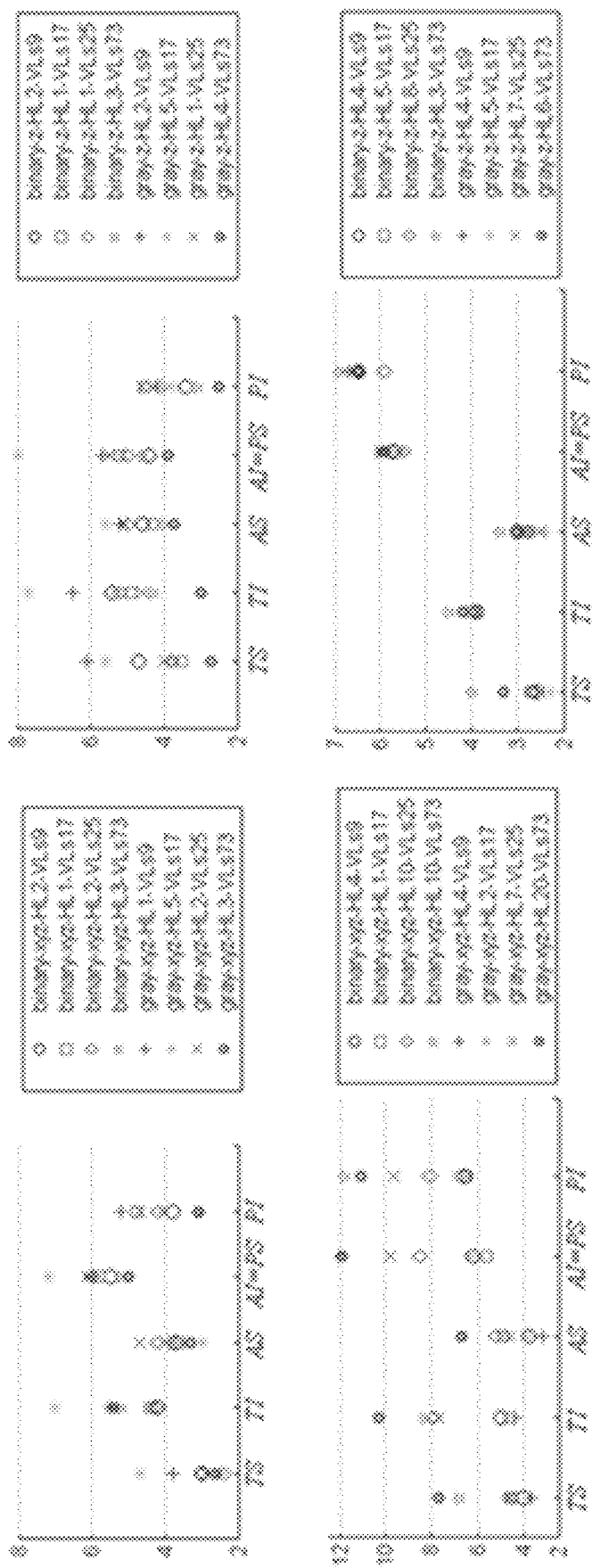
FIG. 30 illustrates example scatter plots of the mean predictive errors listed in Tables E2 and E3 using Skeleton (Row 1) and Lungs (Row 2) as the reference objects and employing (x,y,z) (left column) and (z) (right column) coordinates.

Sample results (good and poor) of identified slices for the region boundaries are displayed in FIG. 29, where the true slices are also shown. Tables E2 and 3E summarize mean prediction errors resulting when Skeleton and Lungs, respectively, are used as reference objects. The tables include results for different settings—binary and gray objects, different numbers of VLs, different selections of coordinates, and different numbers of hidden layers employed in the network. We randomly divided our data samples into training and testing data sets with the ratio 0.85:0.15 and repeated the experiments 6 times for the case of using lungs as the reference object on the 146 near-whole-body scans and 3 times (at the same ratio) for the case of using skeleton as the reference object on the 34 whole-body scans. FIG. 30 shows scatter plots of the mean prediction errors (nS) listed in Tables E2 and E3 using Skeleton and Lungs as reference objects and employing (x, y, z) and (z) coordinates. To study the difference in prediction accuracy among different scenarios, we performed T-tests pairwise between different scenarios. P values from such comparisons using binary versus gray images are summarized in Table E4. To understand the accuracy of our method, we conducted an experiment to study the variability in body region boundary localization by knowledgeable operators. Table E5 summarizes the variability found between two operators in labeling all 6 boundary locations in all 180 CT data sets.

Discussions

We make the following inferences from Tables E2-E5.

(a) For a given region boundary, prediction accuracy varies with gray/binary objects utilized for deriving VLs, the number of VLs used, coordinate selection, number of hidden layers in the network, and the actual reference object. For example, in Table E2, for virtual landmarks from binary mask and gray image, with the same number of hidden layers (2) and virtual landmarks (25), the average prediction error is 4.2 and 16.8 for nS and dS, receptively for binary mask and 4.8 and 19.1 for gray image. We can also observe a similar difference in Table E3. FIG. 30 shows scatter plots of the mean prediction errors for nS listed in Tables E2 and E3, where the different experimental scenarios are also indicated. For example, 'Binary-xyz-HL2-VLs9' denotes the situation of using binary object, (x,y,z) coordinates, 2 hidden layers, and 9 virtual landmark points. Two observations can be made from the scatter plots. The spread of error for localizing AS(I) seems to be the smallest among all boundaries. Also, although the errors themselves are larger, the spread of the errors seems to be the smallest for the case of using Lungs with z-coordinate only.

TABLE E2

Mean and SD (second entry in each cell) of prediction errors nS and dS (in mm) over all tested data sets for the different region boundaries when using Skeleton as the reference object. The column Mean shows mean error over all region boundaries over all tested data sets. Bold entries indicate the setting with the best result.

| Object | Train/Test/Folds | (x, y, z) or (z) | Hidden layers | VLs | ts(I) nS | ts(I) dS | ti(I) nS | ti(I) dS | as(I) nS | as(I) dS | ai(I) = ps(I) nS | ai(I) = ps(I) dS | pi(I) nS | pi(I) dS | Mean nS | Mean dS |
|---|---|---|---|---|---|---|---|---|---|---|---|---|---|---|---|---|
| Binary | 29/5/3 | (x, y, z) | 2 | 9 | 3.0 | 12.0 | 4.2 | 16.6 | 3.7 | 14.9 | 5.5 | 22.0 | 3.8 | 15.0 | 4.0 | 16.1 |
|  |  |  |  |  | 2.5 | 10.0 | 3.1 | 12.5 | 2.7 | 10.7 | 2.9 | 11.6 | 2.8 | 11.1 |  |  |
|  |  |  | 1 | 17 | 3.0 | 12.2 | 4.4 | 17.5 | 3.6 | 14.3 | 5.8 | 23.4 | 4.8 | 19.1 | 4.3 | 17.3 |
|  |  |  |  |  | 1.9 | 7.7 | 3.0 | 12.0 | 2.9 | 11.7 | 4.3 | 17.0 | 4.0 | 15.8 |  |  |
|  |  |  | 2 | 25 | 2.4 | 9.7 | 4.3 | 17.0 | 4.2 | 16.8 | 6.0 | 23.9 | 4.2 | 16.6 | 4.2 | 16.8 |
|  |  |  |  |  | 2.2 | 8.9 | 2.9 | 11.6 | 3.0 | 11.9 | 3.4 | 13.5 | 2.1 | 8.3 |  |  |
|  |  |  | 3 | 73 | 2.6 | 10.5 | 5.2 | 20.8 | 3.5 | 14.0 | 5.2 | 20.7 | 3.1 | 12.4 | 3.9 | 15.7 |
|  |  |  |  |  | 1.5 | 6.1 | 3.1 | 12.3 | 2.3 | 9.2 | 3.1 | 12.4 | 2.2 | 8.6 |  |  |
|  |  | (z) | 2 | 9 | 4.7 | 18.7 | 5.4 | 21.5 | 4.6 | 18.5 | 4.4 | 17.5 | 3.4 | 13.7 | 4.5 | 18.0 |
|  |  |  |  |  | 2.9 | 11.7 | 3.5 | 14.2 | 3.3 | 13.2 | 3.2 | 12.7 | 1.8 | 7.2 |  |  |
|  |  |  | 1 | 17 | 3.5 | 13.9 | 4.9 | 19.7 | 4.3 | 17.3 | 5.2 | 20.8 | 4.5 | 18.0 | 4.5 | 17.9 |
|  |  |  |  |  | 2.6 | 10.5 | 3.0 | 12.0 | 2.5 | 10.1 | 4.4 | 17.4 | 4.1 | 16.3 |  |  |
|  |  |  | 1 | 25 | 3.8 | 15.0 | 5.2 | 20.8 | 5.0 | 19.9 | 5.0 | 20.1 | 4.1 | 16.4 | 4.6 | 18.4 |
|  |  |  |  |  | 2.8 | 11.0 | 3.2 | 13.0 | 2.7 | 10.8 | 4.4 | 17.6 | 3.1 | 12.5 |  |  |
|  |  |  | 3 | 73 | 3.8 | 15.4 | 4.3 | 17.3 | 4.0 | 16.1 | 4.6 | 18.3 | 3.1 | 12.5 | 4.0 | 15.9 |
|  |  |  |  |  | 3.4 | 13.5 | 3.5 | 13.9 | 1.5 | 6.1 | 3.0 | 11.8 | 2.3 | 9.2 |  |  |
| Gray | 29/5/3 | (x, y, z) | 1 | 9 | 3.8 | 15.2 | 5.5 | 22.0 | 3.9 | 15.6 | 6.0 | 24.0 | 5.2 | 20.8 | 4.9 | 19.5 |
|  |  |  |  |  | 3.0 | 12.1 | 4.3 | 17.3 | 2.2 | 8.7 | 4.4 | 17.7 | 3.5 | 13.8 |  |  |
|  |  |  | 5 | 17 | 4.7 | 18.8 | 7.0 | 28.1 | 3.0 | 12.2 | 7.2 | 28.6 | 4.1 | 16.2 | 5.2 | 20.8 |
|  |  |  |  |  | 2.9 | 11.5 | 4.5 | 18.0 | 2.0 | 8.1 | 4.1 | 16.3 | 2.2 | 8.9 |  |  |
|  |  |  | 2 | 25 | 2.9 | 11.8 | 5.5 | 21.9 | 4.7 | 18.8 | 6.1 | 24.4 | 4.7 | 18.7 | 4.8 | 19.1 |
|  |  |  |  |  | 2.3 | 9.3 | 3.3 | 13.1 | 3.0 | 12.1 | 3.8 | 15.4 | 2.3 | 9.2 |  |  |
|  |  |  | 3 | 73 | 2.6 | 10.6 | 5.4 | 21.6 | 3.3 | 13.0 | 5.0 | 19.9 | 3.1 | 12.4 | 3.9 | 15.5 |
|  |  |  |  |  | 1.5 | 5.9 | 3.3 | 13.1 | 2.2 | 8.9 | 3.4 | 13.7 | 2.8 | 11.4 |  |  |
|  |  | (z) | 2 | 9 | 6.1 | 24.5 | 6.5 | 26.1 | 5.2 | 20.6 | 5.7 | 22.7 | 4.2 | 16.9 | 5.5 | 22.2 |
|  |  |  |  |  | 4.5 | 18.0 | 4.8 | 19.1 | 3.3 | 13.0 | 5.6 | 22.4 | 4.2 | 17.0 |  |  |
|  |  |  | 5 | 17 | 5.6 | 22.3 | 7.7 | 30.9 | 5.6 | 22.5 | 8.0 | 31.8 | 3.8 | 15.1 | 6.1 | 24.5 |
|  |  |  |  |  | 2.5 | 10.1 | 5.3 | 21.1 | 4.7 | 18.8 | 4.3 | 17.3 | 3.1 | 12.4 |  |  |
|  |  |  | 1 | 25 | 4.0 | 15.8 | 4.6 | 18.5 | 5.1 | 20.3 | 5.5 | 22.1 | 4.6 | 18.3 | 4.8 | 19.0 |
|  |  |  |  |  | 2.0 | 7.8 | 4.2 | 16.7 | 2.9 | 11.4 | 4.3 | 17.1 | 3.7 | 14.7 |  |  |
|  |  |  | 4 | 73 | 2.7 | 10.9 | 3.0 | 12.1 | 3.7 | 14.7 | 3.9 | 15.8 | 2.5 | 10.2 | 3.2 | 12.7 |
|  |  |  |  |  | 1.8 | 7.1 | 3.0 | 12.0 | 1.9 | 7.7 | 3.2 | 12.7 | 1.8 | 7.4 |  |  |

TABLE E3

Mean and SD (second entry in each cell) of prediction errors nS and dS (in mm) over all tested data sets for the different region boundaries when using Lungs as the reference object. The column Mean shows mean error over all region boundaries over all tested data sets. Bold entries indicate the setting with the best result.

| Object | Train/Test/Folds | (x, y, z) or (z) | Hidden layers | VLs | ts(I) nS | ts(I) dS | ti(I) nS | ti(I) dS | as(I) nS | as(I) dS | ai(I) = ps(I) nS | ai(I) = ps(I) dS | pi(I) nS | pi(I) dS | Mean nS | Mean dS |
|---|---|---|---|---|---|---|---|---|---|---|---|---|---|---|---|---|
| Binary | 153/27/6 | (x, y, z) | 4 | 9 | 4.0 | 15.0 | 5.0 | 18.6 | 3.8 | 14.3 | 6.2 | 23.5 | 6.6 | 25.1 | 5.1 | 19.3 |
| | | | | | 3.5 | 13.3 | 5.3 | 19.5 | 3.7 | 14.0 | 5.2 | 20.0 | 5.6 | 21.2 | | |
| | | | 1 | 17 | 4.5 | 17.2 | 4.6 | 17.1 | 4.9 | 18.4 | 5.6 | 21.5 | 6.5 | 24.8 | 5.2 | 19.8 |
| | | | | | 3.7 | 14.2 | 5.3 | 19.7 | 3.8 | 14.6 | 5.0 | 18.9 | 4.8 | 18.2 | | |
| | | | 10 | 25 | 4.6 | 17.3 | 7.9 | 29.7 | 5.2 | 19.6 | 8.5 | 32.2 | 8.1 | 31.0 | 6.9 | 26.0 |
| | | | | | 4.2 | 15.8 | 7.7 | 28.5 | 5.0 | 18.9 | 6.9 | 26.3 | 6.8 | 25.6 | | |
| | | | 10 | 73 | 6.8 | 25.3 | 8.3 | 31.1 | 6.7 | 25.0 | 12.0 | 45.1 | 11.8 | 44.2 | 9.1 | 34.1 |
| | | | | | 7.2 | 26.8 | 8.1 | 30.1 | 6.3 | 23.8 | 10.9 | 41.1 | 10.2 | 38.0 | | |
| | | (z) | 4 | 9 | 2.6 | 9.7 | 3.9 | 14.6 | 3.0 | 11.2 | 5.7 | 21.7 | 6.5 | 24.8 | 4.3 | 16.4 |
| | | | | | 2.7 | 10.5 | 4.4 | 16.3 | 2.9 | 10.9 | 5.0 | 19.0 | 5.0 | 19.2 | | |
| | | | 5 | 17 | 2.7 | 10.3 | 4.0 | 15.0 | 2.8 | 10.8 | 5.7 | 21.9 | 6.5 | 24.6 | 4.3 | 16.5 |
| | | | | | 2.7 | 10.3 | 4.6 | 16.8 | 2.8 | 10.6 | 5.0 | 19.1 | 4.9 | 18.9 | | |
| | | | 8 | 25 | 2.7 | 10.3 | 3.9 | 14.7 | 2.8 | 10.4 | 5.5 | 21.1 | 5.9 | 22.3 | 4.2 | 15.7 |
| | | | | | 2.8 | 10.7 | 4.5 | 16.6 | 2.7 | 10.4 | 4.8 | 18.3 | 4.6 | 17.7 | | |
| | | | 3 | 73 | 4.0 | 15.2 | 4.5 | 16.8 | 3.4 | 12.9 | 6.0 | 22.9 | 6.9 | 26.0 | 5.0 | 18.8 |
| | | | | | 3.5 | 13.5 | 5.1 | 18.9 | 3.2 | 12.1 | 5.4 | 20.4 | 5.1 | 19.3 | | |
| Gray | 153/27/6 | (x, y, z) | 4 | 9 | 3.7 | 13.8 | 4.4 | 16.7 | 3.2 | 12.2 | 6.3 | 24.0 | 6.7 | 25.5 | 4.9 | 18.4 |
| | | | | | 3.5 | 13.1 | 5.1 | 18.9 | 3.1 | 12.0 | 5.2 | 19.9 | 5.5 | 20.9 | | |
| | | | 2 | 17 | 4.6 | 17.3 | 4.8 | 18.0 | 3.9 | 14.8 | 6.3 | 23.8 | 6.9 | 26.3 | 5.3 | 20.0 |
| | | | | | 4.1 | 15.7 | 5.2 | 19.0 | 3.4 | 12.8 | 5.2 | 20.1 | 5.3 | 20.4 | | |
| | | | 7 | 25 | 4.6 | 17.3 | 7.7 | 28.8 | 4.6 | 17.2 | 9.8 | 36.9 | 9.6 | 36.1 | 7.3 | 27.3 |
| | | | | | 4.5 | 16.8 | 8.4 | 31.5 | 4.5 | 17.0 | 8.4 | 31.8 | 8.5 | 32.1 | | |
| | | | 20 | 73 | 7.7 | 28.9 | 10.3 | 38.7 | 6.7 | 24.9 | 11.9 | 44.8 | 11.1 | 41.9 | 9.5 | 35.8 |
| | | | | | 6.0 | 22.6 | 9.6 | 36.1 | 6.1 | 22.8 | 10.9 | 41.4 | 9.9 | 37.3 | | |
| | | (z) | 4 | 9 | 2.3 | 8.8 | 3.8 | 14.1 | 2.8 | 10.7 | 5.8 | 22.0 | 6.7 | 25.3 | 4.3 | 16.2 |
| | | | | | 2.6 | 9.8 | 4.4 | 16.2 | 2.8 | 10.7 | 5.0 | 19.0 | 5.2 | 20.0 | | |
| | | | 5 | 17 | 2.3 | 8.8 | 3.8 | 14.3 | 2.4 | 9.1 | 5.5 | 21.1 | 6.4 | 24.3 | 4.1 | 15.5 |
| | | | | | 2.5 | 9.6 | 4.4 | 16.0 | 2.4 | 9.3 | 4.9 | 18.8 | 5.0 | 19.2 | | |
| | | | 7 | 25 | 2.5 | 9.4 | 3.9 | 14.7 | 2.5 | 9.4 | 6.0 | 22.8 | 6.6 | 24.9 | 4.3 | 16.2 |
| | | | | | 2.7 | 10.2 | 4.5 | 16.4 | 2.4 | 9.0 | 5.3 | 20.0 | 5.5 | 20.7 | | |
| | | | 6 | 73 | 3.3 | 12.5 | 4.2 | 15.8 | 3.0 | 11.3 | 5.9 | 22.6 | 6.5 | 24.8 | 4.6 | 17.4 |
| | | | | | 3.3 | 12.6 | 4.9 | 18.2 | 2.9 | 11.2 | 5.1 | 19.3 | 4.8 | 18.5 | | |

(b) Our observations from Table E4 (and other similar comparisons) can be summarized as follows. (i) When using the skeleton as the reference object with smaller number of hidden layers (≤5) and VLs (≤17) the mean prediction error (nS~4) is lower (P<0.02) than when using larger number of hidden layers and VLs (nS~5). (ii) With lung as the reference object (binary or gray), in almost all scenarios with the same number of hidden layers but using different number of VLs, the prediction error was statistically significantly (P<0.001) greater when using smaller number of VLs. (iii) The difference in accuracy between (x, y, z) versus z over all was not statistically significant (not shown in Table E4). (iv) Comparing between the two reference objects, the best accuracy achieved with skeleton (bold in Table E2) is better (P<x) than the best accuracy achieved with lungs (bold in Table E3).

TABLE E4

P values from T-Tests comparing prediction errors over all boundary locations by using VLs from binary mask versus VLs from gray region.

| | Skelton as reference object | | | | Lungs as reference object | | | |
|---|---|---|---|---|---|---|---|---|
| (x, y, z) or (z) | Hidden layers (binary/gray) | VLs (binary/gray) | Mean prediction error (nS) (binary/gray) | P value | (x, y, z) or (z) | Hidden layers (binary/gray) | VLs (binary/gray) | Mean prediction error (nS) (binary/gray) | P value |
| (x, y, z) | 2/1 | 9/9 | 4.0/4.9 | 0.0122 | (x, y, z) | 4/4 | 9/9 | 5.1/4.9 | 0.0069 |
| | 1/5 | 17/17 | 4.3/5.2 | 0.0518 | | 1/2 | 17/17 | 5.2/5.3 | 0.5634 |
| | 2/2 | 25/25 | 4.2/4.8 | 0.0062 | | 10/7 | 25/25 | 6.9/7.3 | 0.1498 |
| | 3/3 | 73/73 | 3.9/3.9 | 0.7845 | | 10/20 | 73/73 | 9.1/9.5 | 0.2865 |
| (z) | 2/2 | 9/9 | 4.5/5.5 | 0.0211 | (z) | 4/4 | 9/9 | 4.3/4.3 | 0.1465 |
| | 1/5 | 17/17 | 4.5/6.1 | 0.0027 | | 5/5 | 17/17 | 4.3/4.1 | 0.0002 |
| | 1/1 | 25/25 | 4.6/4.8 | 0.4623 | | 8/7 | 25/25 | 4.2/4.3 | 0.1257 |
| | 3/4 | 73/73 | 4.0/3.2 | 0.0030 | | 3/6 | 73/73 | 5.0/4.6 | 0.0058 |

TABLE 5

Mean (and SD) of the variability in
nS and dS observed in boundary localization
by two operators.

|  | TS(I) | TI(I) | AS(I) | AI(I) = PS(I) | PI(I) |
|---|---|---|---|---|---|
| nS | 0.10 | 1.04 | 0.14 | 3.19 | 0.76 |
|  | 0.29 | 0.81 | 0.42 | 1.99 | 0.64 |
| dS (mm) | 0.4 | 4.16 | 0.56 | 12.76 | 3.04 |
|  | 1.16 | 3.24 | 1.68 | 7.96 | 2.56 |

(c) From Table E5 we observe that expert variability is the smallest for TS(I) and AS(I), intermediate for TI(I) and PI(I), and notably the largest for AI(I)=PS(I). The best accuracy achieved (shown in bold in Tables E2 and E3) is variable among the different region boundaries and follows the trend in variability in expert localization of the boundaries. That is, when expert localization variability is greater so is the error in automatic localization. AI(I) is the most challenging to localize for our method as well as for experts. The best overall mean localization accuracy (error) for our method is nS=4.1 and dS=15.5 mm for the case of using lungs as the reference object, and nS=3.2 and dS=12.7 mm for the case of using skeleton as the reference object.

(d) Some region boundaries are more challenging than others for accurate localization (recall FIG. 24). As seen from Tables E2 and E3, TI, AI=PS, and PI seem to have less accuracy than the locations in the superior portion of the thorax. This may be due to large motion of the inferior thorax and abdominopelvic regions compared to the upper parts of the thorax.

(e) Dependence of accuracy on reference object size and shape is hard to decode. Objects that have larger spatial coverage seem to fare better than spatially confined objects. What seems to matter most is the precision of the relationship between the chosen VLs and region boundaries. Generally, the skeleton as the reference object seems to fare better than lungs, notably for PI, AI=PS, and TI.

Figure 31:
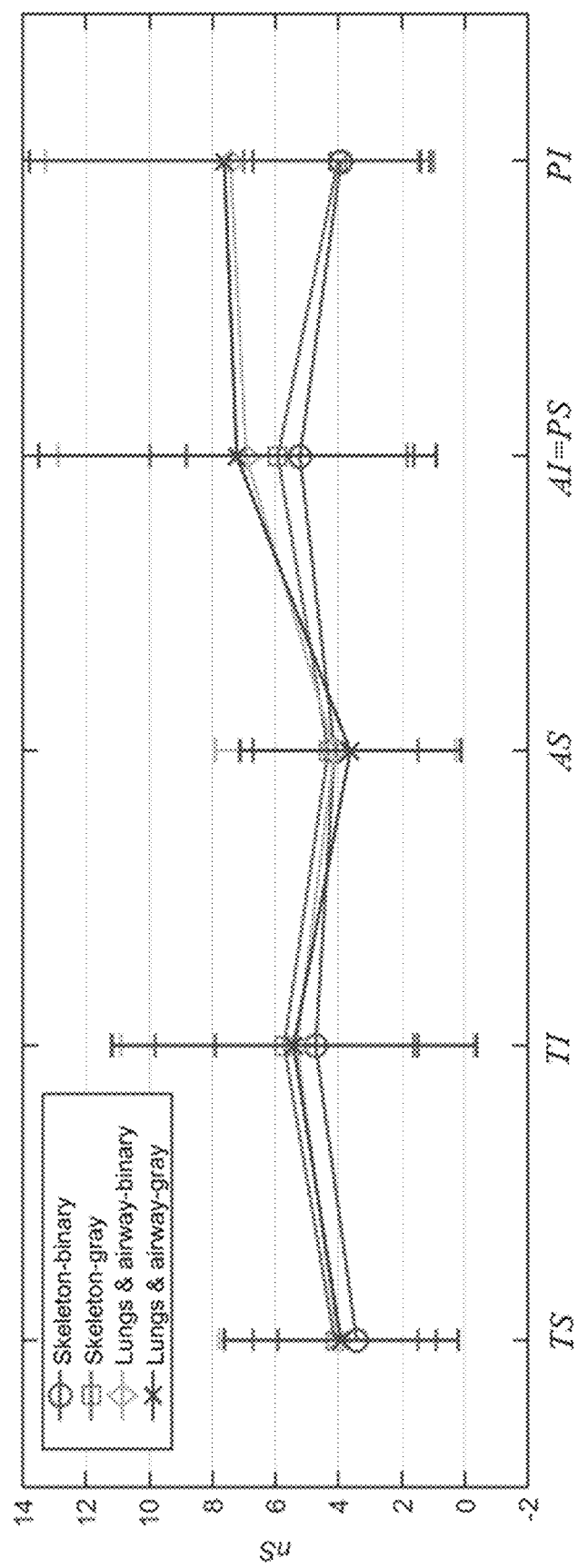
FIG. 31 illustrates an example graphical comparison of mean prediction error (nS) for all region boundaries for different reference objects.

(f) In principle, gray values bring in an additional subtlety to VL definition from image intensity pattern details. However, similar localization accuracies are obtained for VLs from gray objects and binary versions as graphically illustrated in FIG. 31 which displays errors in nS for the different cases of objects and gray/binary versions of VLs. The vertical intervals indicate one standard deviation on either side of the mean.

Figure 32:
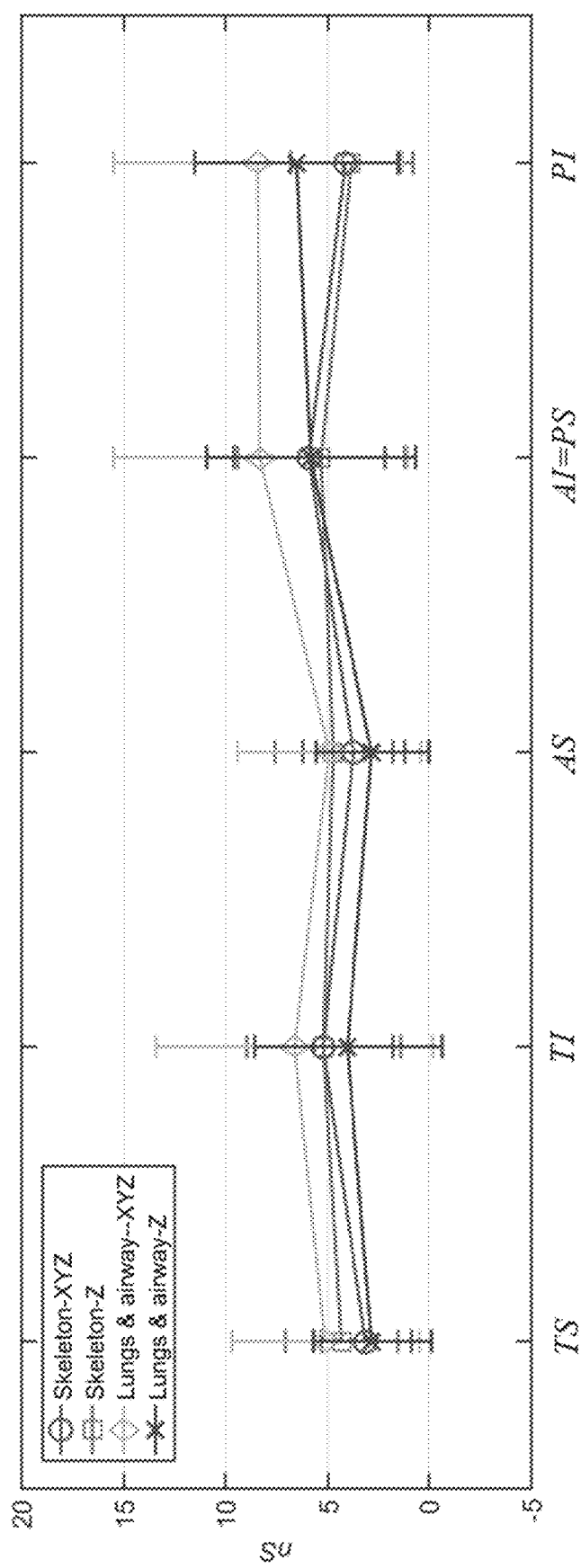
FIG. 32 illustrates an example graphical comparison of mean prediction error over all regions for different reference objects.

(g) VLs with just their z coordinates seem to regress their relationship to region boundaries just as well as or better than all three coordinates taken together. FIG. 32 graphically illustrates the differences. This suggests that the location of the VLs on the slice plane is less important than their slice location in the cranio-caudal direction. As mentioned in (iv) above, the precision of the relationship to region boundaries is perhaps better for z alone versus all coordinates collectively.

(h) Variability in localization error (expressed by SD values in the tables) seems to be generally smaller for gray-value-based VLs than for their binary counterpart. A similar trend can be observed for the locations which are affected by the larger motion of the thoraco-abdominal junction.

Computational considerations: Time for VL computation on an Intel® Core™ i7-7700K Processor (4-cores) computer with 64 GB RAM under Ubuntu 16.04 OS is in the range 150 s-230 s per data set. When a large number of VLs with all (x, y, z) coordinates are employed, more neurons in the hidden layer will be needed and consequently, the training time goes up. For example, when dealing with 73 lung VLs with (x, y, z) coordinates, the training time is 4169 seconds, while the prediction time per data set for any configuration is ~0.3 second.

Automatic localization of human body regions in clinical images can facilitate image reading, reporting, and quantification. More importantly, this becomes essential in systems designed for automatic recognition of anatomic organs and zones such as lymph node stations when such systems employ precise definitions of body regions, organs, and zones. In this paper, we presented a novel strategy for accomplishing this task based on the concept of virtual landmarks and learning their relationship to boundary locations of body regions via a neural network. The method can be utilized for carving out precisely (within about 3 slices) a specific body region or multiple body regions from a whole-body scan.

There are several potential applications of virtual landmarks in image and object analytics. One avenue we are currently pursuing is in organ localization (recognition). We are also examining the use of multiple objects simultaneously, instead of individually as investigated in this paper, for potentially improving accuracy. We believe that not all VLs behave the same way, and so weeding out those VLs that show large subject-to-subject variation in their relationship (particularly in z value) to boundary locations may improve performance. On diagnostic CT scans, which are typically performed on individual body regions and not the whole body, performance may be better than on the low-dose CT scans we studied in this paper, specifically when gray-valued objects are used for computing VLs. A separate investigation is needed to study this task of individual body region localization on individual body region scans. We are also developing deep learning methods to localize region boundaries without the use of VLs. As we pointed out earlier, higher level landmarks correspond to fine structures and tend to be patient dependent. The issue of how to capture fine granularity via higher-level VLs and describe differences in objects at that level over a population is another interesting topic of study for the future.

In the present disclosure, a new method to localize the thoracic body region from whole-body or near whole-body PET/CT scans is presented. The key idea is to find a nonlinear mapping relationship between the 3D virtual landmarks and the ground-truth of body-region boundaries. By searching key points along the shape of reference objects with a multiple levels style, the obtained virtual landmarks can represent a large object effectively. The relationship between the virtual landmarks and ground-truth positions can then be learned by employing a simple neural network regressor. Experimental results confirm that the present method can localize body-region boundaries automatically and reliably with promising accuracy. It is interesting that the accuracy of localizing specific body-region boundaries seems to be dependent on the reference object(s) and the particular virtual landmarks employed.

Those skilled in the art also will readily appreciate that many additional modifications are possible in the exemplary embodiment without materially departing from the novel teachings and advantages of the invention. Accordingly, any such modifications are intended to be included within the scope of this invention as defined by the following exemplary claims.

What is claimed:

1. A computerized method of providing, based on medical images, quantification of body-wide tissue composition including one or more of subcutaneous adipose tissue (SAT), visceral adipose tissue (VAT), muscle tissue, and bone tissue via automatic anatomy recognition, the method comprising the steps of:
   determining, based on automatically identifying a plurality of virtual landmarks in a set of medical images, a body region of interest, wherein determining the body region of interest comprises determining, based on one or more of the plurality of virtual landmarks, a first image slice indicative of a first boundary of the body region of interest and determining, based on one or more of the plurality of virtual landmarks, a second image slice indicative of a second boundary of the body region of interest;
   generating, based on at least a portion of the set of medical images associated with the body region of interest, a fuzzy anatomy model of the body region of interest; and
   using, based on one or more patient images and the fuzzy anatomy model, automatic anatomy recognition (AAR) to recognize and delineate one or more tissue objects, in the body region of interest of a patient, wherein the tissue objects comprise one or more of a subcutaneous adipose tissue (SAT) object, a visceral adipose tissue (VAT) object, a muscle tissue object, or a bone tissue object.

2. The computerized method of claim 1, further comprising:
   determining, using at least positron emission tomography imaging data from the one or more patient images, a disease burden in the body region of interest of the patient.

3. The computerized method of claim 1, wherein generating a fuzzy anatomy model of the body region of interest comprises gathering image data from the set of medical images determining definitions of each body region and organ and delineating them following said definitions, building hierarchical fuzzy anatomy models of organs and/or tissues for each body region, and selecting from the hierarchical fuzzy anatomy models the fuzzy anatomy model of the body region of interest.

4. The computerized method of claim 3, wherein using AAR to recognize and delineate one or more tissue objects in the body region of interest comprises recognizing and locating organs and/or tissues in the one or more patient images by employing the hierarchical fuzzy anatomy models, and delineating tissue objects indicating specific tissue types in the body region of interest following the hierarchy.

5. The computerized method of claim 1, wherein the body region of interest comprises a region from a body torso.

6. A system that provides, based on medical images, quantification of body-wide tissue composition including one or more of subcutaneous adipose tissue (SAT), visceral adipose tissue (VAT), muscle tissue, and bone tissue via automatic anatomy recognition, the system comprising:
   a database that stores image data from medical image sets;
   a memory storing computer instructions; and
   a processor that processes the computer instructions to:
      determine, based on automatically identifying a plurality of virtual landmarks in a medical image set of the image data, a body region of interest, wherein determining the body region of interest comprises determining, based on one or more of the plurality of virtual landmarks, a first image slice indicative of a first boundary of the body region of interest and determining, based on one or more of the plurality of virtual landmarks, a second image slice indicative of a second boundary of the body region of interest;
      generate, based on at least a portion of the image data associated with the body region of interest, a fuzzy anatomy model of the body region of interest; and
      use automatic anatomy recognition (AAR) to recognize and delineate, based on one or more patient images and the fuzzy anatomy model, one or more tissue objects in the body region of interest for a particular patient, wherein the one or more tissue objects comprise one or more of a subcutaneous adipose tissue (SAT) object, a visceral adipose tissue (VAT) object, a muscle tissue object, and a bone tissue object.

7. The system of claim 6, wherein the processor is further configured to determine, using at least image data from the one or more patient images, a disease burden in the body region of interest of the patient.

8. A computerized method of recognizing, staging, and quantifying, via automatic anatomy recognition and based on patient images, abnormal states within objects body-wide, the method comprising the steps of:
   determining, based on automatically identifying using an iterative principal component analysis process a plurality of virtual landmarks in a set of medical images, a body region of interest;
   locating, based on determining the body region of interest, an object in the body region of interest of a particular patient; and
   determining, using at least image data from the set of medical images, an indication of a disease in the located object.

9. The computerized method of claim 8, wherein the indication of disease comprises an indication of a disease burden, wherein the indication of the disease burden is calculated based on determining, for each voxel associated with the object, a disease severity value indicating presence of a disease in the voxel.

10. The computerized method of claim 8, wherein the indication of the disease comprises one or more of a metric quantifying the disease, a disease stage, a re-stage state, or a predictive state analysis.

11. The computerized method of claim 8, further comprising:
   determining, using at least image data from the set of medical images, a treatment plan for the particular patient.

12. The computerized method of claim 8, wherein the virtual landmarks are not limited to a surface of the object.

13. The computerized method of claim 8, wherein determining the body region of interest is based on using a machine learning model trained to correlate virtual landmarks with corresponding boundaries of body regions of interest.

14. The computerized method of claim 8, wherein the iterative principal component analysis process comprises performing a first level principal component analysis defining one or more octants and performing a first level principal component analysis within at least one of the one or more octants.

15. The computerized method of claim 1, wherein each of the one or more tissue objects comprises a set of voxels in the body region of interest that are identified as comprising a tissue type associated with the tissue object.

16. The computerized method of claim 1, wherein using AAR to recognize and delineate one or more tissue objects comprises determining on a voxel-by-voxel basis an indication of whether a tissue type of the tissue object is located in the corresponding voxel.

17. The computerized method of claim 1, wherein the set of medical images comprises one or more of positron emission tomography, computed tomography images, or low-dose computed tomography images.

18. The computerized method of claim 1, wherein automatically identifying the plurality of virtual landmarks in the set of medical images comprises:
performing an iterative process for determining the plurality of virtual landmarks, wherein at least one iteration of the iterative process comprises a predetermined process that automatically determines virtual landmark locations based on a prior virtual landmark without further analysis of any objects in the set of medical images.

19. The computerized method of claim 1, wherein the first boundary comprises a superior boundary and the second boundary comprises an inferior boundary.

20. The computerized method of claim 8, wherein the virtual landmarks are able to be located in an image at any of the following locations: on a surface of the object, outside the object, and inside the object.

* * * * *